(12) United States Patent
Hedayat et al.

(10) Patent No.: US 10,591,398 B2
(45) Date of Patent: *Mar. 17, 2020

(54) SOOT SENSOR SYSTEM

(71) Applicant: Stoneridge, Inc., Novi, MI (US)

(72) Inventors: Kayvan Hedayat, Weston, MA (US); John Hart, Lexington, OH (US); Eric Matson, Bellville, OH (US); Mark Wilson, Mansfield, OH (US); Norman Poirier, Raynham, MA (US)

(73) Assignee: Stoneridge, Inc., Novi, MI (US)

( * ) Notice: Subject to any disclaimer, the term of this patent is extended or adjusted under 35 U.S.C. 154(b) by 16 days.

This patent is subject to a terminal disclaimer.

(21) Appl. No.: 15/639,166

(22) Filed: Jun. 30, 2017

(65) Prior Publication Data
US 2018/0113062 A1  Apr. 26, 2018

Related U.S. Application Data

(63) Continuation of application No. 14/539,991, filed on Nov. 12, 2014, now Pat. No. 9,696,249.
(Continued)

(51) Int. Cl.
*G01N 15/00* (2006.01)
*G01N 15/06* (2006.01)
*G01M 15/10* (2006.01)

(52) U.S. Cl.
CPC ...... *G01N 15/0656* (2013.01); *G01M 15/102* (2013.01); *G01N 15/0606* (2013.01); *G01N 2015/0046* (2013.01)

(58) Field of Classification Search
CPC .. G01M 15/102; G01M 15/10; G01N 1/2252; G01N 15/0656; G01N 15/0606;
(Continued)

(56) References Cited

U.S. PATENT DOCUMENTS 8,286,470 B2 * 10/2012 Bevot ............... G01N 27/4067
73/114.69
9,212,971 B2 * 12/2015 Oesselke ............ G01M 15/104
(Continued)

FOREIGN PATENT DOCUMENTS

DE   102011078242   12/2011
JP   2012083121   4/2012

OTHER PUBLICATIONS

International Search Report and Written Opinion dated Mar. 25, 2015 in corresponding PCT Patent Application U.S. Serial No. PCT/US2014/065327.
(Continued)

*Primary Examiner* — Blake A Tankersley
(74) *Attorney, Agent, or Firm* — Grossman, Tucker, Perreault & Pfleger, PLLC

(57) ABSTRACT

A soot sensing system includes a soot sensor having a first element, and circuitry to an amount of soot accumulated on the element and to control heating of the element in response to the soot accumulation. An electrostatic repelling voltage (ERV) may be applied to a sensor/heater element(s) during a contamination prevention mode (CPM) to repel ash and reduce contamination of the sensor. A pulsed heating voltage (PHV) may be applied to the elements during the CPM and a pulsed ERV may be applied to the elements during the "off" period of the PHV. All voltage to the elements may be turned off during the CPM and the elements may be floating/ground. A PHV may be applied to the elements during the CPM and no voltage may be applied to the elements during the "off" period of the PHV. A heating voltage may be applied to the elements during a CPM corresponding to a cold start.

16 Claims, 48 Drawing Sheets

Related U.S. Application Data

(60) Provisional application No. 61/903,581, filed on Nov. 13, 2013, provisional application No. 62/028,275, filed on Jul. 23, 2014.

(58) Field of Classification Search
CPC .......... G01N 2015/0046; F01N 13/008; F01N 2560/05; F02D 41/1466; F02D 41/1494
See application file for complete search history.

(56) References Cited

U.S. PATENT DOCUMENTS

| | | |
|---|---|---|
| 9,696,249 B2 * | 7/2017 | Hedayat .............. G01M 15/102 |
| 2004/0170212 A1 | 9/2004 | Streit et al. |
| 2012/0324981 A1 | 12/2012 | Hedayat et al. |
| 2013/0000280 A1 | 1/2013 | Korenev |
| 2013/0000678 A1 | 1/2013 | Hocken et al. |
| 2013/0256296 A1 | 10/2013 | Hocken et al. |
| 2015/0114848 A1 * | 4/2015 | Engelke ............. G01N 27/4067 205/775 |

OTHER PUBLICATIONS

Chen et al; "Temperature Dependent Dielectric Properties of Polycrystalline 96%Al2 03"; Paper 2004 MRS Fall Meeting, Nov. 20-Dec. 3, 2004; Boston, MA; Ohio Aerospace Institute/Nasa Glenn Research Center at Lewis Field, Cleveland, OH 44135.
Chinese Office Action dated May 30, 2018 in corresponding Chinese Patent Application No. 201480071536.0.
Chinese Office Action dated Feb. 22, 2019 in corresponding Chinese Patent Application No. 201480071536.0.
European Communication/Extended European Search Report dated May 22, 2017 in corresponding European Patent Application No. 14861263.3.

* cited by examiner

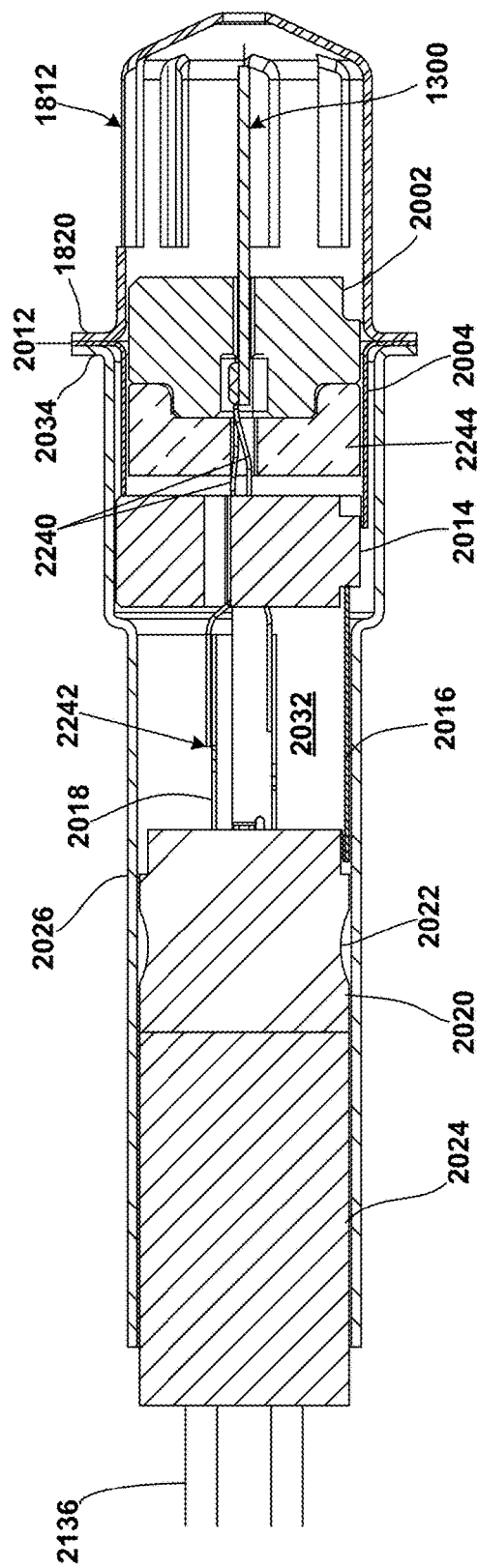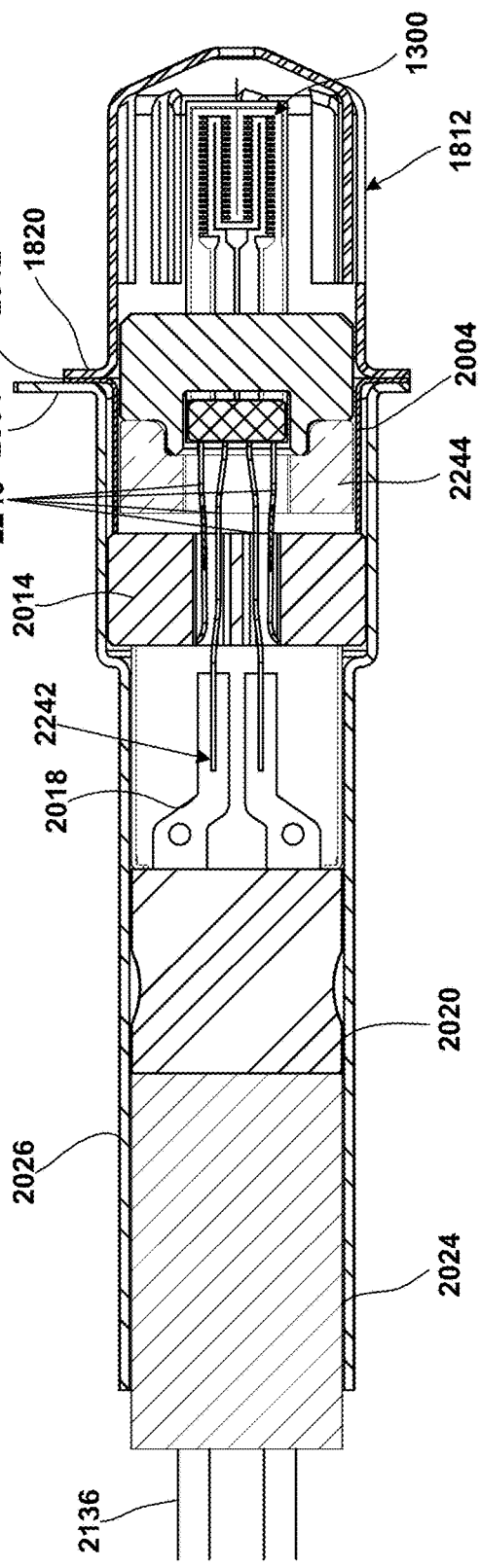
FIG. 22A
FIG. 22B

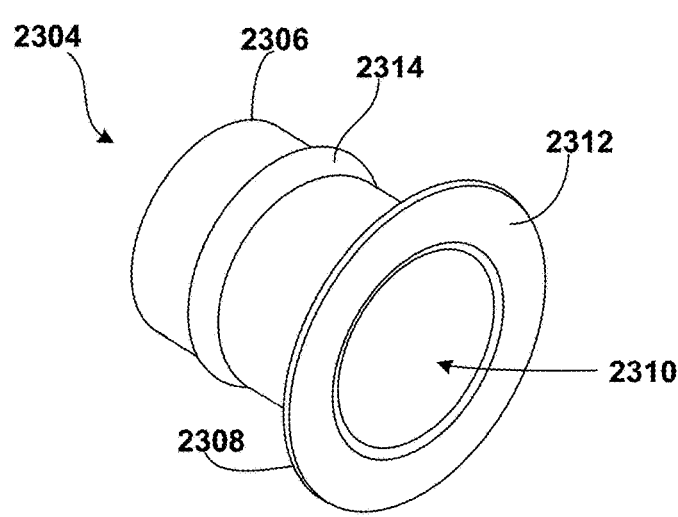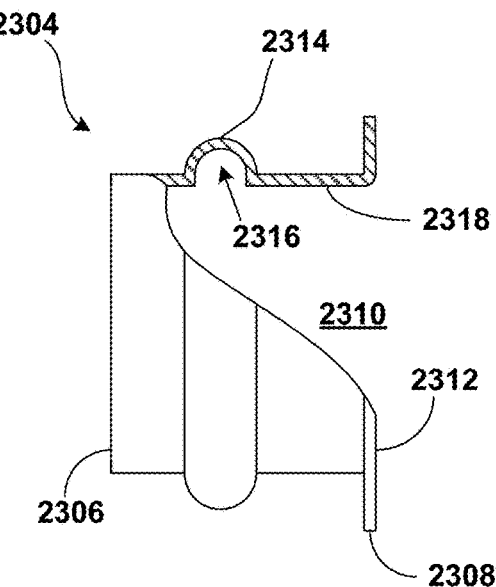
FIG. 23A    FIG. 23B
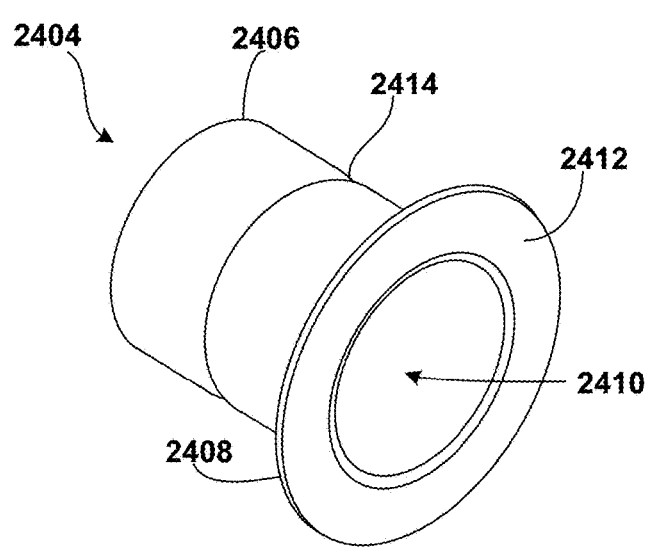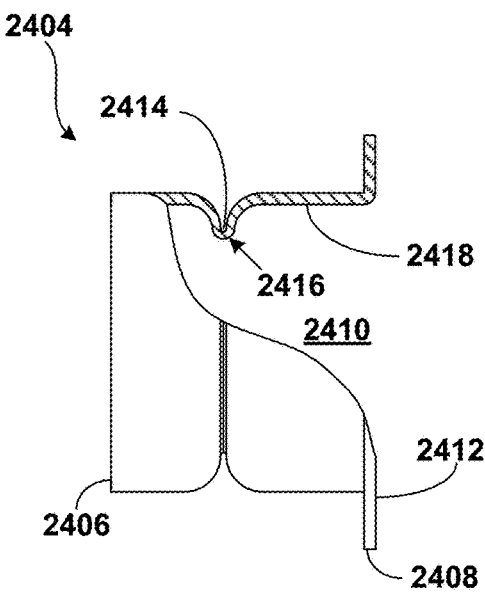
FIG. 24A    FIG. 24B

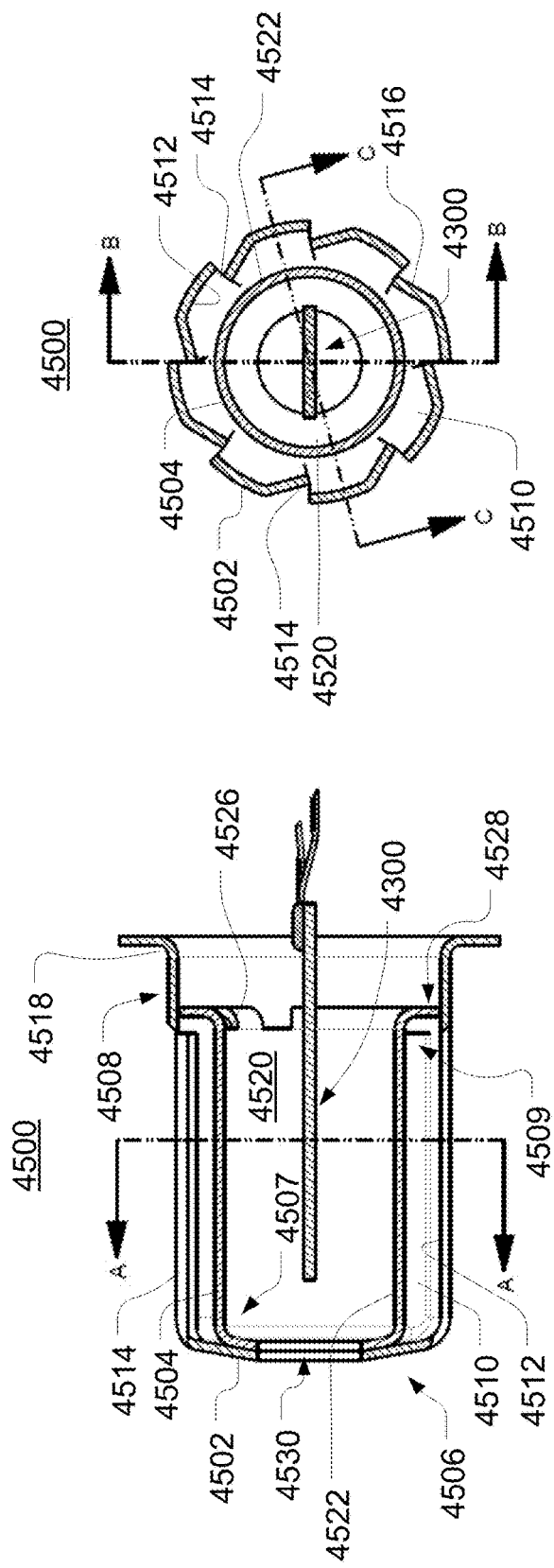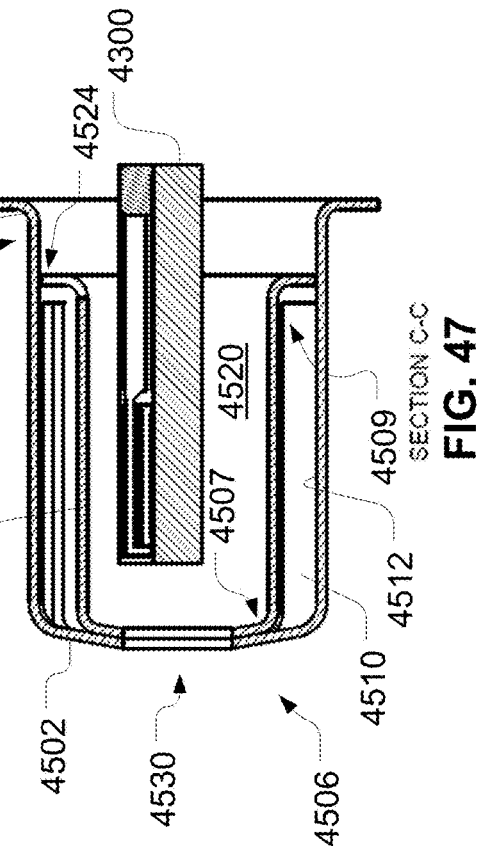

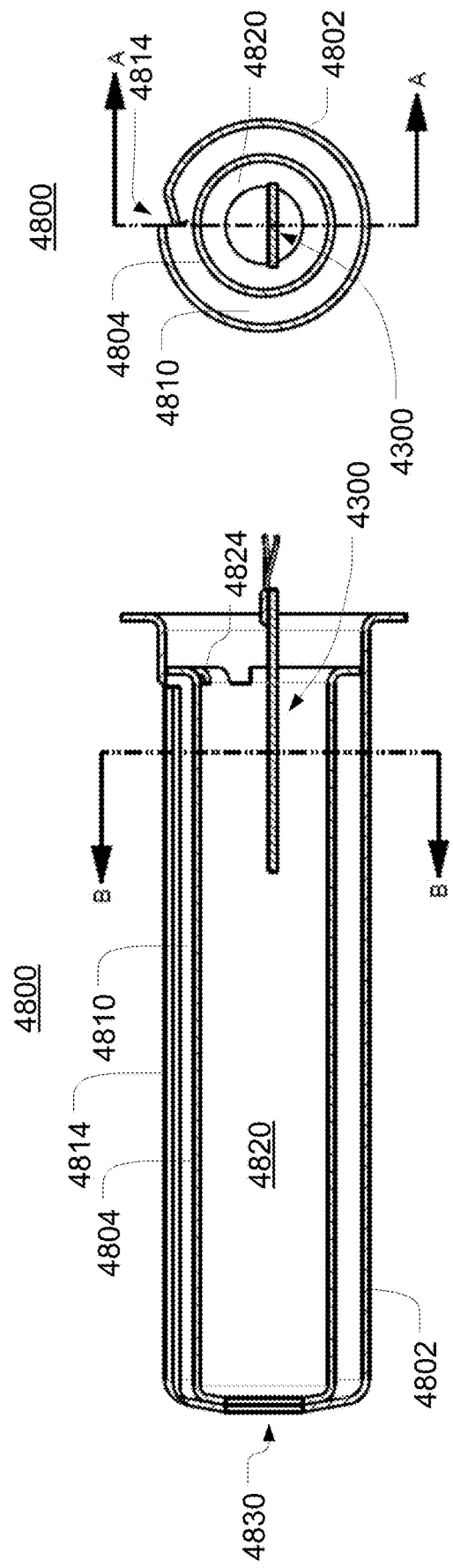

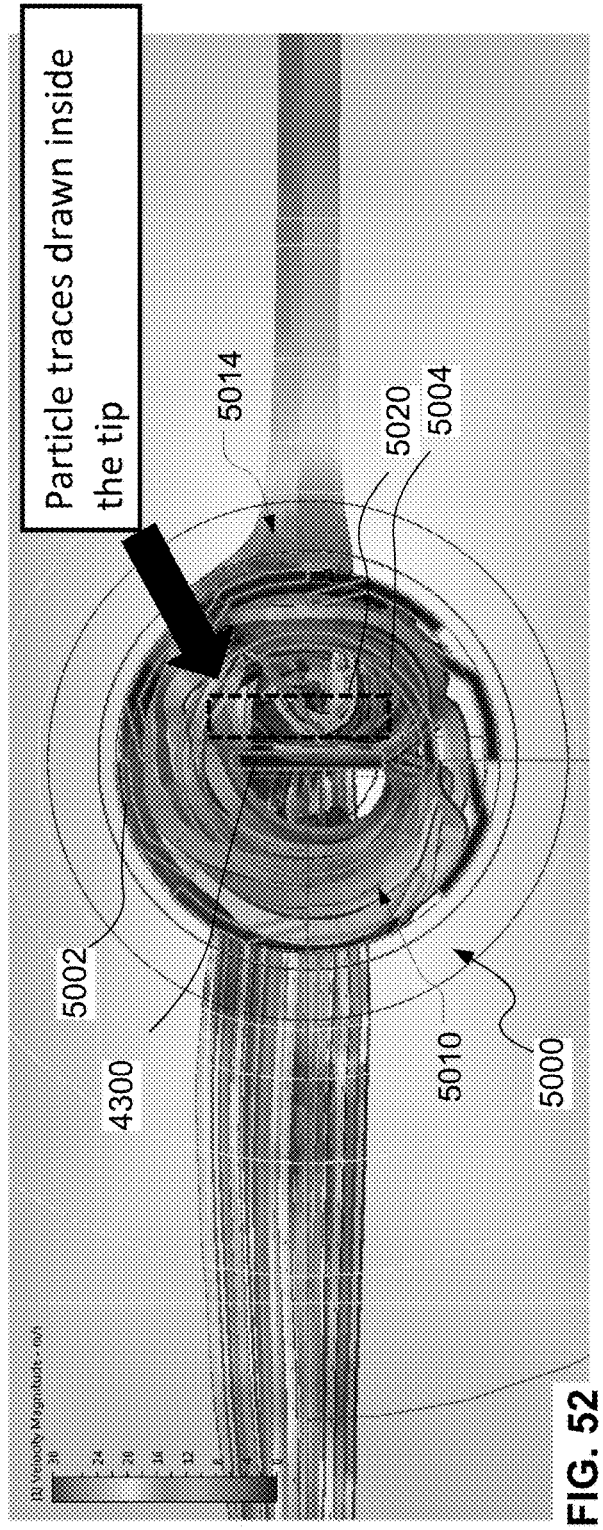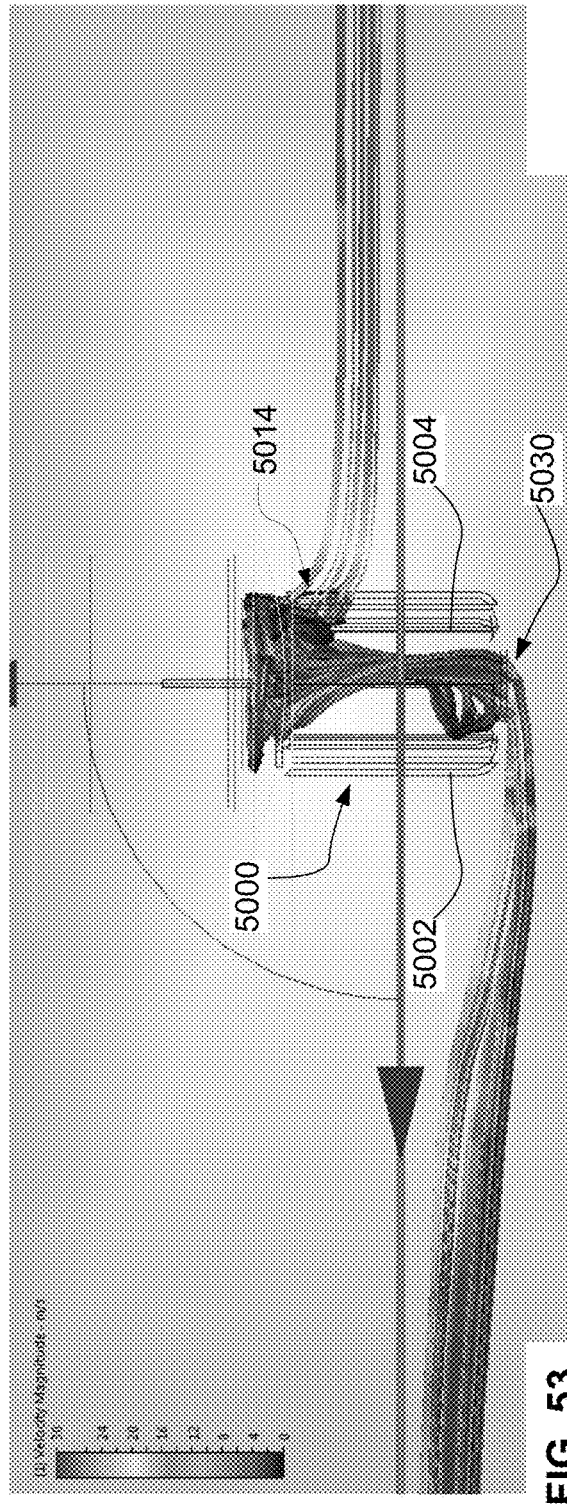
FIG. 52
FIG. 53

SOOT SENSOR SYSTEM

CROSS REFERENCE TO RELATED APPLICATIONS

This application is a continuation application of U.S. patent application Ser. No. 14/539,991 filed Nov. 12, 2014, which claims the benefit to U.S. Provisional Application Ser. No. 61/903,581, filed Nov. 13, 2013, and to U.S. Provisional Application Ser. No. 62/028,275, filed Jul. 23, 2014, all of which are fully incorporated herein by reference.

FIELD

The present disclosure relates generally to a soot sensor, and, more particularly, to a sensor system for detecting soot in an exhaust gas flow.

BACKGROUND

Soot sensors may be used in engine emissions applications, e.g. for on-board diagnostics (OBD). A sensor of this type may be used to detect and measure particulate matter build-up, e.g. soot concentration, in an engine exhaust gas. In diesel engines in particular, it is desirable to have the lowest possible soot particle concentration when exhaust gas is released into the environment. To monitor the operating status of the internal combustion engine, it is expedient for this purpose to position a soot sensor in the exhaust system associated with the internal combustion engine. The soot sensor may be positioned upstream or downstream from a diesel particulate filter (DPF). If it is positioned downstream from the DPF, function monitoring of the DPF may also be performed using the soot sensor. When the DPF fails, the soot sensor may detect excessive soot in engine exhaust and alert the vehicle engine control unit (ECU).

Soot sensors may be relatively simple resistive devices. FIG. 1 is a schematic top view of one known configuration of a soot sensor having an on-board heater element, and FIG. 2 is a schematic bottom view of the soot sensor of FIG. 1. The sensor 100 may include a non-conductive substrate 102 defining a first surface 104 and a second surface 106 opposite the first surface 104. A sense element 108 is formed on the first surface 104 of the substrate 102, and includes a conductive material defining a first electrode 110 and a separate second electrode 112. The conductive material may be a precious metal selected to withstand high temperatures, and the first 110 and second 112 electrodes may be electrically separate from each other to establish an open circuit therebetween.

As shown, the first and second electrodes 110, 112 may be configured with inter-digitized "fingers" that maximize a perimeter between the first and second electrodes 110, 112. The first electrode 110 defines a first set of fingers 114 and the second electrode 112 defines a separate second set of fingers 116. In operation, when soot (not shown) from exhaust lands on the sensing element 108, carbon in the soot electrically connects the first and second electrodes 110, 112, effectively lowering the resistance therebetween. The resistance between the electrodes is measured as an indication of the amount of soot present.

FIG. 3 is an enlarged sectional view of the soot sensor of FIGS. 1 and 2 taken along line 3-3. As shown in FIGS. 2 and 3, in some applications, the sensor 100 will also have an on-board heater element 118 implemented on the second surface 106 of the substrate 102. The on-board heater element 118 is configured to heat the soot sensor 100 through resistive heating. For example, it may be desirable to clean off soot that has collected on the first and/or second surfaces 104, 106 of the substrate 102. The on-board heater element 118, which may include a platinum trace with a known resistance, may be activated, heating the sensor element 108 to a relatively high temperature, e.g. 650° C., thereby causing any accumulated soot particles to incinerate.

A soot sensor of the type described above is susceptible to breakdown under the conditions existing in the exhaust system. The electrodes are directly subjected to exhaust gas flow, wherein certain exhaust materials may lead to corrosion of the electrodes and/or contamination of the sensor surface, which may have an interfering effect on soot accumulation measurement. Additionally, the sense element of current soot sensors lacks diagnostic functions capable of sensing a break in the sense element traces. Moreover, on-board heaters included in current soot sensors have difficulty reaching high temperatures required to sufficiently incinerate accumulated soot during high flow conditions.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

FIG. 22A is a sectional view of the soot sensor assembly of FIG. 21 taken along lines A-A;

FIG. 22B is a section view of the soot sensor assembly of FIG. 21 taken along lines B-B;

FIGS. 23A-23B are perspective and sectional views of one embodiment of a portion of the soot sensor assembly of FIG. 20;

FIGS. 24A-24B are perspective and sectional views of another embodiment of a portion of the soot sensor assembly of FIG. 20;

FIGS. 45-47 are various views of a soot sensor tip assembly consistent with the present disclosure;

FIGS. 48-49 are various views of another embodiment of a soot sensor tip assembly consistent with the present disclosure;

FIGS. 50-53 illustrate computational fluid dynamic (CFD) simulations results for a soot sensor tip assembly consistent with FIGS. 45-49;

DETAILED DESCRIPTION

The present disclosure is generally directed to soot sensors and a soot sensor system for detecting soot particles. In general, a soot sensor system consistent with the present disclosure includes a substrate defining a first surface and a second surface opposing the first surface. At least one element having at least one continuous loop of conductive material is disposed on the first surface of the substrate. The at least one element is configured to operate in a first mode to sense accumulation of soot on at least said first surface of said substrate and to operate in a second mode to remove accumulated soot on at least said first surface of said substrate. First and second electrical contacts are disposed at opposite ends of the at least one element. Circuitry is electrically coupled to the first and second electrical contacts and configured to determine an amount of soot accumulated on the first surface of the substrate and the element and to control heating of the element in response to soot accumulation.

A soot sensor and/or soot sensor system consistent with the present disclosure may be configured to be positioned in an exhaust system of a motor vehicle having a diesel engine. Additionally, a soot sensor and/or soot sensor system may be configured for use in the field of household technology in an oil heating system, for example, it being provided with an appropriately designed support depending on the application. For use in an exhaust system of a motor vehicle, a soot sensor system consistent with the present disclosure may be configured to detect soot accumulation from exhaust gas flow. Additionally, the soot sensor system may be coupled to and configured to communicate with an onboard diagnostics system of a vehicle. Additionally, the soot sensor may be positioned downstream from a diesel particulate filter (DPF) of a motor vehicle having a diesel engine, wherein the sensor may be configured to monitor the performance of the DPF.

Figure 1:
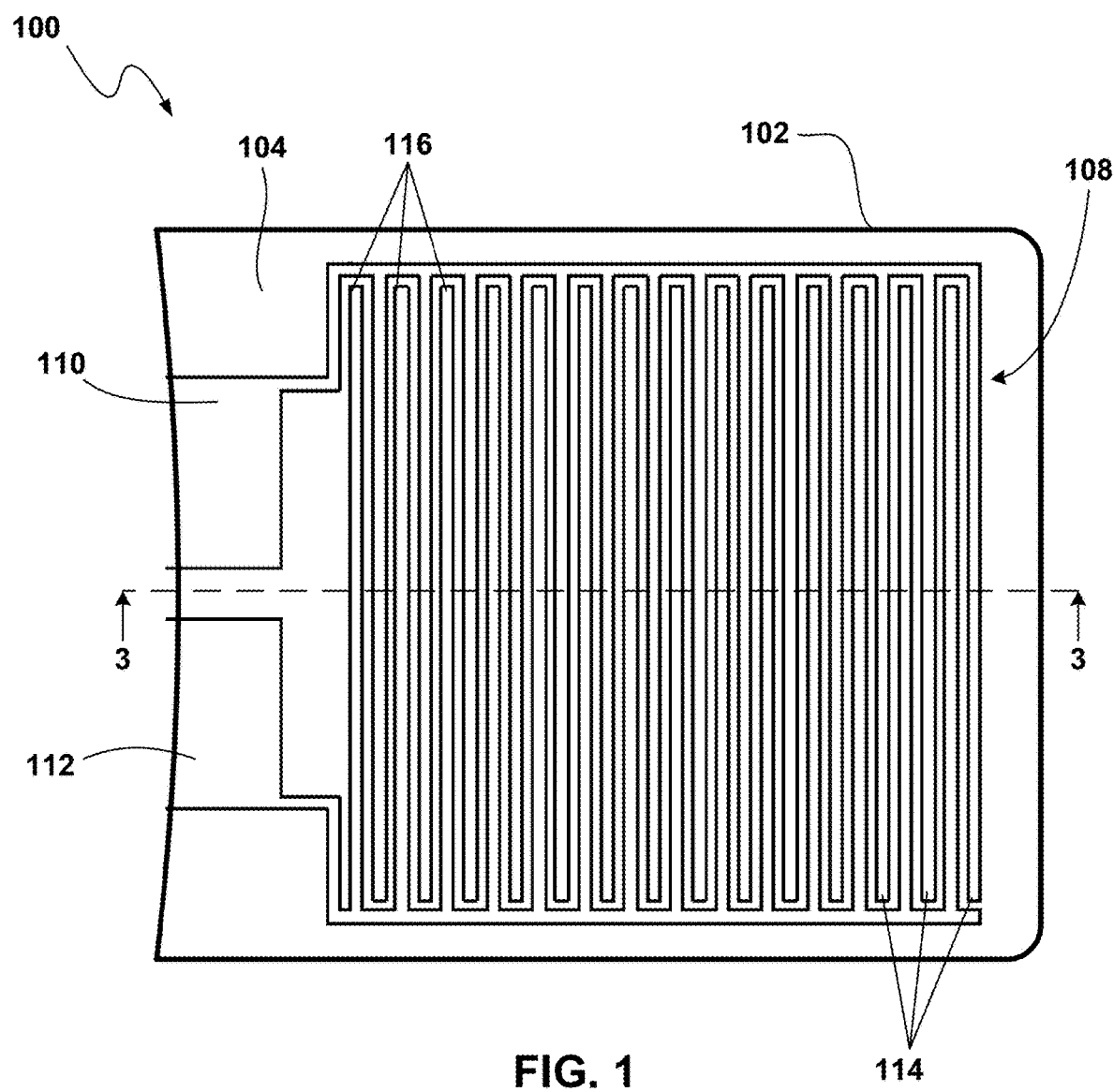
FIG. 1 is a schematic top view of a soot sensor.
Figure 2:
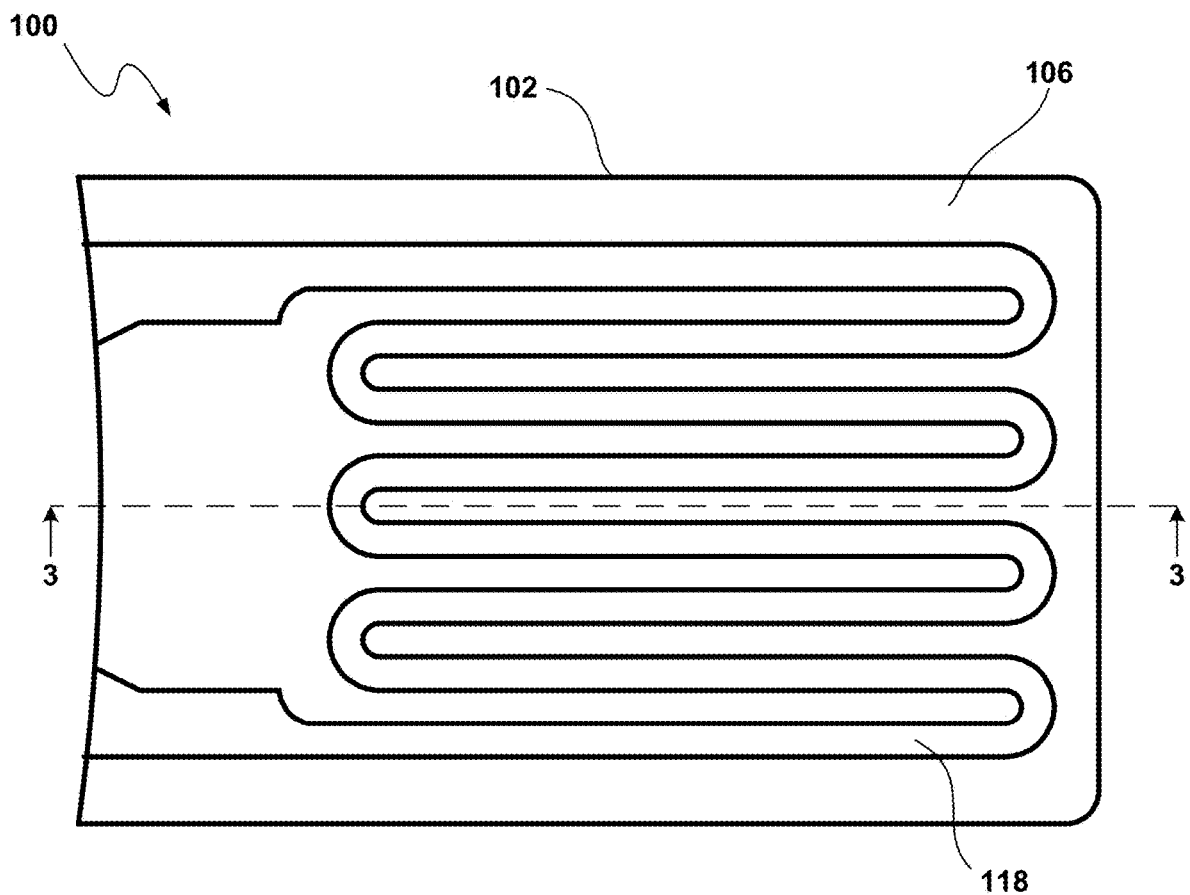
FIG. 2 is a schematic bottom view of the soot sensor of FIG. 1.
Figure 3:
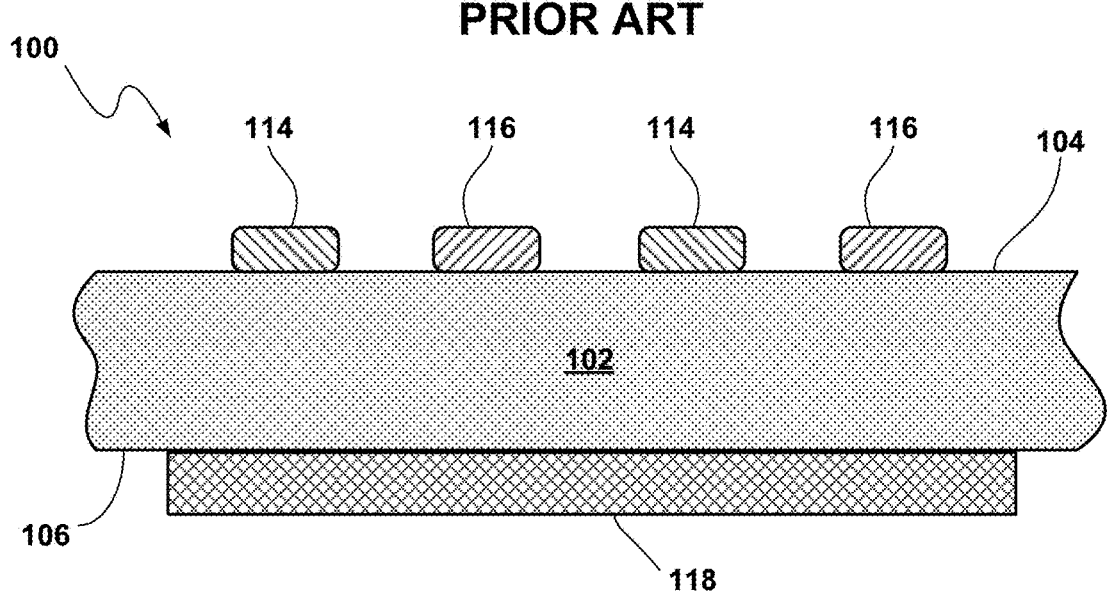
FIG. 3 is an enlarged sectional view of the soot sensor of FIGS. 1 and 2 taken along line 3-3.
Figure 4:
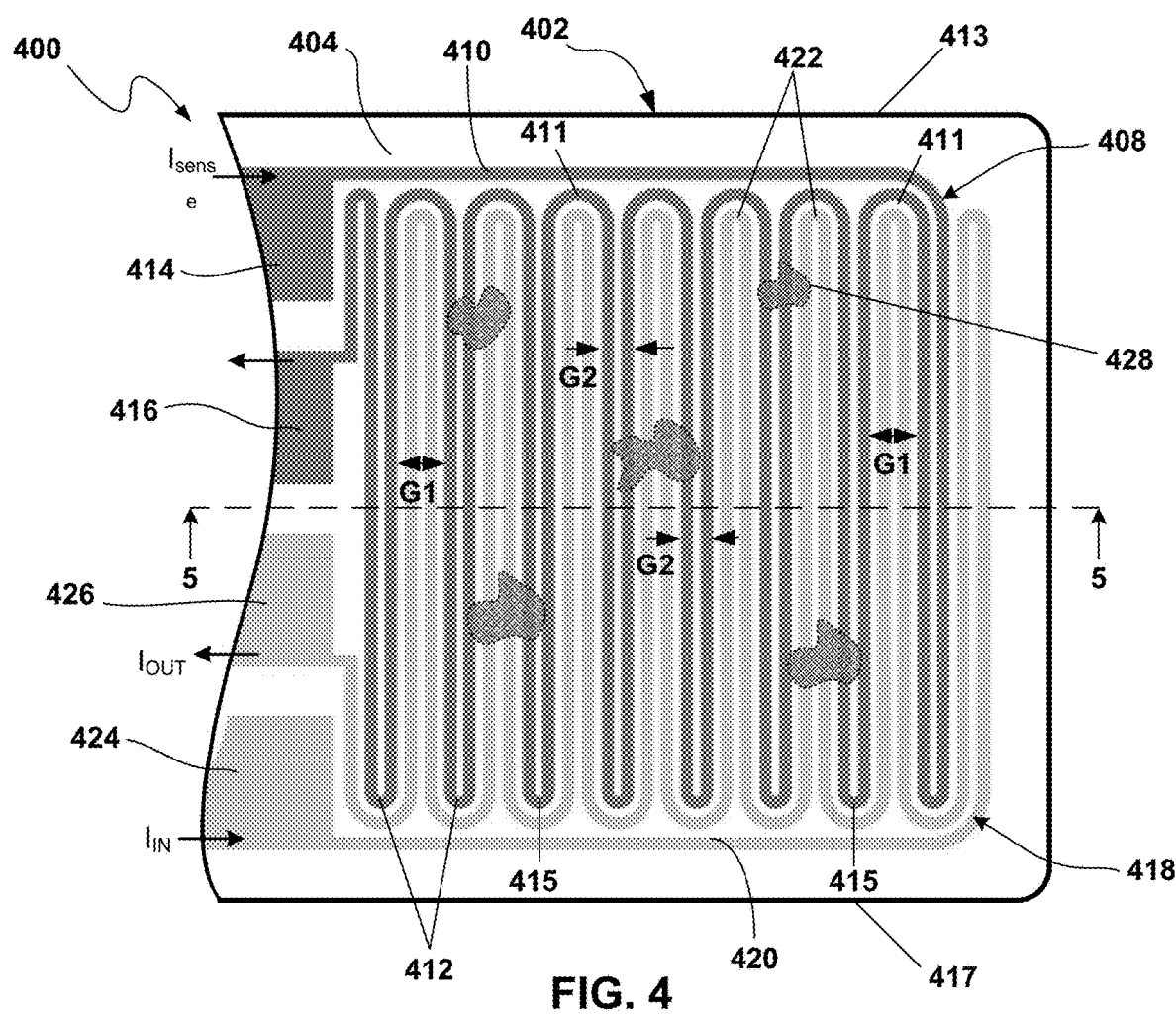
FIG. 4 is a schematic top view of a soot sensor consistent with the present disclosure.
Figure 5A:
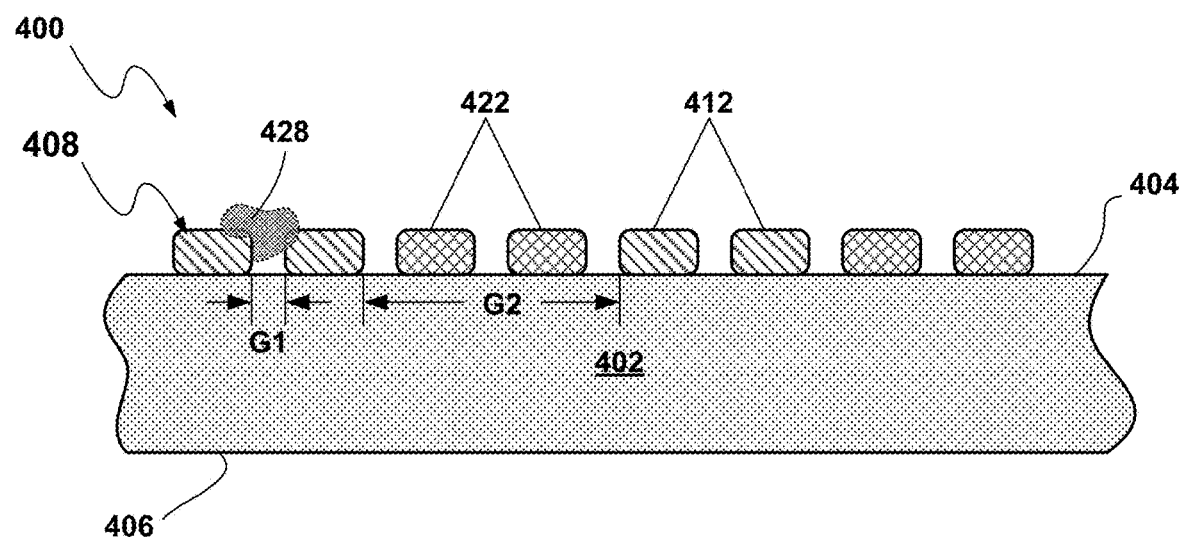
FIG. 5A is a sectional view of a portion of the soot sensor of FIG. 4 taken along line 5-5 consistent with the present disclosure.

Referring to FIG. 4, an embodiment of a soot sensor consistent with the present disclosure is schematically depicted. The soot sensor 400 includes a substrate 402, e.g. constructed from a dielectric or non-conductive material, defining a first surface 404 (e.g. a top surface, as shown in FIG. 5A) and a second surface 406 (e.g. a bottom surface, as shown in FIG. 5A) opposing the first surface 404. The soot sensor 400 includes a sensor element 408 formed on the first surface 404 of the substrate 402. The sensor element 408 includes at least one continuous loop 410 of conductive material disposed on the substrate 402. The loop 410 may take any regular and/or irregular geometric shape, e.g. serpentine, spiral, rectangular, circular, etc.

In the illustrated exemplary embodiment, the loop 410 is arranged in a serpentine configuration including a first set of a plurality of undulations 412 and a plurality of gaps G1 and G2 defined within and between each of the plurality of undulations 412. In the illustrated embodiment, the portions of the loop 410 including turns 411 adjacent the side 413 of the sensor are separated by gaps G1 and the portions of the loop 410 including turns 415 adjacent the side 417 of the sensor are separated by gaps G2, and the gaps G1 are wider than the gaps G2. The term "serpentine" as used herein refers to a configuration including turns of any shape, e.g. arcuate as show in FIG. 4, square, combinations of arcuate and square etc. and also includes turns separated by gaps of uniform and/or differing sizes.

The sensor element 408 further includes first and second electrical contacts 414, 416 at opposite ends of the loop 410. The first and second electrical contacts 414, 416 may be configured for coupling to circuitry for providing current through the loop 410. In the illustrated embodiment, an input current $I_{sense}$ may be provided at the first electrical contact 414 (or second electrical 416 contact).

The value of $I_{sense}$ may be representative of the amount of soot disposed on the sensor 400. In the illustrated embodiment, for example, soot particles 428 are shown as accumulated on the first surface 404 of the substrate 402, including on the sensor element 408. As soot 428 builds up on the sensor element, the resistance of the loop 410 changes, which changes the value of $I_{sense}$ The value of $I_{sense}$ is thus representative of the amount of soot accumulated on the sensor.

The sensor element 400 further include a heater element 418 formed on the first surface 404 of the substrate 402. The heater element 418 includes at least one continuous loop 420 of conductive material disposed on the substrate 402. The loop 420 may take any regular and/or irregular geometric shape, e.g. serpentine, spiral, rectangular, circular, etc, and may be positioned adjacent the sensor element loop 410 in at least a portion of its length.

In the illustrated exemplary embodiment, the loop 420 is arranged in a serpentine configuration including a second set of a plurality of undulations 422 complementary to and interweaving with the first set of plurality of undulations 412. The heater element 418 further includes first and second electrical contacts 424, 426 at opposite ends of the loop 420. The first and second electrical contacts 424, 426 may be configured for coupling to circuitry for providing current through the loop 420. In the illustrated embodiment, an input current $I_{heater}$ may be provided at the first electrical contact 424 (or second electrical 426 contact). In one embodiment, for example, when a threshold amount of soot 428 accumulates on the sensor element 408, e.g. as determined by reaching a threshold value of $I_{sense}$, the heater current $I_{heater}$ may be applied to cause the heater element 418 to heat and at least partially remove, e.g. incinerate, the soot 428, thereby cleaning/regenerating the sensor 400 for continued use.

The sensor element 408 may include electrically conductive materials or metals, such as, gold, platinum, osmium, rhodium, iridium, ruthenium, aluminum, titanium, zirconium, and the like, as well as, oxides, alloys, and combinations including at least one of the foregoing metals. The heater element 418 may include various materials. For example, materials may include platinum, gold, palladium, and the like and/or alloys, oxides, and combinations thereof. The substrate 402 may include a non-conductive and/or electrically insulating materials. Materials may include oxides, including, but not limited to, alumina, zirconia, yttria, lanthanum oxide, silica, and/or combinations including at least one of the foregoing, or any like material capable of inhibiting electrical communication and providing structural integrity and/or physical protection. Additionally, the soot sensor 400 may include thick film and/or thin film constructions.

FIG. 5A is a sectional view of a portion of the soot sensor 400 of FIG. 4 taken along line 5-5 consistent with one embodiment of the present disclosure. In the illustrated embodiment, soot particles 428 are accumulated on at least the sensor element 408. In particular, when exposed to exhaust gas flow, the soot particles 428 may accumulate within at least one of the plurality of gaps G1 and/or G2 defined within and between each of the plurality of undulations 412 of the loop 410 of the sensor element 408. When the sensor element 408 is free of any soot particles, the electrical circuit of the sensor element 408 created between the first and second electrical contacts 414, 416 has a first resistance. When soot particles 428 accumulate on the sensor element 408, and, in particular, within at least one of the plurality of gaps G1 and/or G2, wherein the soot particle 428 makes contact with the loop 410, the resistance between the first and second electrical contacts 414, 416 may change. Resistance may increase as more soot particles 428 collect and accumulate. The heater element 418 may be activated when it is desired to have accumulated soot particles 428 removed from the soot sensor 408. The heater element 418 may be configured to reach a temperature at which soot particles 428 are incinerated.

Figure 5B:
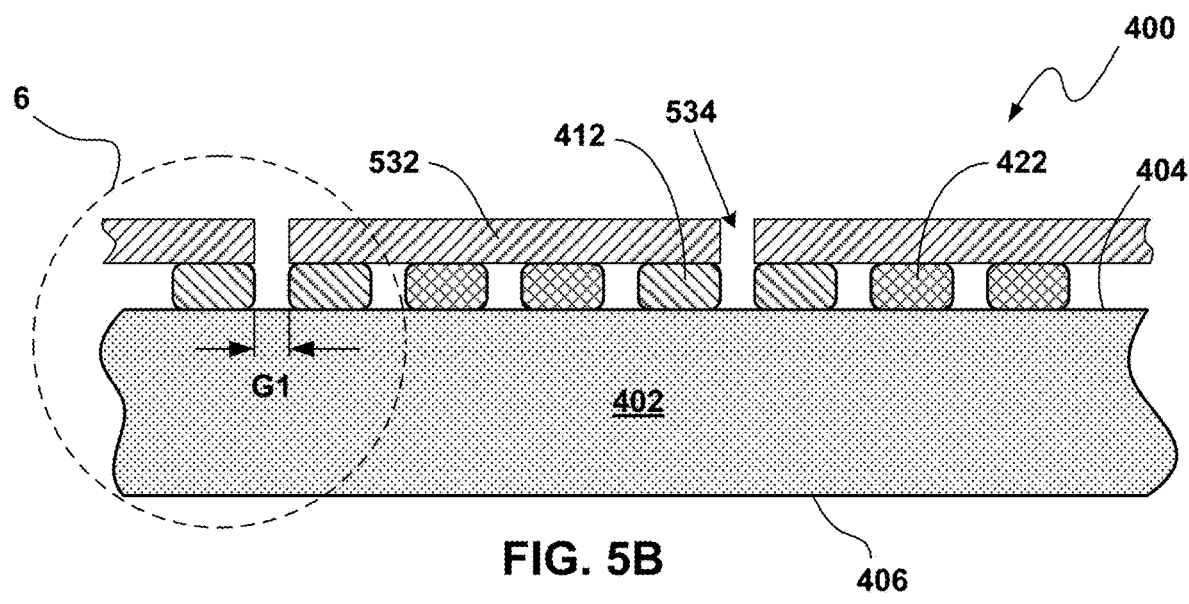
FIG. 5B is a sectional view of a portion of the soot sensor of FIG. 4 taken along line 5-5 according to another embodiment consistent with the present disclosure.
Figure 6:
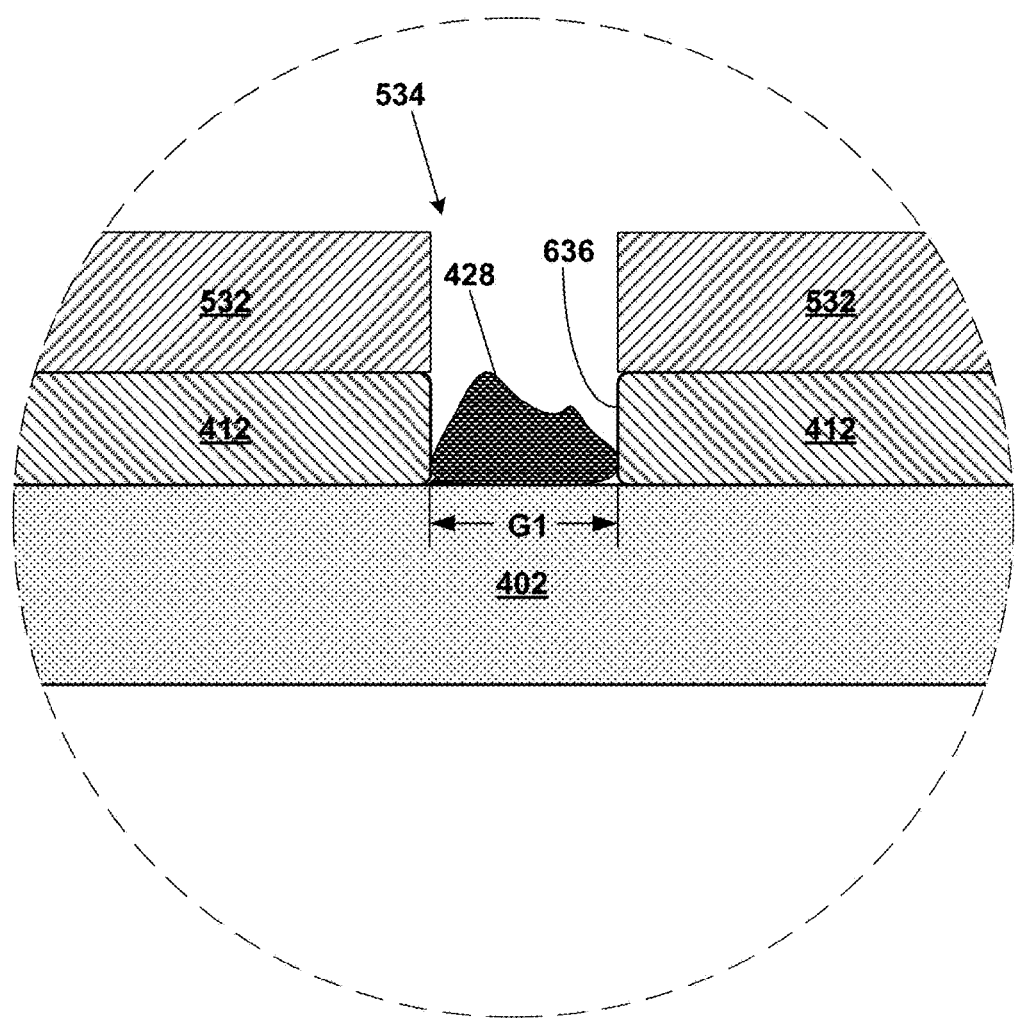
FIG. 6 is an enlarged view of the portion of the soot sensor of FIG. 5B.

FIG. 5B is a sectional view of a portion of the soot sensor of FIG. 4 taken along line 5-5 according to another embodiment consistent with the present disclosure and FIG. 6 is an enlarged view of a portion of the soot sensor of FIG. 5B. In one embodiment, a protective layer 532 is formed over the first surface 404 of the substrate 402 and covers at least a portion of the undulations 412, 422 of the sensor and heater elements 408, 418, respectively. The protective layer 532 may be configured to insulate at least a portion of the undulations 412 of the sensor element 408 from exhaust gas flow. The protective layer 532 further defines a plurality of channels 534 corresponding to and aligned with the plurality of gaps G1 defined by the undulations 412 of sensor element 408.

Referring to FIG. 6, each of the plurality of channels 534 exposes at least a portion of the sensor element, e.g. edges 636 of the undulations 412, to exhaust gas flow and the soot particles 428. In the illustrated embodiment, each of the plurality of channels 534 are sized and/or shaped to allow soot particles 428 to accumulate within at least one of the plurality of channels 534 and the corresponding gap G1, such that soot particles 428 make contact with at least a portion of the exposed sensor element 408 conductive material, e.g. edges 636 of the undulations 412.

Figure 7:
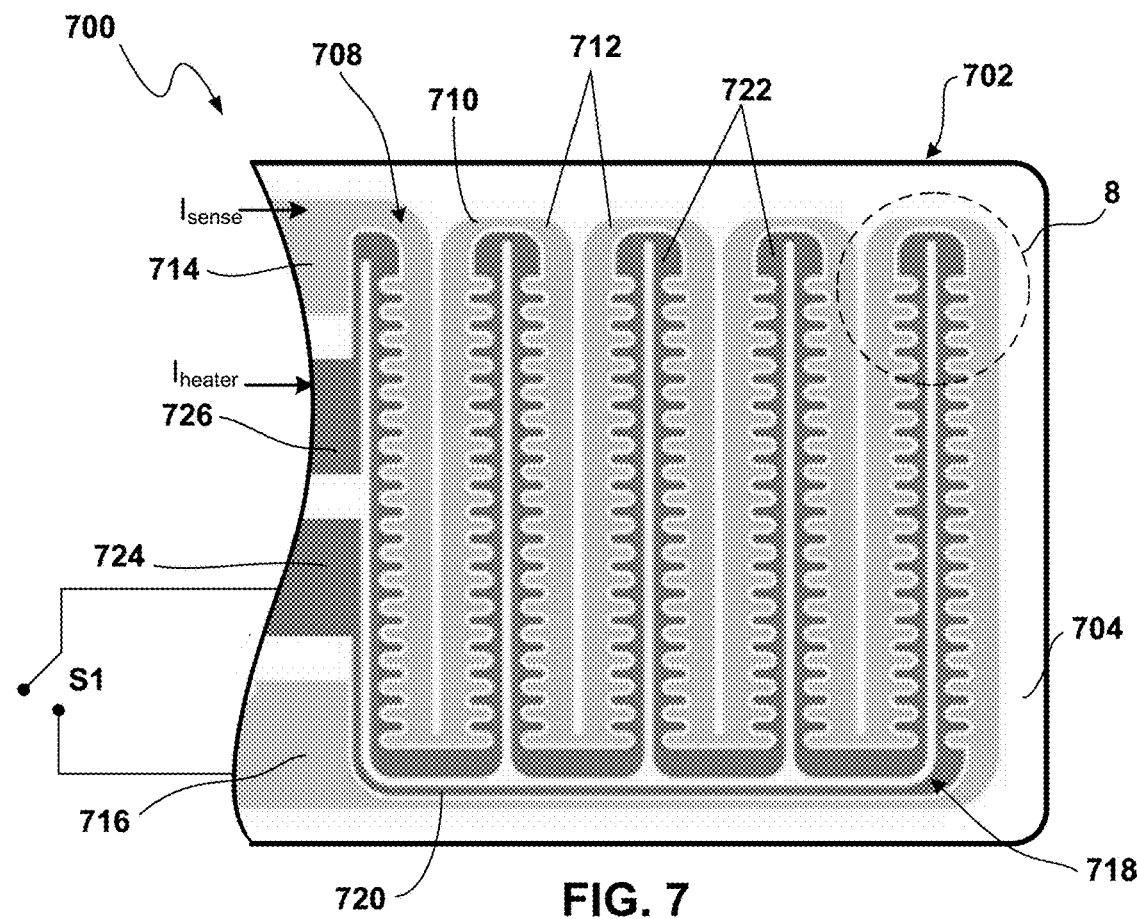
FIG. 7 is a schematic top view of another embodiment of a soot sensor consistent with the present disclosure.
Figure 8A:
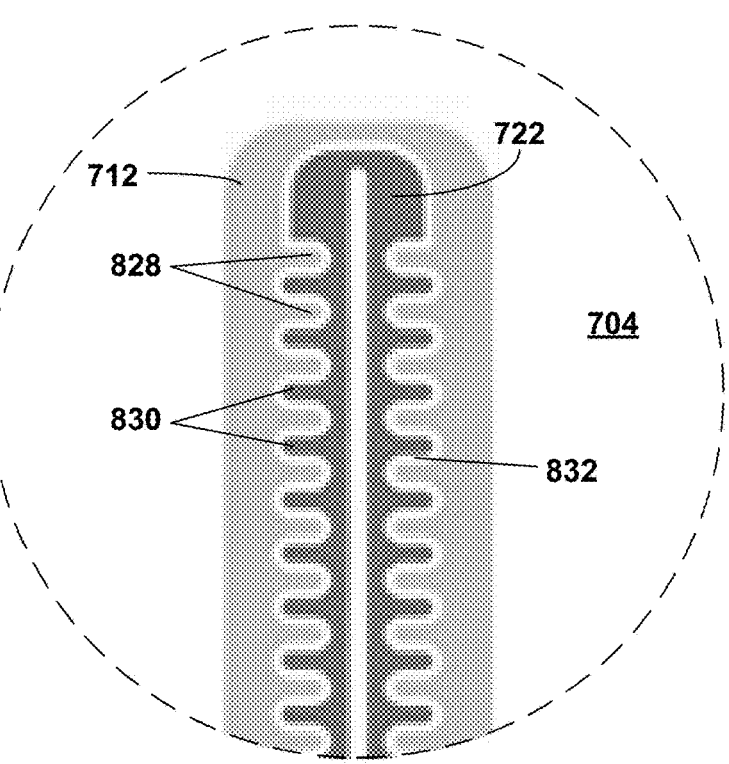
FIG. 8A is an enlarged view of a portion of the soot sensor of FIG. 7.

FIG. 7 is a schematic top view of another embodiment of a soot sensor consistent with the present disclosure and FIG. 8A is an enlarged view of a portion of the soot sensor of FIG.

7. This embodiment is similar to the embodiment of FIG. 4, and like components have been assigned like reference numerals in the seven hundreds rather than the four hundreds. The soot sensor 700 includes a substrate 702 defining a first surface 704. A sensor element 708 and a heater element 718 are formed on the first surface 704. The sensor and heater elements 708, 718 each include at least one continuous loop of conductive material 710, 720, respectively, disposed on the substrate 702. Similar to the embodiment of FIG. 4, the loops 710, 720 may be arranged in a serpentine configuration including first 712 and second 722 sets of undulations. Referring to FIG. 8A, the first 712 and second 722 sets undulations further define first 828 and second 830 subsets of undulations, respectively. A plurality of gaps 832 are defined within and between each of the first 828 and second 830 subsets of plurality of undulations.

The sensor element 708 further includes first 714 and second 716 electrical contacts at opposite ends of the loop 710. The first and second electrical contacts 714, 716 may be configured for coupling to circuitry for providing current through the loop 710. In the illustrated embodiment, an input current $I_{sense}$ may be provided at the first electrical contact 714 (or second electrical 716 contact). Similarly, the heater element 718 further includes first 724 and second 726 electrical contacts at opposite ends of the loop 720. The first and second electrical contacts 724, 726 may be configured for coupling to circuitry for providing current through the loop 720. In the illustrated embodiment, an input current $I_{heater}$ may be provided at the first electrical contact 724 (or second electrical 726 contact).

In the illustrated embodiment, the sensor and heater elements 708, 718 may be configured to be operated separately and independently from one another as described above regarding the embodiment of FIG. 4. Additionally, the soot sensor 700 may further include a switch S1 coupled to the first 724 and second 716 electrical contacts of the heater 718 and sensor 708 elements, respectively, for selectively coupling and decoupling the contacts 724, 716. When the switch S1 is open, the sense current $I_{sense}$ is determined by the resistance of the associated with the loop 710 of conductive material between contacts 714 and 716 and varies with soot particles deposited on the loop 710, thereby allowing the sensor element to sense soot particles. When the switch S1 is closed, loops 710 and 720 are electrically coupled in series establishing a single continuous loop of conductive material between the contacts 714 and 726. The current $I_{sense}$ may then pass through both the sensor 708 and heater 718 elements to allow both the sensor 708 and heater 718 elements to act as a single heater element.

Figure 8B:
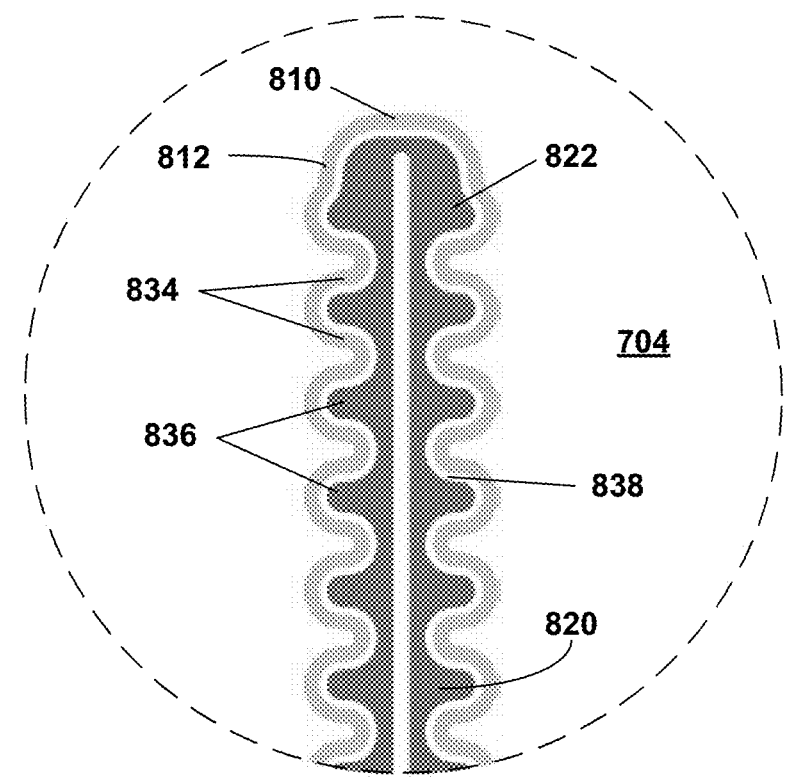
FIG. 8B is an enlarged view of a portion of the soot sensor of FIG. 7 according to another embodiment consistent with the present disclosure.

FIG. 8B is an enlarged view of a portion of the soot sensor of FIG. 7 according to another embodiment consistent with the present disclosure. In the illustrated embodiment, the sensor and heater elements 708, 718 include continuous loops 810, 820 of conductive material disposed on the first surface 704. The loops 810, 820 are arranged in a serpentine configuration including first and second sets of a plurality of undulations 812, 822. The first and second sets of plurality of undulations 812, 822 further define first and second subsets of plurality of undulations 834, 836, respectively. A plurality of gaps 838 are defined within and between each of the first and second subsets of plurality of undulations 834, 836, wherein the gaps 838 are substantially uniform in size and/or shape.

In the illustrated embodiment, the loop 810 is substantially narrower in width than the loop 710 shown in FIG. 8A, thereby increasing the resistance of loop 810 to a value greater than the resistance of loop 710. An increase in resistance may allow the loop 810 to be configured to sense temperature with greater accuracy than the loop 710.

Figure 8C:
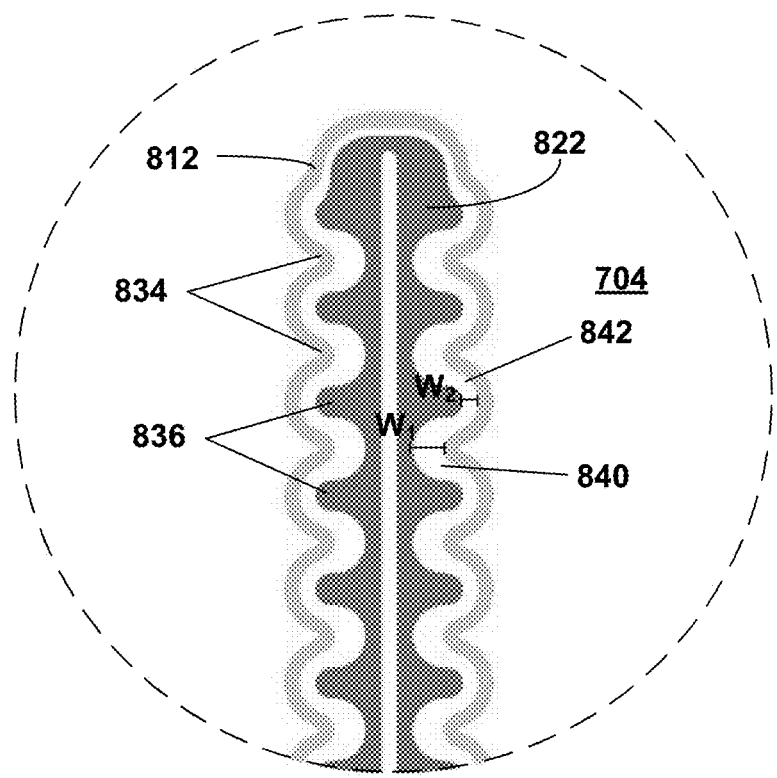
FIG. 8C is an enlarged view of the portion of the soot sensor of FIG. 7 according to another embodiment consistent with the present disclosure.

FIG. 8C is an enlarged view of a portion of the soot sensor of FIG. 7 according to another embodiment consistent with the present disclosure. In the illustrated embodiment, a plurality of gaps 840, 842 are defined within and between each of the first and second subsets of plurality of undulations 834, 836, wherein the gaps 840, 842 vary in size and/or shape. For example, gap 840 has a width $W_1$ and gap 842 has a width $W_2$, wherein width $W_1$ is generally greater than width $W_2$. The gaps 840, 842 of varying size and/or shape may allow the sensor element 708 to have a wider dynamic range of response when sensing soot particle accumulation.

Figure 9:
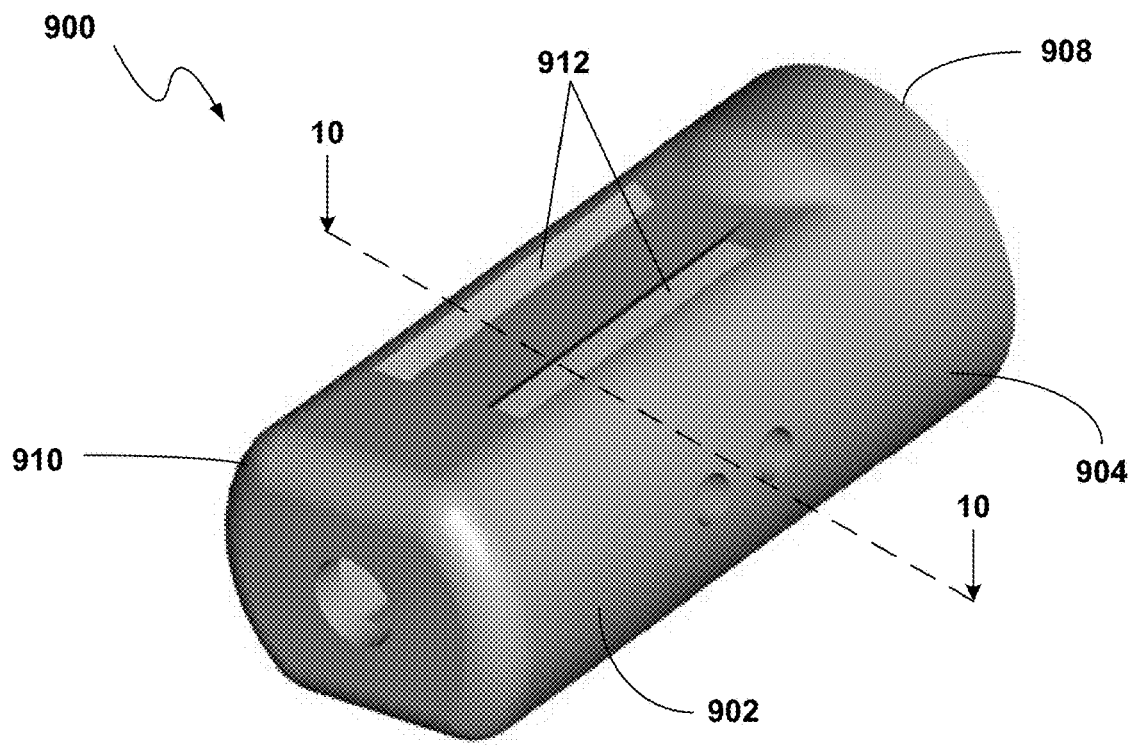
FIG. 9 is a perspective view of a soot sensor tip consistent with the present disclosure.
Figure 10:
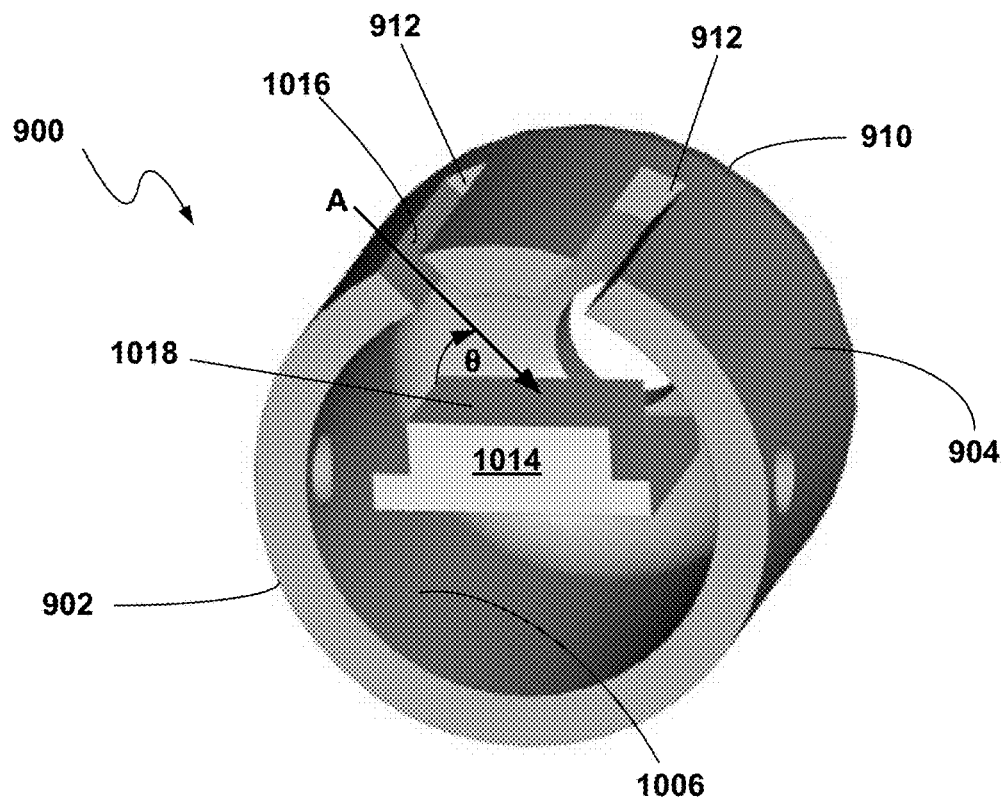
FIG. 10 is an enlarged perspective sectional view of the soot sensor tip of FIG. 9 taken along line 10-10.

FIG. 9 is perspective view of a soot sensor tip consistent with the present disclosure and FIG. 10 is an enlarged perspective sectional view of the soot sensor tip of FIG. 9 taken along line 10-10. The tip 900 is configured to at least partially enclose a soot sensor 1014, wherein the soot sensor 1014 may include embodiments consistent with the present disclosure. The tip 900 includes a body 902 having an exterior surface 904 and an interior surface 1004 and a proximal end 908 and a distal end 910. In the illustrated embodiment, the body 902 gradually transitions from a generally round shape at the proximal end 908 to a generally rectangular shape at the distal end 910. The geometry of the body 902 is configured to minimize volume on the interior of the tip 900. The body 902 defines at least one angularly disposed channel 912 defining a path 1016 from the exterior surface 904 of the body 902 to the interior surface 1006 of the body 902.

The path 1016 is configured to direct exhaust gas flow to the soot sensor 1014, and may be defined by sidewalls oriented at an angle θ of less than 90 degrees relative to the first surface 1018 of the soot sensor 1014, as indicated by the arrow A in FIG. 10. The path 1016 may thus be configured at an angle less than 90 degrees relative to the first surface 1018 to allow soot from exhaust gas flow to enter the interior of the body and impact the soot sensor 1014 at an angle less than 90 degrees relative to the first surface 1018 of the soot sensor 1014. The body 902 may define a plurality of angularly disposed channels 912 positioned along an entire circumference of the body.

Figure 11:
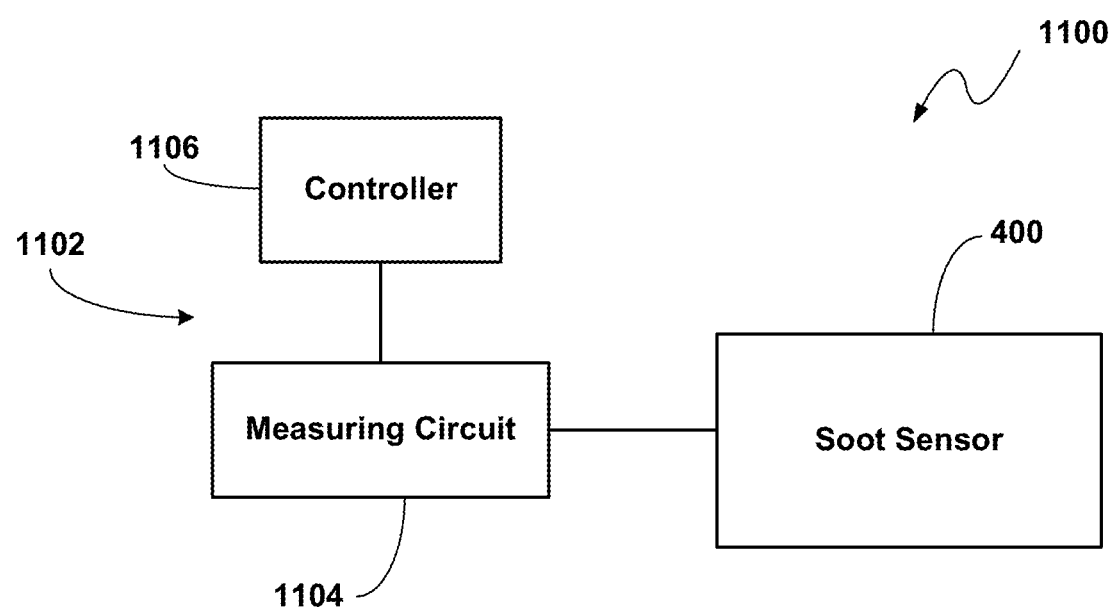
FIG. 11 is a block diagram of one exemplary embodiment of a soot sensor system consistent with the present disclosure.

FIG. 11 is a block diagram of one exemplary embodiment of a soot sensor system consistent with the present disclosure. The soot sensor system 1100 includes a soot sensor 400. For purposes of clarity and description, references will be made to the soot sensor 400 of FIG. 4. It should be noted, however, that the soot sensor system 1100 may include other embodiments of the soot sensor consistent with the present disclosure. The soot sensor system 1100 further includes circuitry 1102 electrically coupled to the soot sensor 400 and configured to provide electrical current to the soot sensor 400. In one embodiment, the circuitry 1102 may be coupled to the first and second electrical contacts 414, 416 and 424, 426 of the sensor and heater elements 408, 418, respectively, for providing currents $I_{sense}$ and/or $I_{heater}$.

The circuitry 1102 includes a measuring circuit 1104 electrically coupled and configured to communicate with a controller 1106. The measuring circuit is also electrically coupled to the soot sensor 400, e.g. to the first and second electrical contacts 414, 416 of the sensor element 408 and/or the first and second electrical contacts 424, 426 of the heater element 418. The measuring circuit 1104 may be configured to apply a voltage between first and second electrical contacts 414, 416 and provide an output to the controller 1106 representative of the resulting value of $I_{sense}$. The controller 1106 may be a known engine control unit (ECU) of an automobile and communication between the soot sensor 440, measuring circuit 1104 and the controller may be accomplished via a known CAN bus.

The value of the current $I_{sense}$ through the sensor element 408 may be utilized to determine an amount of soot that has been deposited on the soot sensor 400, which may be further indicative of an amount of soot in an exhaust stream communicating with the sensor 400. As previously noted, when soot is deposited between the first and second electrical contacts 414, 416 the electrical resistance of the conductive path between the contacts 414, 416 changes, which results in a corresponding change in $I_{sense}$. The value of $I_{sense}$ is representative of the amount of soot that has been deposited on the sensor 400.

The measuring circuit 1104 may also be configured to apply a voltage between the first and second electrical contacts 424, 426 of the heater element. When the value of $I_{sense}$ reaches a predetermined threshold, the controller 1106 may provide an output to the measuring circuit 1104 to cause the measuring circuit to activate the heater element 418 by providing a current $I_{heater}$ to the heater element 418. Upon activation of the heater element 418, the heater element 418 may heat to a temperature at which accumulated soot particles are incinerated, thereby clearing soot particles from the soot sensor 400, particularly the sensor element 408.

Additionally, the circuitry 1102 may be configured to detect open circuits and/or breaks in the sensor and/or heater elements 408, 418. For example, if the sensor element 408 has a break, the circuit between the contacts 414, 416 of the sensor element will be an open circuit or a circuit with higher-than-normal resistance. Thus, if the current $I_{sense}$ falls below a predetermined threshold, the controller 1106 may provide an output indicating failure in the sensor element.

Figure 12:
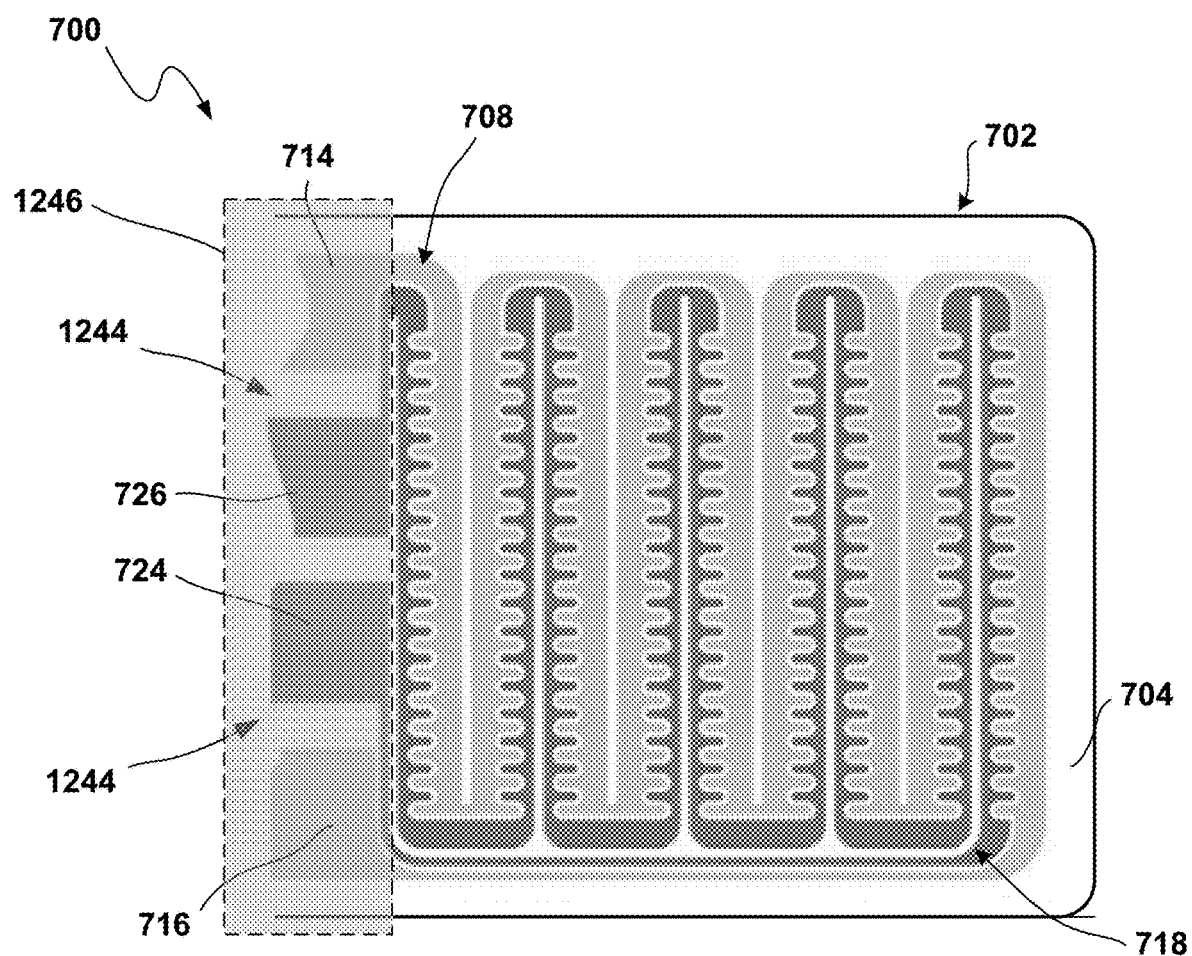
FIG. 12 is a schematic top view of the soot sensor of FIG. 7 including a passivation layer.

FIG. 12 is a schematic top view of the soot sensor of FIG. 7 including a passivation layer. In the illustrated embodiment, the soot sensor 700 may include a pad portion 1244 defining at least the first 714 and second 716 electrical contacts of the sensor element 708 and/or the first 724 and second 726 electrical contacts of the heater element 718. The soot sensor 700 may further include a passivation layer 1246 disposed on the first surface 704 of the substrate 702 and at least over the pad portion 1244. The passivation layer 1246 may be configured to inhibit and/or prevent any conduction between the first 714 and second 716 electrical contacts of the sensor element 708 and/or between the first 724 and second 726 electrical contacts of the heater element 718. Additionally, the passivation layer 1246 may be configured to inhibit and/or prevent the occurrence of high heat. The passivation layer 1246 may include non-conductive and/or electrically insulating materials. Materials may include oxides, including, but not limited to, alumina, zirconia, yttria, lanthanum oxide, silica, and/or combinations including at least one of the foregoing, or any like material capable of inhibiting electrical communication. Additionally, the passivation layer 1246 may include materials configured to provide thermal insulation. In the illustrated embodiment, the passivation layer 1246 may include a thick film glass.

Figure 13:
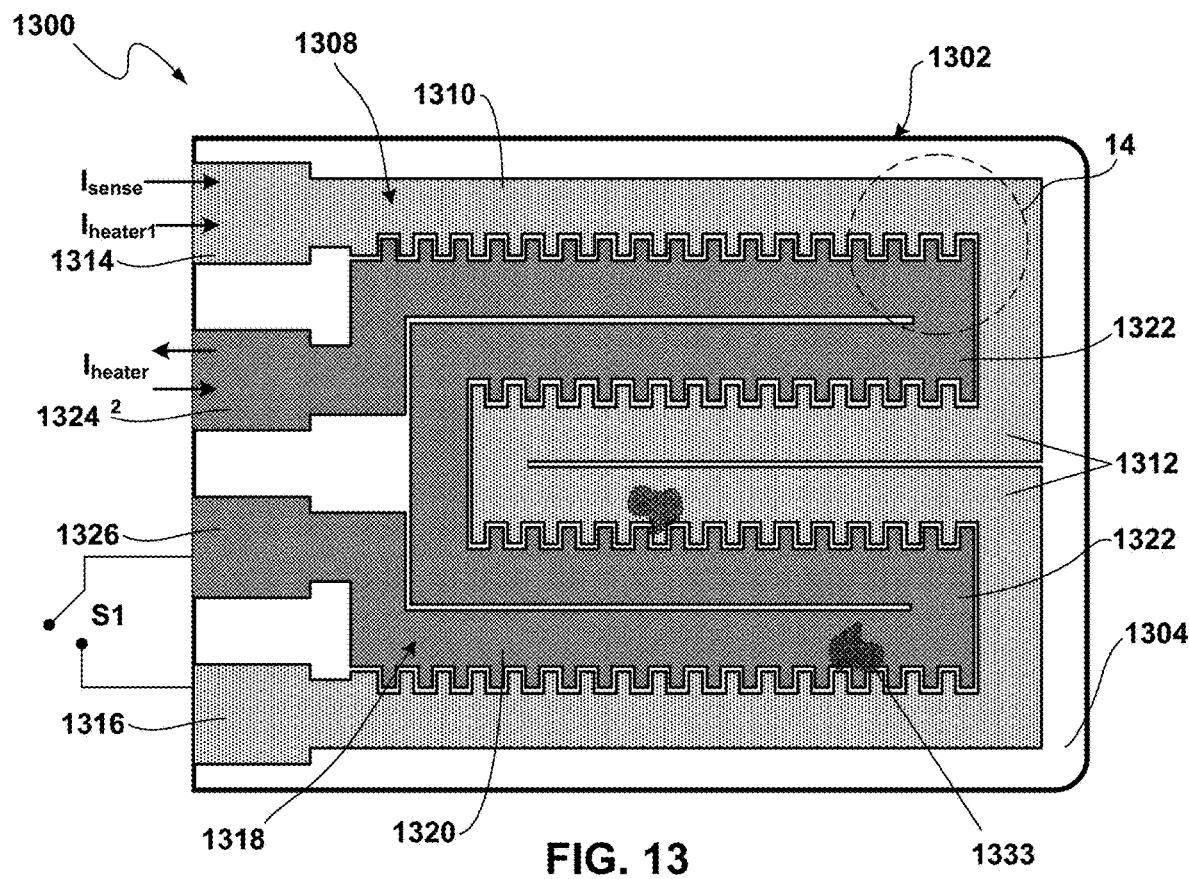
FIG. 13 is a schematic top view of another embodiment of a soot sensor consistent with the present disclosure.
Figure 14:
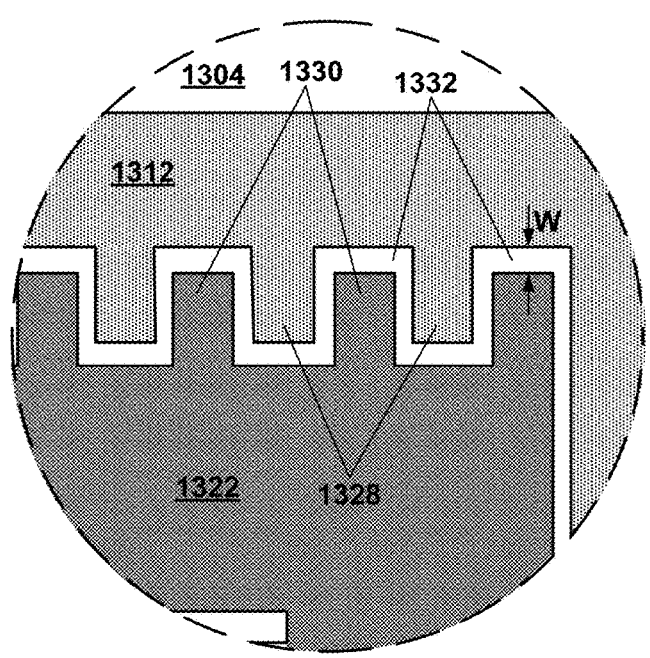
FIG. 14 is an enlarged view of a portion of the soot sensor of FIG. 13.

FIG. 13 is a schematic top view of another embodiment of a soot sensor 1300 consistent with the present disclosure and FIG. 14 is an enlarged view of a portion of the soot sensor 1300 of FIG. 13. This embodiment is similar to the embodiment of FIG. 4, and like components have been assigned like reference numerals in the thirteen hundreds rather than the four hundreds. The soot sensor 1300 includes a substrate 1302 defining a first surface 1304 (e.g. a top surface, similar to first surface 404 of soot sensor 400) and a second surface (not shown) (e.g. a bottom surface, similar to second surface 406 of soot sensor 400) opposing the first surface 1304. A first sensor/heater element 1308 and a second sensor/heater element 1318 are formed on the first surface 1304. As described in greater detail herein, the first and second sensor/heater elements 1308, 1318 may each be configured to sense soot accumulation in a similar manner as the sensor element 408 shown in FIG. 4. Additionally, the first and second sensor/heater elements 1308, 1318 may each be configured to heat and at least partially remove, e.g. incinerate, accumulated soot, thereby cleaning/regenerating the sensor 1300 for continued use.

The first and second sensor/heater elements 1308, 1318 each include at least one continuous loop of conductive material 1310, 1320, respectively, disposed on the substrate 1302. Similar to the embodiment of FIG. 4, the loops 1310, 1320 may be arranged in a serpentine configuration including first and second sets of undulations 1312, 1322, respectively. Referring to FIG. 14, the first and second sets of undulations 1312, 1322 further define first 1328 and second 1330 subsets of undulations, respectively. A plurality of gaps 1332 are defined within and between each of the first 1328 and second 1330 subsets of plurality of undulations. As shown, the gaps 1332 may have a substantially uniform size and/or shape. In the illustrated embodiment, the gaps 1332 may have a width W. The width W of the gaps 1332 may range from 10 microns to 100 microns. In one embodiment, the width W of the gaps 1332 is 25 microns. It should be noted that some of the plurality of gaps 1332 may vary size and/or shape, thereby allowing the sensor/heater elements 1308, 1318 to have a wider dynamic range of response when sensing soot particle accumulation.

As shown, the first sensor/heater element 1308 includes first 1314 and second 1316 electrical contacts at opposite ends of the loop 1310. The first and second electrical contacts 1314, 1316 may be configured for coupling to circuitry for providing current through the loop 1310. Similarly, the second sensor/heater element 1318 includes first 1324 and second 1326 electrical contacts at opposite ends of the loop 1320. The first and second electrical contacts 1324, 1326 may be configured for coupling to circuitry for providing current through the loop 1320.

The first and second sensor/heater elements 1308, 1318 may include electrically conductive materials or metals, such as, alumina, gold, platinum, osmium, rhodium, iridium, ruthenium, aluminum, titanium, zirconium, and the like, as well as, oxides, alloys, and combinations including at least one of the foregoing metals. In one embodiment, the elements 1308, 1318 may include alumina having a film platinum trace deposited on a portion thereof.

The substrate 1302 may include a non-conductive and/or electrically insulating materials. Materials may include oxides, including, but not limited to, alumina, zirconia, yttria, lanthanum oxide, silica, and/or combinations including at least one of the foregoing, or any like material capable of inhibiting electrical communication and providing structural integrity and/or physical protection. Additionally, the soot sensor 1300 may include thick film and/or thin film constructions.

As described in greater detail herein, the soot sensor 1300 may be configured to operate in a first mode (hereinafter referred to as "soot sensing mode"), wherein the first and second sensor/heater elements 1308, 1318 are configured to sense soot accumulation on at least the first surface 1304 of the soot sensor 1300. The soot sensor 1300 may be further configured to operate in a second mode (hereinafter referred to as "regeneration mode"), wherein the first and second sensor/heater elements 1308, 1318 are configured to heat and remove (e.g. incinerate) at least a portion of accumulated soot on the first surface 1304, thereby cleaning/regenerating the sensor 1300.

The first and second sensor/heater elements 1308, 1318 may be configured to operate separately and independently from one another, as described in regards to the embodiment of FIG. 4. Additionally, the soot sensor 1300 may further include a switch S1 coupled to the second electrical contacts 1316, 1326 of the first and second sensor/heater elements 1308, 1318, respectively, for selectively coupling and decoupling the contacts 1316, 1326. For example, when the switch S1 is open, the first and second sensor/heater elements 1308, 1318 may operate separately from one another. When the switch S1 is closed, the first and second sensor/heater elements 1308, 1318 may be electrically coupled to one another, establishing a continuous loop of conductive material between contacts 1314 and 1324.

Figure 15:
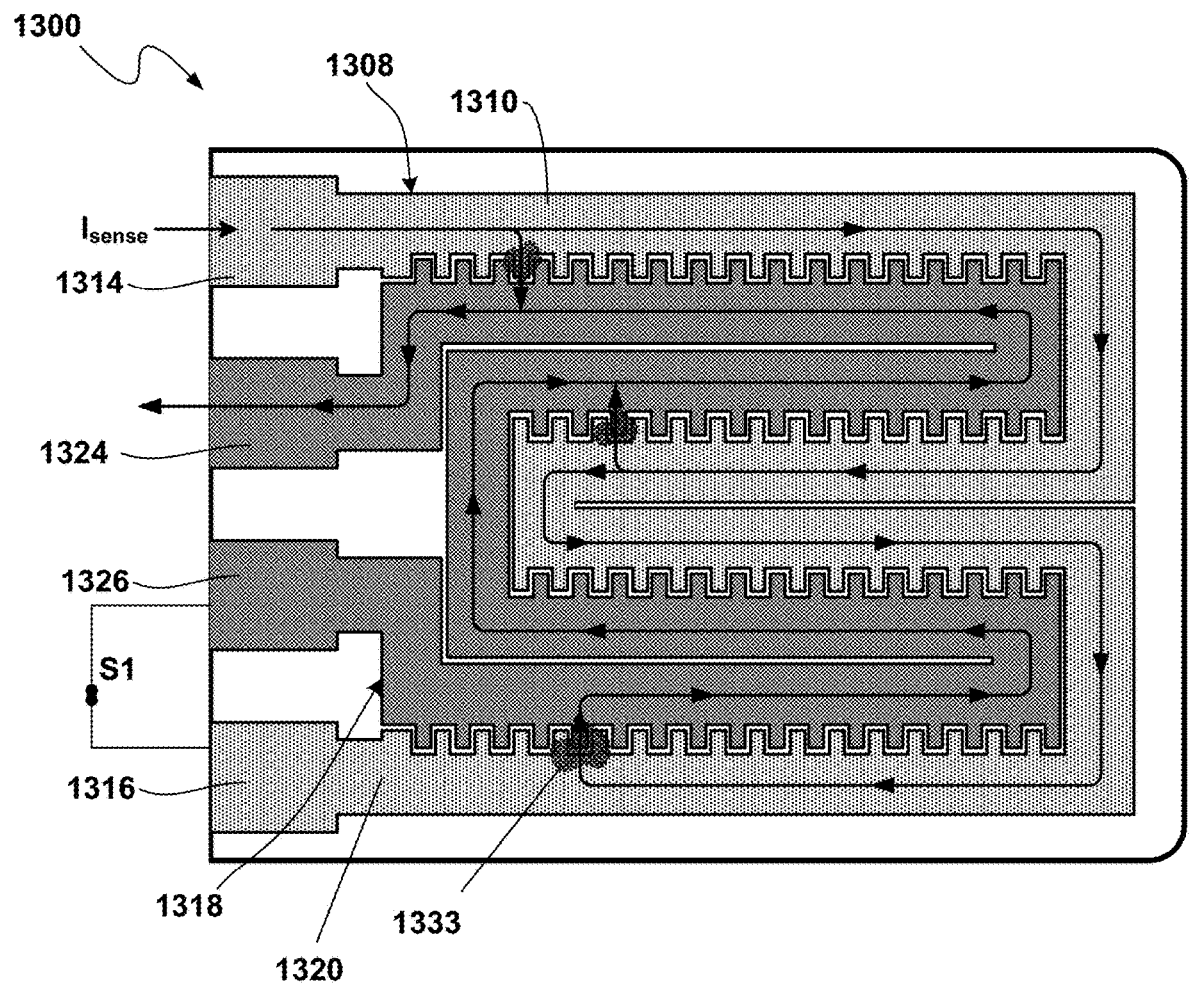
FIG. 15 is a schematic top view of the soot sensor of FIG. 13 in a soot sensing mode.

When the sensor 1300 is in the soot sensing mode, as shown in FIG. 15, an input current $I_{sense}$ may be provided at the first electrical contact 1314 (or second electrical 1316 contact). The value of $I_{sense}$ may be representative of the amount of soot disposed on the sensor 1300. As shown in FIG. 15, when the switch S1 is closed, the first and second sensor/heater elements 1308, 1310 are electrically coupled to one another and establish a continuous loop of conductive material between contacts 1314 and 1324. The current $I_{sense}$ may then pass through both the first sensor/heater element 1308 and second sensor/heater element 1318 to allow both the first and second sensor/heater elements 1308, 1318 to act as a single sensor element. Soot particles 1333 are shown as accumulated on the first surface 1304 of the substrate 1302, including on the first and second sensor/heater elements 1308, 1318. As soot 1333 builds up on the sensor/heater elements 1308, 1318, the resistance of the continuous loop (e.g. made of loops 1310 and 1320) changes, which changes the value of $I_{sense}$ The value of $I_{sense}$ is thus representative of the amount of soot accumulated on the sensor.

Figure 16:
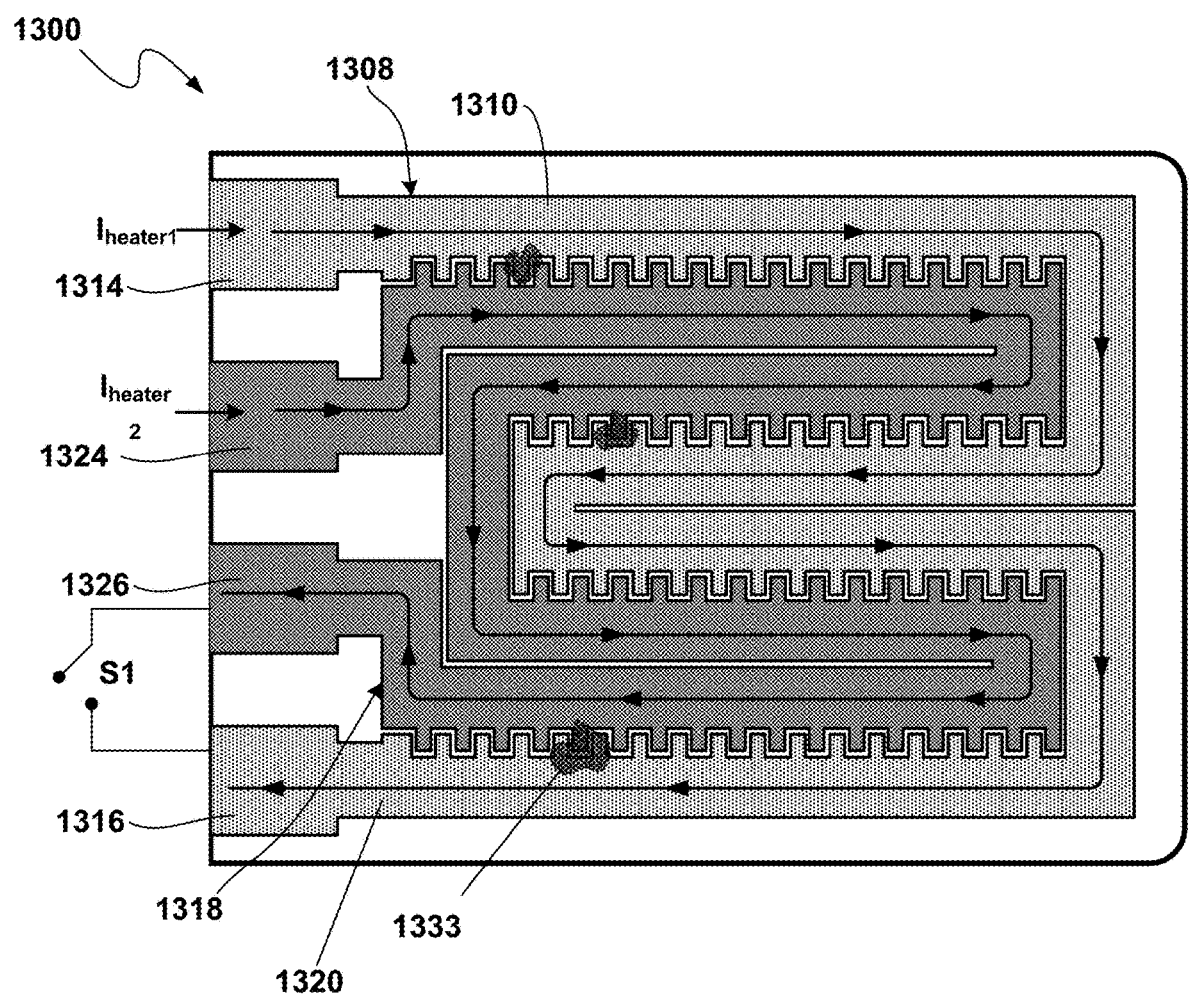
FIG. 16 is a schematic top view of the soot sensor of FIG. 13 in a regeneration mode.
Figure 17A:
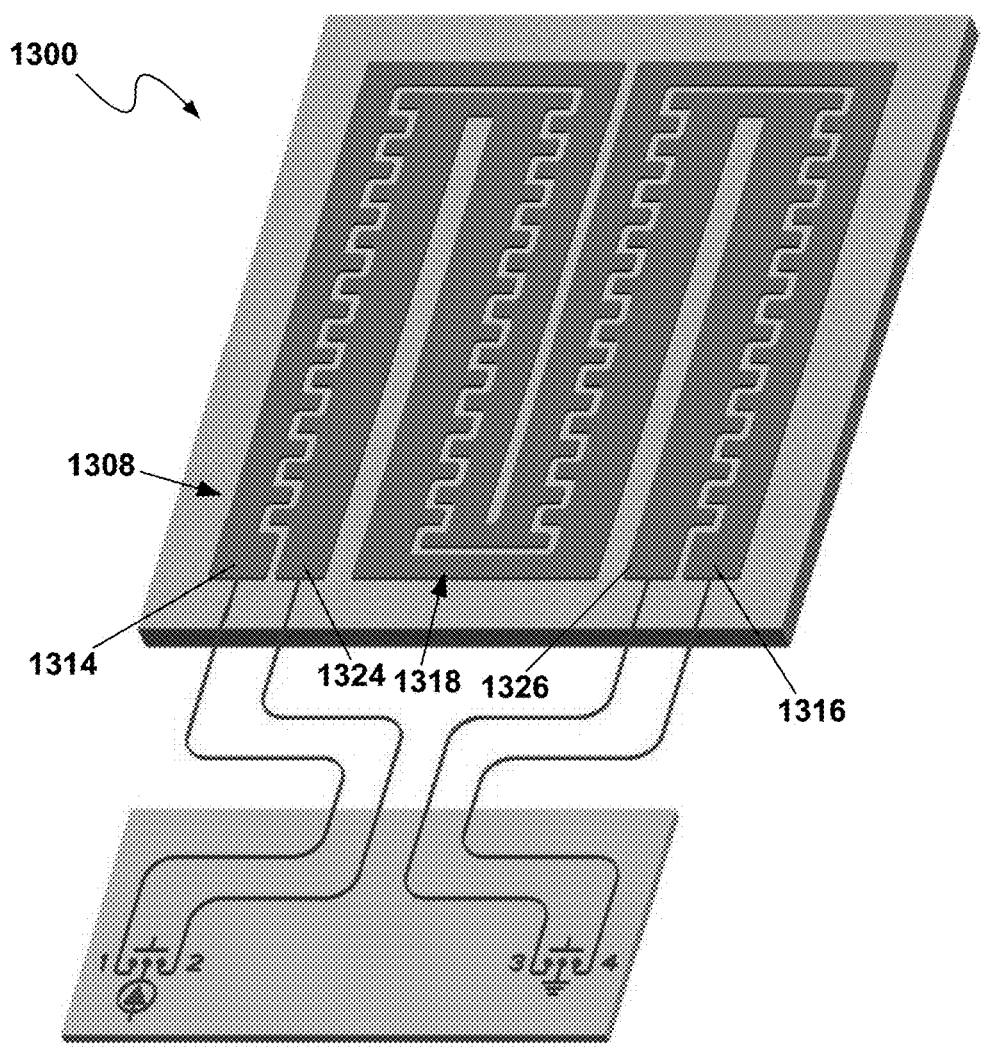
FIGS. 17A-17D are schematic top views and associated circuitry of the soot sensor of FIG. 13 in first and second regeneration modes.
Figure 17B:
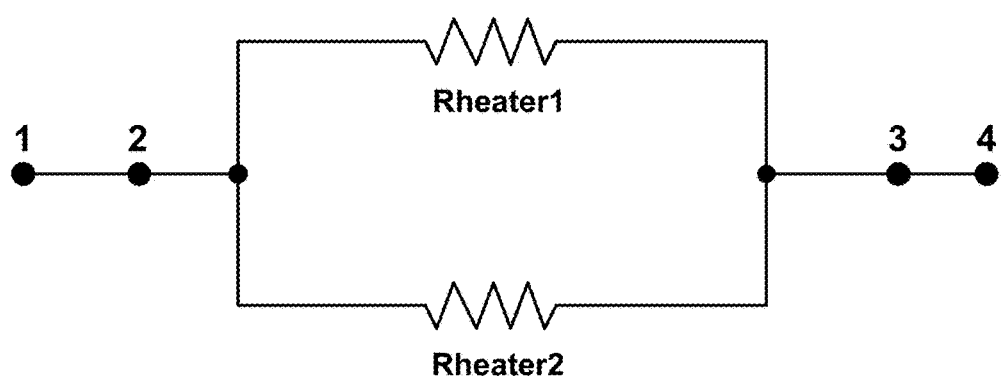

When a threshold amount of soot 1333 accumulates on the first and second sensor/heater elements 1308, 1318, e.g. as determined by reaching a threshold value of $I_{sense}$, the soot sensor 1300 may be configured to enter the regeneration mode, as shown in FIGS. 16 and 17A-17B. Referring to FIG. 16, when the sensor 1300 is in the regeneration mode, an input current $I_{heater1}$ may be provided at the first electrical contact 1314 (or second electrical 1316 contact) of the first sensor/heater element 1308. Similarly, an input current $I_{heater2}$ may be provided at the first electrical contact 1324 (or second electrical 1326 contact) of the second sensor/heater element 1318. In one embodiment, when a threshold amount of soot 1333 accumulates on the first and second sensor/heater elements 1308, 1318, e.g. as determined by reaching a threshold value of $I_{sense}$, the heater currents $I_{heater1}$ and/or $I_{heater2}$ may be applied to cause the corresponding first and second sensor/heater elements 1308, 1318 to heat and at least partially remove, e.g. incinerate, the soot 1333, thereby cleaning/regenerating the sensor 1300 for continued use.

In one embodiment, when the switch S1 is open, the first and second sensor/heater elements 1308, 1318 may operate independently of one another, wherein the heater current $I_{heater1}$ may be applied to cause only the first sensor/heater element 1308 to heat up. Similarly, the heater current $I_{heater2}$ may be applied to cause only the second sensor/heater element 1318 to heat up. When the switch S1 is closed, loops 1310 and 1320 are electrically coupled to one another establishing a single continuous loop of conductive material between the contacts 1314 and 1324. The current $I_{heater1}$ may then pass through both the first sensor/heater element 1308 and second sensor/heater element 1318 to allow both elements 1308, 1318 to act as a single heater element and heat up.

The soot sensor 1300 may be configured to operate in a first regeneration mode and a second regeneration mode, as shown in FIGS. 17A-17D. FIG. 17A illustrates the soot sensor 1300 in a first generation mode and 17B illustrates a schematic view of the circuitry associated with the soot sensor 1300 in the first generation mode. As shown, when in a first regeneration mode, the first and second sensor/heater elements 1308, 1318 may be arranged in parallel with one another. This configuration may be suitable for situations in which the first and second sensor/heater elements 1308, 1318 are hot and the resistance is high, thereby necessitating a need to pass more input current into the elements 1308, 1318 to increase heating of the elements 1308, 1318 during high flow conditions.

Figure 17C:
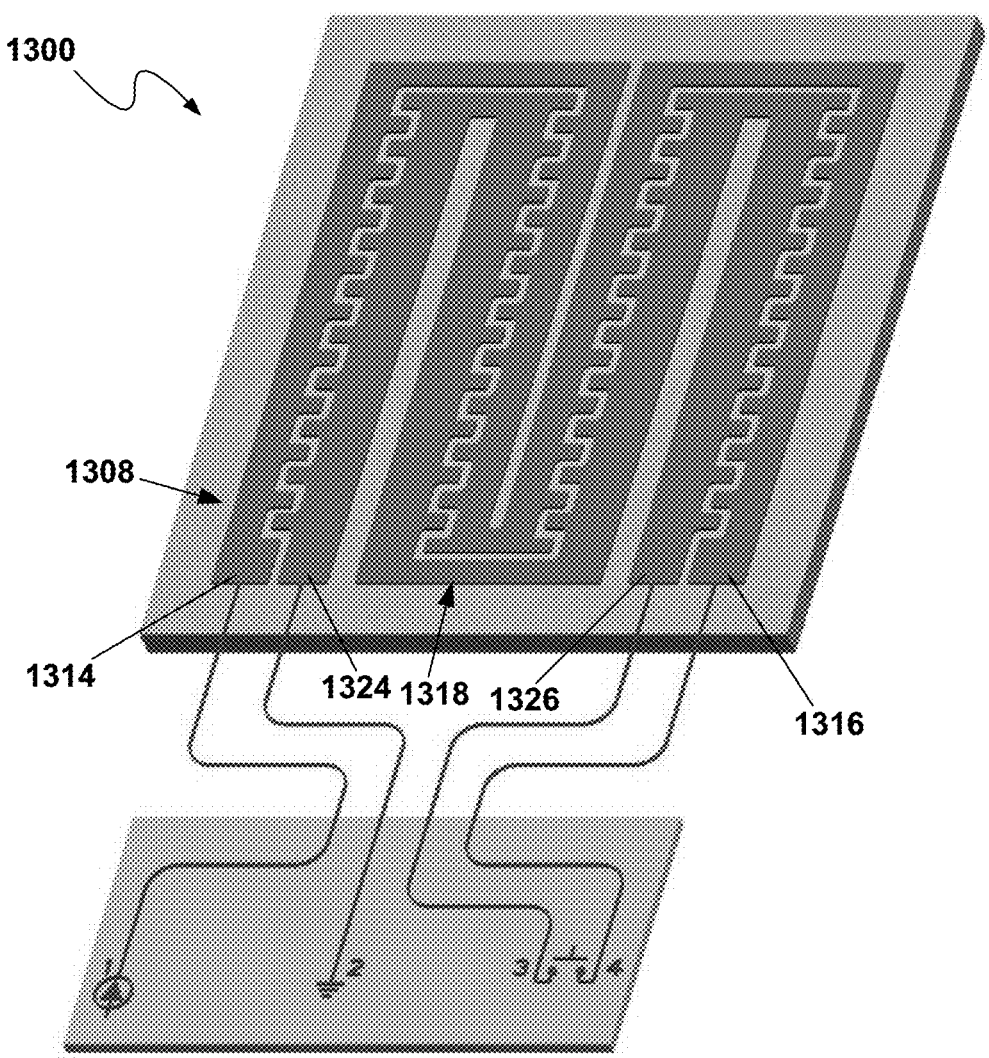
Figure 17D:
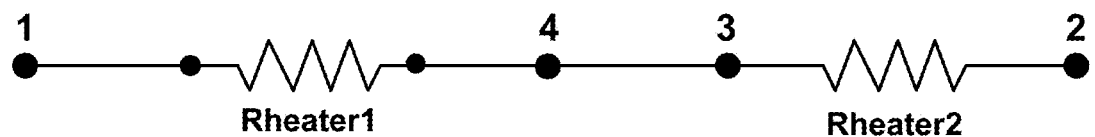

FIG. 17C illustrates the soot sensor 1300 in a second generation mode and 17D illustrates a schematic view of the circuitry associated with the soot sensor 1300 in the second generation mode. As shown, when in a second regeneration mode, the first and second sensor/heater elements 1308, 1318 may be arranged in series with one another. Arrangement of the first and second sensor/heater elements 1308, 1318 in a series generally results in a higher resistance than the resistance of a parallel arrangement (shown in FIG. 17A). Thus, operating in the second regeneration mode (e.g. series configuration) may be suitable for situations in which it is desirable to limit current consumption and/or when the first and second sensor/heater elements 1308, 1318 are cold and rapid heating is desired. Additionally, a higher resistance may also provide an improved temperature measurement of the elements 1308, 1318 during regeneration due to higher resolution.

It should be noted that the first and second regeneration modes may be controlled under solid state switching and software control. Accordingly, in some embodiments consistent with the present disclosure, the soot sensor may be configured to provide staged heating, wherein operation of the elements 1308, 1318 in the first and/or second regeneration modes may be controlled (e.g. start, stop, pause, change between modes, etc.) in real-time or near real-time to account for exhaust flow velocity and/or exhaust temperature.

Figure 18:
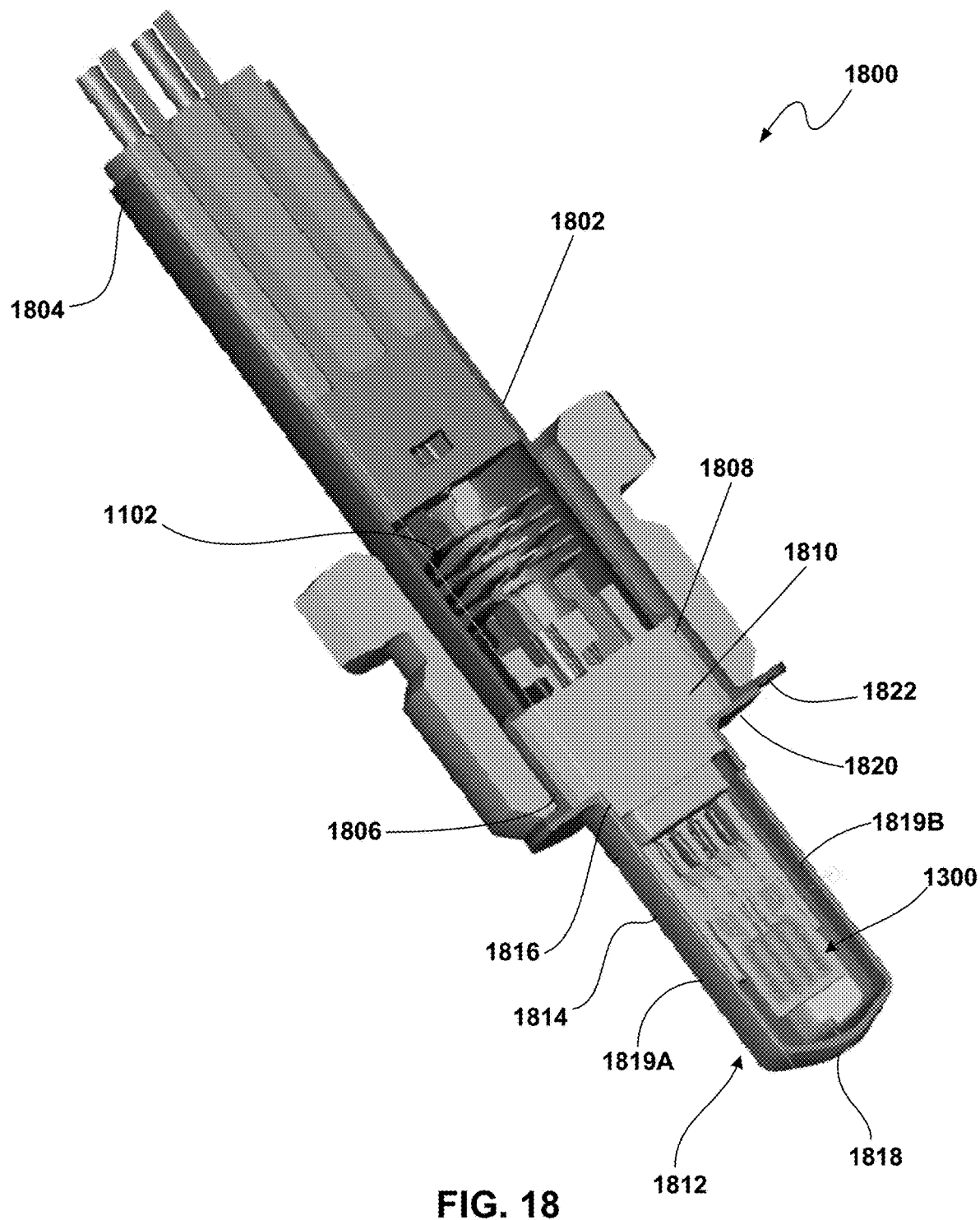
FIG. 18 is a perspective sectional view of a soot sensor assembly consistent with the present disclosure.

FIG. 18 is a perspective sectional view of one embodiment of a soot sensor assembly 1800 consistent with the present disclosure. Generally, the soot sensor assembly 1800 includes a housing 1802 having a first end 1804 and a second 1806. The housing 1802 is shaped and/or sized to partially enclose a slug insert 1810. The housing 1802 may include metal and/or non-metal material. As shown, the second end 1806 of the housing 1802 is shaped and/or sized to receive a portion of the slug insert 1810 and retain the slug insert 1810 by way of a ring 1808 coupled to at least a portion of the slug insert 1810. The ring 1808 may be coupled to the housing 1802 by various methods known to those skilled in the art. In one embodiment, the ring 1808 may be laser welded to the housing 1802, thereby providing a hermetic seal between the housing 1802 and ring 1808 (e.g. substantially impervious to air and/or gas).

The soot sensor assembly 1800 further includes a soot sensor 1300 coupled to the slug insert 1810. For purposes of clarity and description, references will be made to the soot sensor 1300 of FIG. 13. It should be noted, however, that the soot sensor assembly 1800 may include other embodiments of a soot sensor consistent with the present disclosure. The soot sensor assembly 1800 further includes a sensor tip 1812 coupled to at least the housing 1802 and configured to at least partially enclose the soot sensor 1300. The sensor tip 1812 includes a body 1814 having an open proximal end 1816 and a closed distal end 1818. The body 1814 includes an exterior surface 1819A and an interior surface 1819B.

In the illustrated embodiment, the proximal end 1816 of the sensor tip 1812 may define a flange portion 1820 configured to engagingly mate with a flange portion 1822 of the second end 1806 of the housing 1802. The sensor tip 1812 may be coupled to at least the housing 1802 at the respective flange portions 1820, 1822, wherein the flange portions 1820, 1822 may be sealed to one another. Additionally, the housing 1802 may be configured to partially enclose circuitry 1102 electrically coupled to the soot sensor 1300 and configured to provide electrical current to the soot sensor 1300.

Figure 19A:
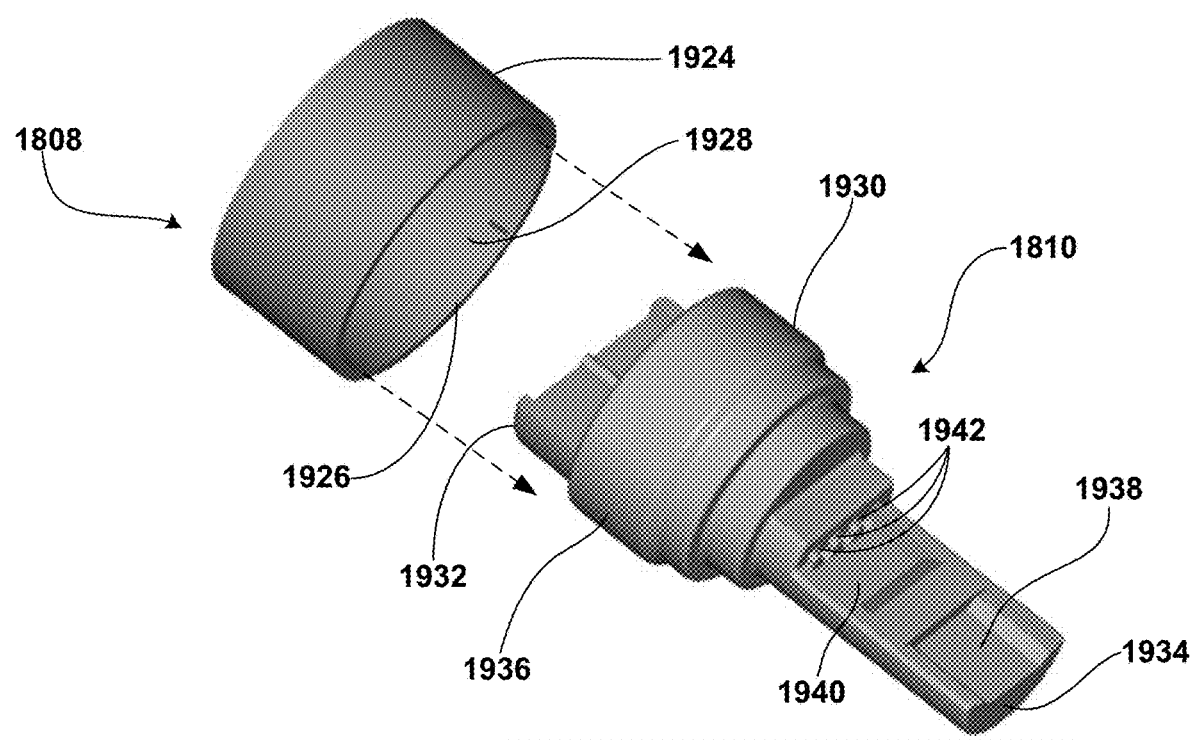
FIGS. 19A-19B are perspective views of embodiments of the soot sensor assembly of FIG. 18.
Figure 19B:
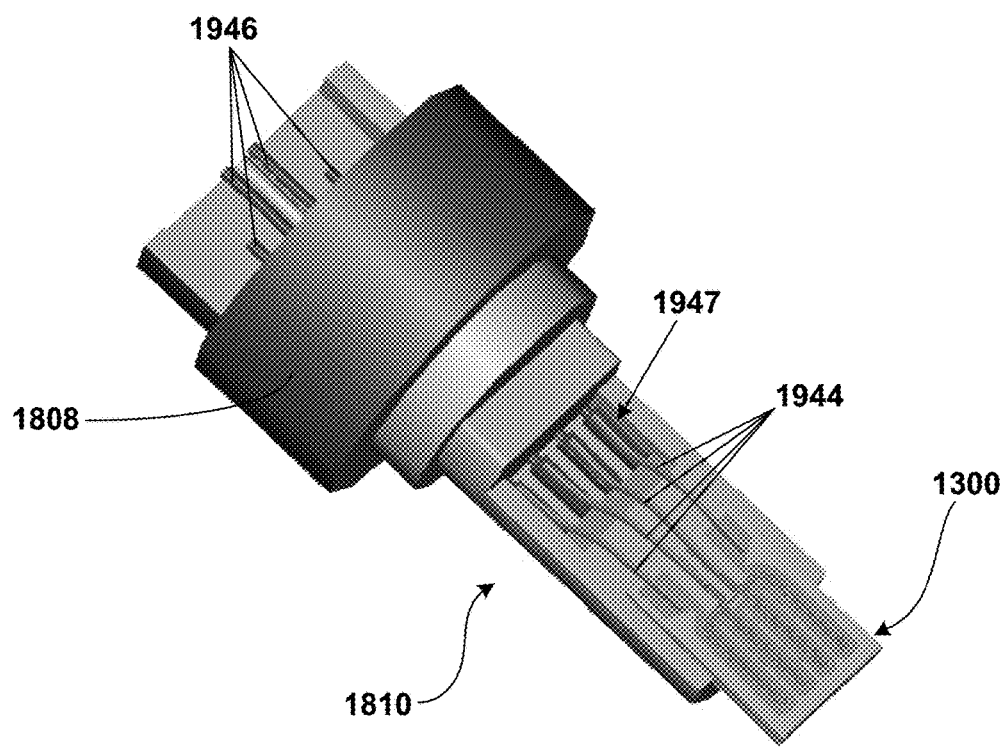

FIGS. 19A-19B are perspective views of the slug insert 1810 of the soot sensor assembly 1800 of FIG. 18. FIG. 19A illustrates the slug insert 1810 separated from the ring 1808 and FIG. 19B illustrates the slug insert 1810 coupled to the ring 1808. The ring 1808 may include a body 1924 defining an interior surface 1928 and a periphery 1926 having a circumference. The ring 1808 may be configured to receive at least a portion of the slug insert 1810. The ring 1808 may include metal and/or non-metal materials.

In the illustrated embodiment, the slug insert 1810 includes a body 1930 having a proximal end 1932 and a distal end 1934. The body 1930 also includes a discrete portion 1936 having a circumference less than the circumference of the periphery 1926 of the ring 1808, such that the discrete portion 1930 is configured to fit within the ring 1808 and be coupled to the interior surface 1928. The discrete portion 1936 of the slug insert 1810 may be coupled to the interior surface 1928 of the ring 1808 by various methods known to those skilled in the art. In one embodiment, for example, the discrete portion 1936 of the slug insert 1810 may be joined to the interior surface 1928 of the ring 1808 by a brazing method, thereby providing a substantially hermetic seal between the slug insert 1810 and the ring 1808.

The body 1930 of the slug insert 1810 also includes a first surface 1938 configured to support at least a portion of the soot sensor 1300 and a second surface 1940 configured to support electrical connections, e.g. interconnect wires 1946 coupled to leads 1944, as indicated by arrow 1947, of the soot sensor 1300. The body 1930 further includes apertures 1942 passing from at least the second surface 1940 through the body 1930 and to the proximal end 1932 of the slug insert 1810. The apertures 1942 are configured to receive and to allow the interconnect wires 1946 to pass from circuitry 1102 in the housing 1802 through a portion of the slug insert 1810 (e.g. body 1930) to the second surface 1940.

The first surface 1938 may define a channel shaped and/or sized to receive at least a portion of the soot sensor 1300. The first surface 1938 may further be configured to provide minimal contact with the soot sensor and to prevent heat loss during soot sensor regeneration process (heating of heater element(s)). The sensor element 1300 may be sealed to the first surface 1938 with glass, thereby increasing durability of the soot sensor 1300 during production assembly and decreasing vibration tendency. As appreciated by one skilled in the art, the soot sensor 1300 may be coupled to the first surface 1938 by other known methods.

As shown, the second surface 1940 may define a channel shaped and/or sized to receive a portion of the lead wires 1944 and associated interconnect wires 1946 coupled thereto. The apertures 1942 having interconnect wires 1946 passing therethrough may be filled with a sealant, such as glass, thereby providing a hermetic seal between the interconnect wires 1946 and the associated apertures 1942.

The slug insert 1810 may include non-conductive and/or electrically insulating materials. Materials may include oxides, including, but not limited to, alumina, zirconia, yttria, lanthanum oxide, silica, and/or combinations including at least one of the foregoing, or any like material capable of inhibiting electrical communication. In the illustrated embodiment, the slug insert 1810 may include a ceramic material.

Figure 19C:
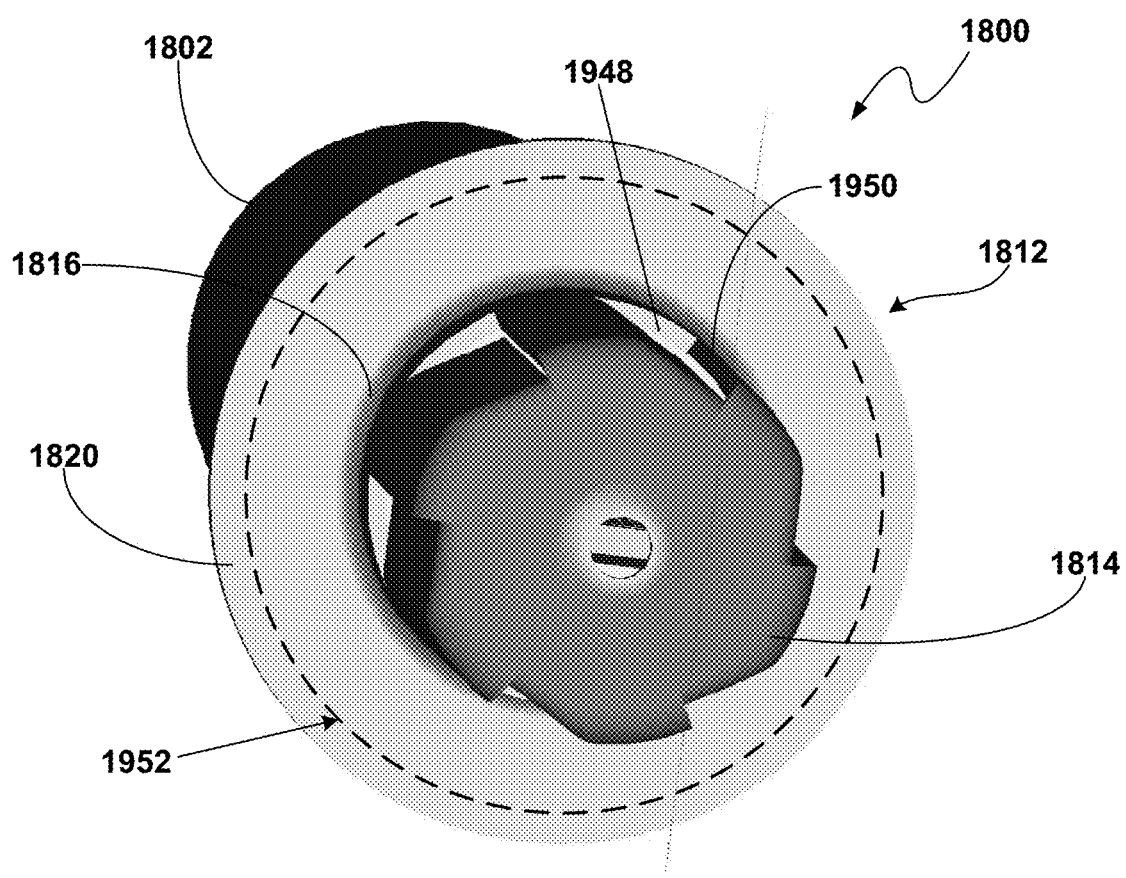
FIG. 19C is an enlarged perspective view of a portion of the soot sensor assembly of FIG. 18.

FIG. 19C is an enlarged perspective view of a portion of the soot sensor assembly 1800 of FIG. 18. As described earlier, the soot sensor assembly 1800 may include a sensor tip 1812 coupled to at least the housing 1802 and configured to at least partially enclose the soot sensor 1300. In the illustrated embodiment, the body 1814 of the sensor tip 1812 defines at least one angularly disposed channel 1948 defining a path 1950 from the exterior surface 1819A of the body 1814 to the interior surface 1819B of the body 1814. Similar to the embodiment of FIG. 9, the path 1950 is configured to direct exhaust flow to the soot sensor 1300. In the illustrated embodiment, the body 1814 of the sensor tip 1812 defines a plurality of angularly disposed channels 1948 positioned along an entire circumference of the body 1814. It should be noted that the soot sensor assembly 1800 may include other embodiments of a sensor tip consistent with the present disclosure.

In the illustrated embodiment, the proximal end 1816 of the sensor tip 1812 may define a flange portion 1820. The flange portion 1820 is configured to engagingly mate with the flange portion 1822 of the second end 1806 of the housing 1802. The flange portion 1820 of the sensor tip 1812 may be laser beam welded to the flange portion 1822 of the housing 1802, thereby providing a hermetic seal, as indicated by arrow 1952. As one skilled in the art would readily appreciate, the flange portions 1820, 1822 may be coupled to one another by other known methods.

Figure 20:
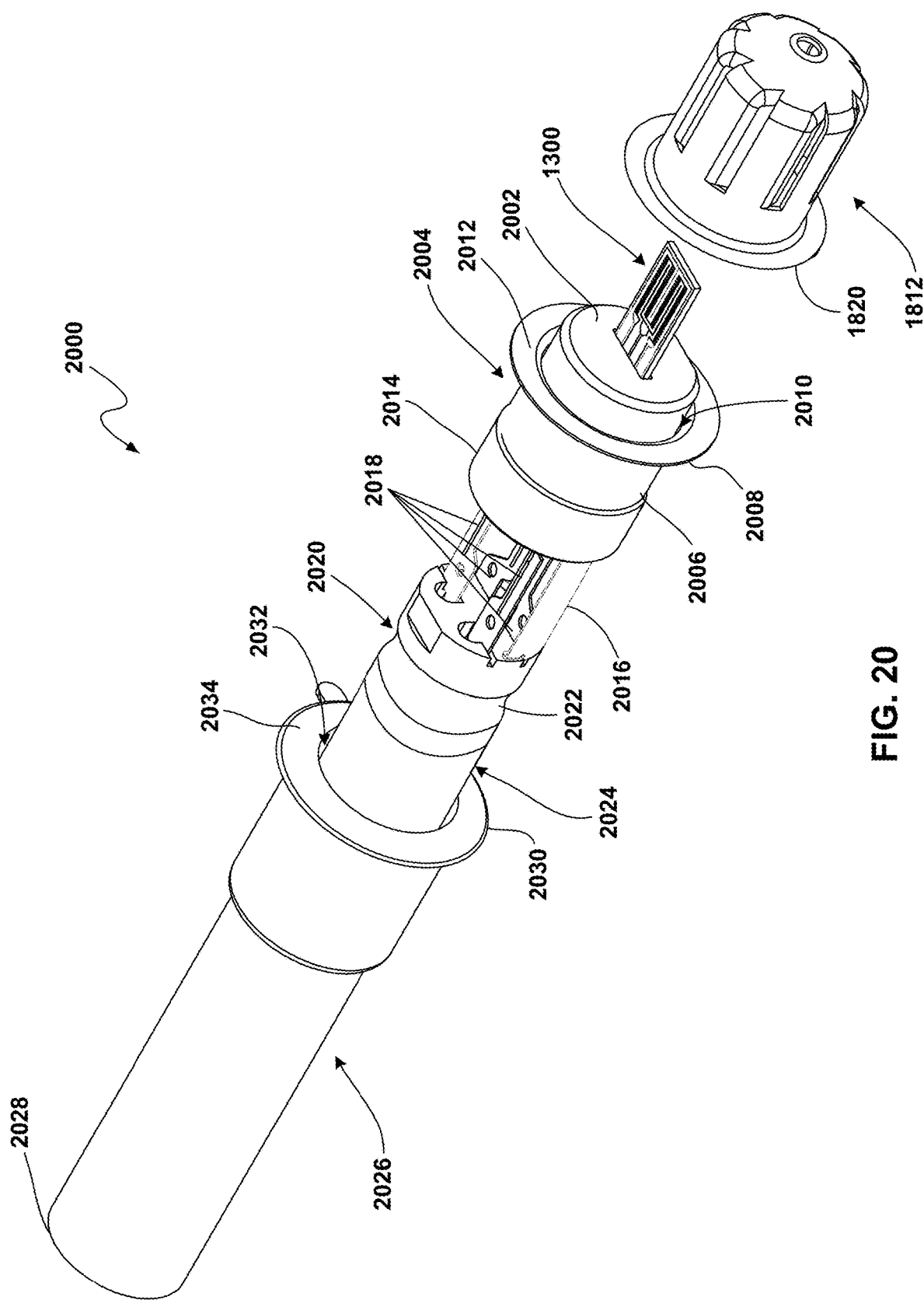
FIG. 20 is a perspective exploded view of another soot sensor assembly consistent with the present disclosure.
Figure 21:
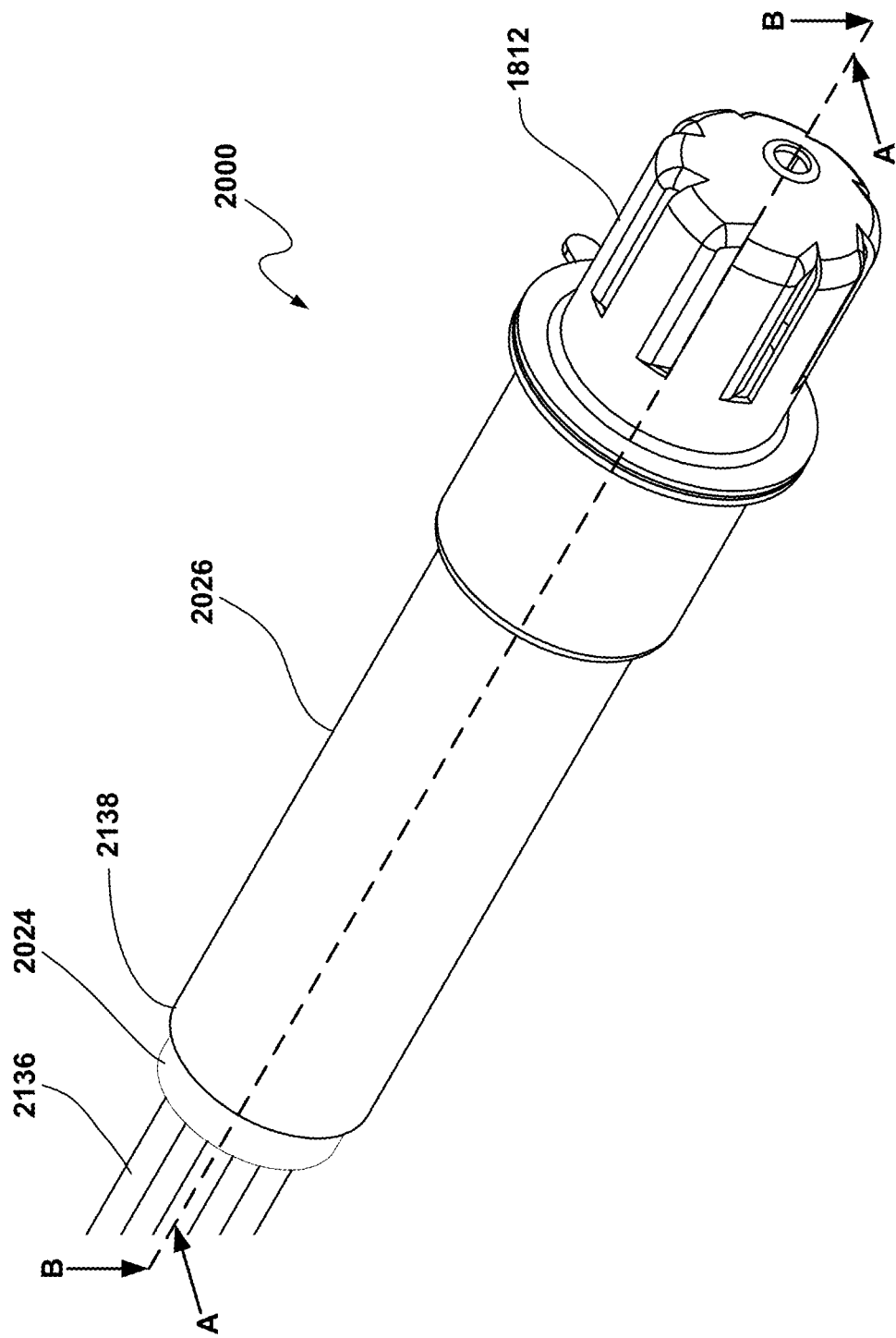
FIG. 21 is a perspective view of the soot sensor assembly of FIG. 20 in an assembled state.

FIG. 20 is a perspective exploded view of another soot sensor assembly 2000 consistent with the present disclosure and FIG. 21 is a perspective view of the soot sensor assembly 2000 of FIG. 20 in an assembled state. Generally, the soot sensor assembly 2000 includes an insulating member 2002 configured to receive and retain a portion of a soot sensor. For purposes of clarity and description, references will be made to the soot sensor 1300 of FIG. 13. It should be noted, however, that the soot sensor assembly 2000 may include other embodiments of a soot sensor consistent with the present disclosure. The insulating member 2002 may include non-conductive and/or electrically insulating materials. Materials may include oxides, including, but not limited to, alumina, zirconia, yttria, lanthanum oxide, silica, and/or combinations including at least one of the foregoing, or any like material capable of inhibiting electrical communication and/or withstanding relatively high temperatures (e.g., 600° C.). In the illustrated embodiment, the insulating member 2002 may include a ceramic material.

As shown, the assembly 2000 further includes an inner housing member 2004 having a first end 2006 and a second end 2008 and a longitudinally disposed passageway 2010 extending from the first end 2006 to the second end 2008. The passageway 2010 is shaped and/or sized to receive a portion of the insulating member 2002 within. As described in greater detail herein, the inner housing member 2004 may be shaped and/or sized to receive one or more materials configured to secure lead wires (shown in FIGS. 22A-22B) in a relatively fixed position.

As shown, the soot sensor assembly 2000 further includes a sensor tip configured to be coupled to a portion of the inner housing member 2004. For purposes of clarity and description, references will be made to the sensor tip 1812 of FIG. 18. It should be noted, however, that the soot sensor assembly 2000 may include other embodiments of a sensor tip consistent with the present disclosure. The sensor tip 1812 may be coupled to at least the inner housing member 2004 and is configured to partially enclose the soot sensor 1300. In the illustrated embodiment, the flange portion 1820 of the sensor tip 1812 is configured to engagingly mate with a flange portion 2012 defined on the second end 2008 of the inner housing member 2004. The sensor tip 1812 may be coupled to at least the inner housing member 2004 at the respective flange portions 1820, 2012, wherein the flange portions 1820, 2012 may be sealed to one another.

The assembly 2000 further includes a first spacing member 2014 positioned adjacent the first end 2006 of the inner housing member 2002. The size (e.g. width) of the first spacing member 2014 may depend on the desired length of the lead wires, for example. The soot sensor assembly 2000 further includes a second spacing member 2016 positioned adjacent the spacing member 2016. For purposes of clarity, the second spacing member 2016 is illustrated partly in section. The size (e.g. width) of the second spacing member 2016 may depend on the desired length of the terminals 2018, for example. The first and second spacing members 2014, 2016 may include non-conductive and/or electrically insulating materials. Materials may include oxides, including, but not limited to, alumina, zirconia, yttria, lanthanum oxide, silica, and/or combinations including at least one of the foregoing, or any like material capable of inhibiting electrical communication. In the illustrated embodiment, the first and/or second spacing members 2014, 2016 may include a ceramic material.

The soot sensor assembly 2000 further includes a strain relief nugget 2020 configured to receive and retain a portion of each of the terminals 2018 therein. The nugget 2020 may further be coupled to a wire harness assembly 2136 (shown in FIG. 21). As shown, the nugget 2020 may include one or more passageways for each terminal 2018 to be received within. The nugget 2020 may include two complementary halves, wherein, when positioned adjacent and complementary to one another, they combine to form a unitary nugget 2020, as shown. The nugget 2020 may further include a radial groove 2022 defined on a portion thereof. The groove 2022 may provide a clearance (e.g. space) to allow a portion of the outer housing member 2026 to be crimped inwardly towards the nugget 2020 such that the crimped portion of outer housing member 2026 applies little or no force upon the nugget 2020.

The nugget 2020 may be configured to provide strain relief for connections (e.g. welds) coupling the wires of the wire harness assembly 2136 to the terminals 2018. For example, the nugget 2020 may provide strain relief if the wire harness assembly 2136 is pulled during installation or regular use. The nugget 2020 may include non-conductive and/or electrically insulating materials. Additionally, the nugget 2020 may include plastic over-molded material.

As shown, a grommet 2024 may be positioned adjacent the nugget 2020. The grommet 2024 may have a hollow tubular cross-section, such that the wire harness assembly 2136 may pass through the grommet 2024 and be coupled to the terminals 2018. The grommet 2024 may include a flexible and resilient material, such as a molded high temperature rubber.

The soot sensor assembly 2000 further includes an outer housing member 2026 having a first end 2028 and a second end 2030 and a longitudinally disposed passageway 2032 extending from the first end 2028 to the second end 2030. The passageway 2032 is shaped and/or sized to receive and enclose the first and second spacing members 2014, 2016, the terminals 2018 and respective connections with lead wires from the sensor 1300 (shown in FIGS. 22A-22B), the nugget 2020, and a portion of the grommet 2024 within. The outer housing member 2026 may include one or more materials capable of inhibiting electrical communication and providing structural integrity and/or physical protection to components therein. The outer housing member 2026 may also include material capable of withstanding high temperatures.

In the illustrated embodiment, the second end 230 of the outer housing member 2026 defines a flange portion 2034. The flange portion 2034 is configured to engagingly mate with the flange portion 2012 of the second end 2008 of the inner housing member 2004. As such, the outer housing member 2026 may be coupled to at least the inner housing member 2004 at the respective flange portions 2034, 2012, wherein the flange portions 2034, 2012 may be sealed to one another by any known methods to provide a generally tight seal, thereby preventing moisture and/or other contaminants from entering the passageway 2032 of the outer housing member 2026 via the second end 2030.

When the outer housing member 2026 is positioned (e.g. slid) over components of the assembly 2000, a portion of the outer housing member 2026 at or near first end 2028 may be crimped, such that a diameter of the outer housing member 2026 may be reduced at or near the first end 2028. The crimped portion 2138 may compress a portion of the grommet 2024 positioned within the passageway 2032, wherein the compressed portion of the grommet 2024 may provide a generally tight seal and prevent moisture and/or other contaminants from entering the first end 2028 of the outer housing member 2026. The crimped portion 2138 may further securely retain and fix the nugget 2020 within the passageway 2032 of the outer housing member 2028.

FIG. 22A is a top sectional view of the soot sensor assembly of FIG. 21 taken along lines A-A and FIG. 22B is a side sectional view of the soot sensor assembly of FIG. 21 taken along lines B-B. As shown, a portion of the soot sensor 1300 is positioned and retained within the insulating member 2002. In the illustrated embodiment, lead wires 2240 coupled to the sensor 1300 (e.g. coupled to the first 1314, 1323 and second 1324, 1326 electrical contacts of the elements 1308, 1318) extend away from the sensor 1300 and into the passageway 2010 of the inner housing member 2004 and eventually into the passageway 2032 of the outer housing member 2026. The lead wires 2240 may be coupled to associated terminals 2018, as indicated by arrow 2242.

A portion of the lead wires 2240 may be secured in a relatively fixed position within the inner housing member 2004 by way of a fixing material 2244. In one embodiment, the fixing material 2244 may be disposed within a portion of the passageway 2010 of the inner housing member 2004 and completely surround a portion of the lead wires 2240. The fixing material 2244 may be provided in a liquid form and then cured. The fixing material 2244 may be configured to provide stability and vibration protection to the sensor 1300 and lead wires 2240, thereby improving thermal response. The fixing material 2244 may include non-conductive and/or electrically insulating material, as well as moisture and/or corrosive resistant material, such as thermosetting plastics.

In one embodiment, the fixing material 2244 may include glass and may be used to seal a portion of the lead wires 2240 and the sensor 1300 within a portion of the passageway 2010 of the inner housing member 2004, thereby increasing durability of the soot sensor 1300 and/or lead wires 2240 during production assembly and decreasing vibration tendency. As appreciated by one skilled in the art, a portion of the lead wires 2240 may be fixed and sealed within the inner housing member 2004 by other known methods, such as, for example, any known potting methods.

Turning to FIGS. 23A-23B, perspective and sectional views, respectively, of one embodiment of the inner housing member 2304 of the soot sensor assembly 2000 of FIG. 20 are generally illustrated. This embodiment is similar to the embodiment of FIG. 20, and like components have been assigned like reference numerals in the twenty-three hundreds rather than the two thousands. Generally, the inner housing member 2304 includes a first end 2306 and a second end 2308 and a longitudinally disposed passageway 2310 extending from the first end 2306 to the second end 2308. The second end 2308 defines a flange member 2312 configured to matingly engage a flange portion 1820 of the sensor tip 1812. The inner housing member 2304 further includes an expanded portion 2314 defined along a radius of the inner housing member 2304. As shown in FIG. 23B, the expanded portion 2314 results in a complementary recessed portion 2316 formed on an inner surface 2318 of the passageway 2310.

As previously described, a fixation material 2244, such as glass, for example, may be filled within a portion of the passageway 2310 to securely fix one or more lead wires 2240 within. The fixing material 2244 may fill the recessed portion 2316 within the passageway 2310. When the fixing material 2244 has cured, the recessed portion 2316 may provide a means of securing the cured fixing material 2244 within the passageway 2310. More specifically, the cured portion of the fixing material 2244 within the recessed portion 2316 will prevent substantial movement of the cured fixing material 2244 in at least a longitudinal direction (i.e. from the first to the second ends 2306, 2308 of the inner housing member 2304). Additionally, the interior surface 2318 of the passageway 2310 may be configured to improve interaction between the fixation material 2244 and the inner housing member 2304. For example, in one embodiment, the interior surface 2318 may be roughened by any known means (e.g., but not limited to, oxidized, etc.) so as to provide an improved interaction between the fixation material 2244 and the interior surface 2318.

FIGS. 24A-24B are perspective and sectional views, respectively, of another embodiment of the inner housing member 2404 of the soot sensor assembly 2000 of FIG. 20. Generally, the inner housing member 2404 includes a first end 2406 and a second end 2408 and a longitudinally disposed passageway 2410 extending from the first end 2406 to the second end 2408. The second end 2408 defines a flange member 2412 configured to matingly engage a flange portion 1820 of the sensor tip 1812. The inner housing member 2404 further includes a recessed portion 2414 defined along a radius of the inner housing member 2404. As shown in FIG. 24B, the recessed portion 2314 generally results in a complementary generally annular ridge portion 2416 extending from an inner surface 2418 towards a center of the passageway 2410.

When the fixing material 2244 is filled within the passageway 2410, the fixing material 2244 may engage and fill around the ridge portion 2416 within the passageway 2410. When the fixing material 2244 has cured, the ridge portion 2416 may prevent movement of the cured fixing material 2244, thereby securing the cured fixing material 2244 within the passageway 2410. Similar to the embodiment of FIGS. 23A-23B, the interior surface 2418 of the passageway 2410 may be configured to improve interaction between the fixation material 2244 and the inner housing member 2404. For example, in one embodiment, the interior surface 2418 may be roughened by any known means (e.g., but not limited to, oxidized, etc.) so as to provide an improved interaction between the fixation material 2244 and the interior surface 2418.

Figure 25:
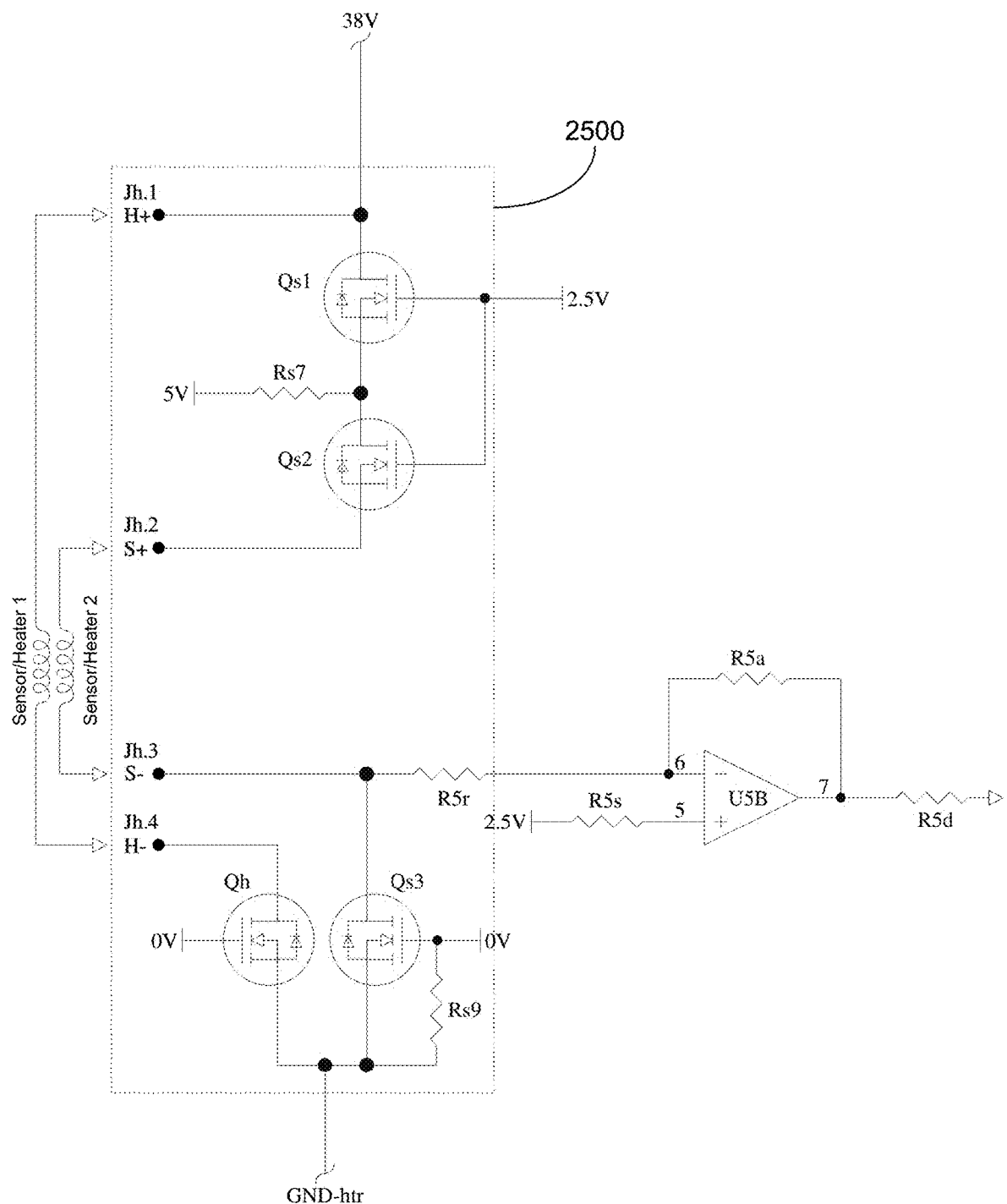
FIG. 25 is a schematic view of circuitry coupled to the soot sensor of FIG. 13.

FIG. 25 is a schematic view of circuitry coupled to the soot sensor of FIG. 13. The circuitry of FIG. 25 provides a means of nullifying leakage current effects when attempting to enhance soot collection of the soot sensor 1300. As shown, the first and second sensor/heater elements (e.g. Sensor/Heater1 and Sensor/Heater 2) may be configured for coupling to circuitry 2500 for providing current through the conductive materials of the first and second sensor/heater elements, wherein the current may be provided by a power supply configured to supply an input voltage, for example, of 38 V. In the illustrated embodiment, the circuitry 2500 may include a first transistor Qs1, a second transistor Qs2, a third transistor Qs3, and a fourth transistor Qs4. The transistors Qs1-Qs4 may include any type of switching device. In the illustrated embodiment, the transistors Qs1-Qs4 may include MOSFETs. The transistors Qs1-Qs4 may be configured to control the application of current from the power supply to the first and/or second heater elements.

As shown, Qh is off and the third transistor Qs3 is off, thereby providing the same potential (0V) at the source as the gate through resistor Rs9. A voltage of 2.5V is applied to the first and second transistors Qs1, Qs2, thereby resulting in both the first and second transistor Qs1, Qs2 being off. When the first transistor Qs1 off, an voltage of 5V will be applied to the drain of the second transistor Qs2 through the pull-up resistor Rs7. A 2.5V potential is thereby provided at the drain of the third transistor Qs3 and the source of the second transistor Qs2 through resistor R5r. With the circuit arranged as described, the second transistor Qs2 will have a 5V potential at its drain and 2.5V at its source, resulting in a drain-source voltage drop of 2.5V. Additionally, with 2.5V at the source and 2.5V at the gate of the second transistor Qs2, the second transistor Qs2 will have a 0V difference in potential between its gate and its source. The third transistor Qs3 will have a 2.5V potential at its drain, and with its source being grounded, a potential of 0V at its source, resulting in a drain-source voltage drop of 2.5V, matching that of the second transistor Qs2. With the gate and source of the second transistor Qs2 being at the same potential as that of the third transistor Qs3, the resulting difference in potential between the third transistors Qs3 gate and source is 0V, again, matching that of the second transistor Qs2. With both the second and third transistors Qs2, Qs3 equally biased, the soot measurement can be taken with the leakage current effects being cancelled out.

Figure 26:
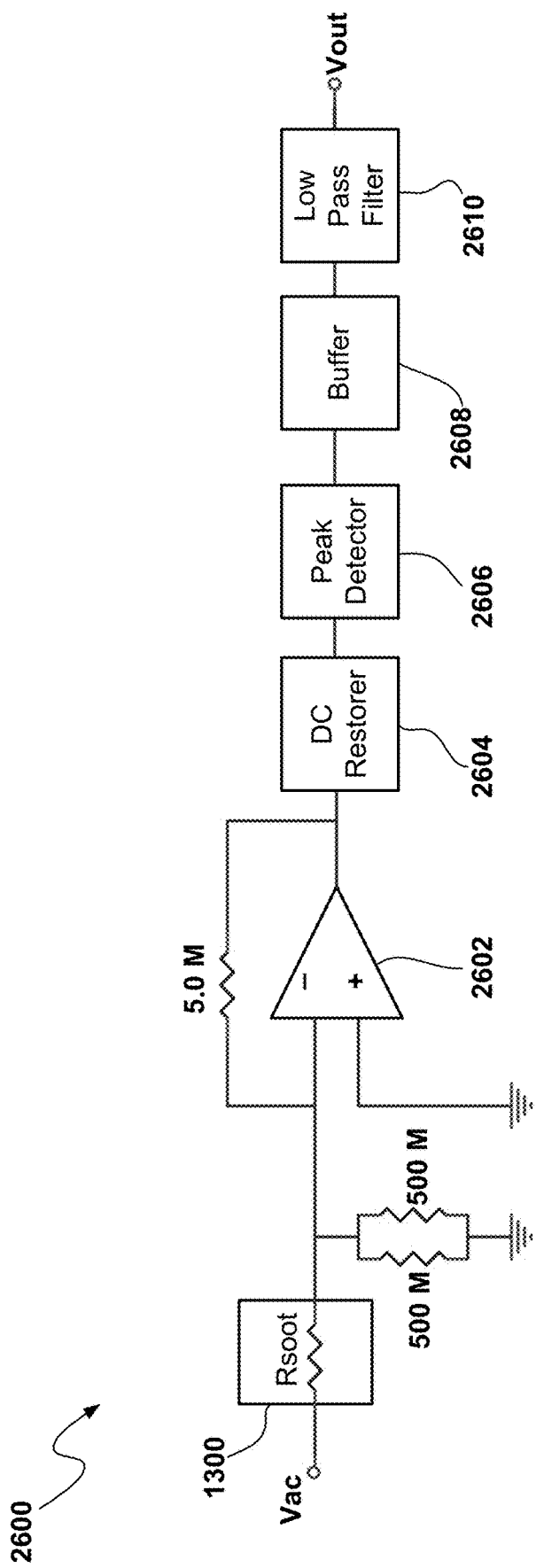
FIG. 26 is a block diagram of a signal processing system coupled to the soot sensor of FIG. 13.

FIG. 26 is a block diagram of an alternating current (AC) coupled signal processing system coupled to the soot sensor of FIG. 13. The AC coupled signal processing system 2600 may include the soot sensor 1300, as shown in FIG. 13, configured to receive an input AC supply voltage Vac and coupled to an amplifier 2602 configured to receive signal currents passing through the soot sensor 1300, including the resistance between the first and second sensor/heater elements 1308, 1318 (Rsoot). The system 2600 may further include a DC restorer 2604 coupled to the amplifier 2602. The DC restorer 2604 may be configured to synchronously ground signals from said amplifier 2602. A peak detector 2606 may be coupled to and configured to receive signals from the DC restorer 2604. Additionally, a buffer 2608, such as a unity gain operational amplifier (shown in FIG. 20), may be coupled to and configured to receive signals from the peak detector 2606. The system 2600 may further include a low pass filter 2610 coupled to and configured to receive signals from the buffer 2608, wherein the low pass filter 2610 may be configured to remove switching transients from received. With the assumption of a dynamic resistance of 500 M Ohms to both ground and to the input power supply, the AC equivalent circuit is illustrated as two 500 M Ohm resistors to ground. Additionally, incrementally, the two 500 M Ohm resistors are coupled between ground and the inverting input of the operational amplifier 2602, and, as such, may have little effect on an AC signal (current).

Figure 27:
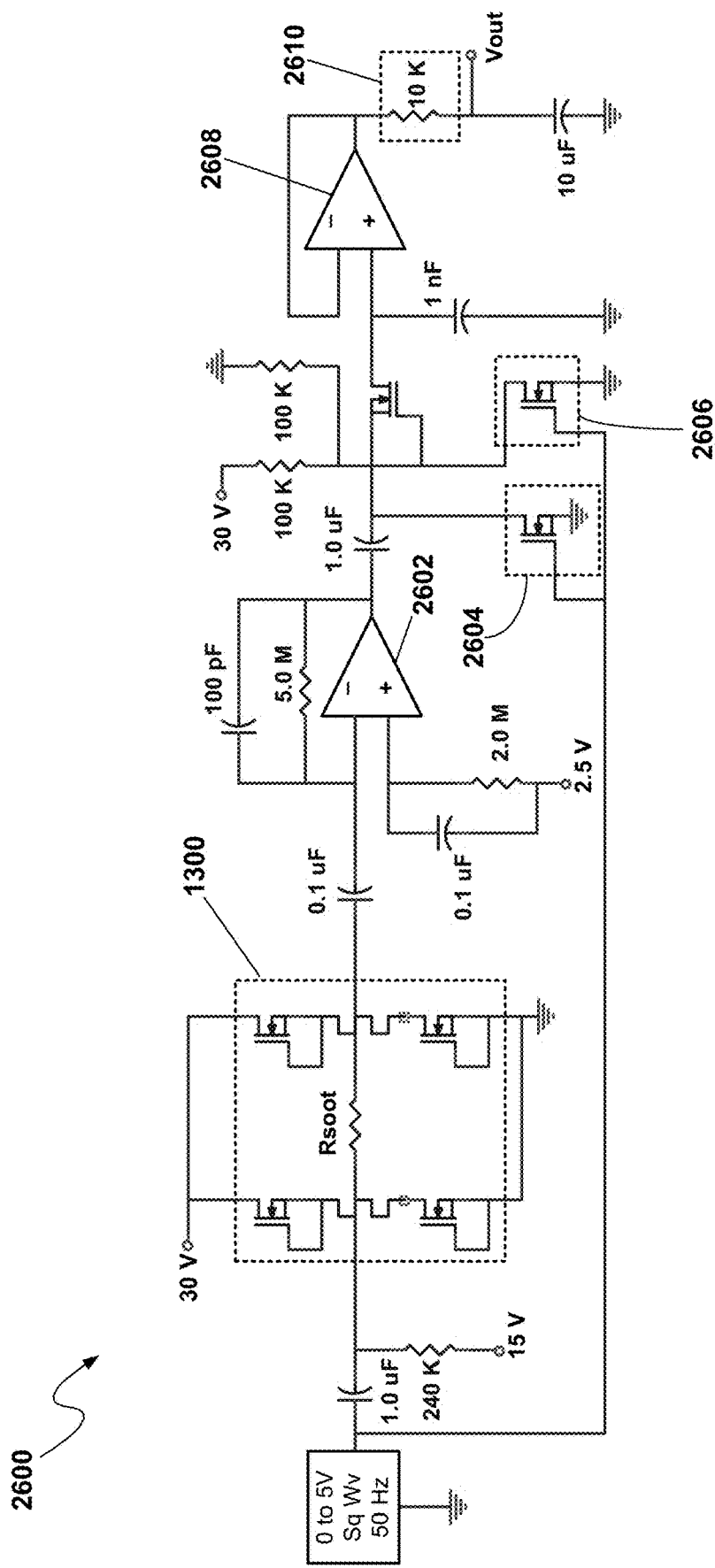
FIG. 27 is a schematic view of the signal protection circuitry of FIG. 26.

FIG. 27 is a schematic view of the circuitry of the signal processing system of FIG. 26. To lessen the effect of the DC leakage currents that may occur in transistors of the circuitry of the soot sensor 1300, an AC coupled approach can be implemented. Due to the fact that the dynamic resistance of the DC leakage of the transistors may be much larger than the DC resistance, an AC voltage divider would take advantage of this effect. The dynamic resistance of an ideal constant current source is ∞ Ohms. The dynamic resistance of the leakage of the transistors is δv/δi. In one example, the dynamic resistance may be approximately 500 M Ohms. This value may be more stable with changes in leakage and operating point.

By utilization of the AC coupled signal processing system 2600, the DC leakages of the transistors can be effectively eliminated from the resistance measurement Rsoot. The system 2600 may take advantage of very high dynamic resistance of the sources of leakage currents. For example, the system 2600 takes advantage of being able to couple the square wave stimulation and the resultant AC signals via capacitors, thereby allowing a desired AC signal to pass through the circuitry unattenuated (with properly sized capacitors). The undesired DC voltages (due to leakage currents of the transistors) and/or slow varying voltages due to thermal effects, may be rejected.

Referring to FIG. 27, the soot sensor 1300 may be configured to receive a variety of signal frequencies having varying waveforms (square, saw tooth, sinusoidal, etc) depending on the application taking into account any software and/or firmware and/or hardware included in the system and/or sensor. In the illustrated embodiment, the soot sensor 1300 may be configured to receive a signal having a square waveform having frequency of 50 Hz. It should be noted that the optimum frequency may help add robustness to EMC, allow better integration with the software and firmware as well as the hardware and might also have effects of signal to noise ratio and perhaps add to stability over life.

Additionally, the wave may be balanced around zero volts, such that the wave may cycle equally plus and minus relative to ground. Additionally, a standard waveform may be used that cycles from ground to some predetermined voltage level, such as 30 Vdc, resulting in a non-balanced waveform. The non-balanced version may decrease the life of Pt electrodes due to migration of the Pt. However, the non-balanced may be cheaper to implement as far as costs are concerned.

The AC coupled signal processing system 2600 may be configured to effectively eliminate DC leakages from transistors in the soot sensor circuitry. During operation, the DC restorer 2604 may be configured to synchronously ground the signal during the low voltage side of the square wave, thereby producing a zero voltage based square wave on the output side of the 1.0 uF capacitor. Additionally, the series connected MOSFET synchronously passes the peak value of this square wave to the 1.0 nF capacitor. This capacitor holds this peak value until the next cycle. This voltage is buffered by a unity gain op-amp 2608 and the output is then low pass filtered via the low pass filter 2610 to remove switching transients. In one example, in which there is no current leakage, if Rsoot is 100 M, then Vout is 5V*5.0 µA/(3.0 µA+100M)=0.24 V. Similarly, if Rsoot is 5 M, then Vout is 5V*5.0 µA/(5.0 µA+5.0M)=2.5 V.

Figure 28:
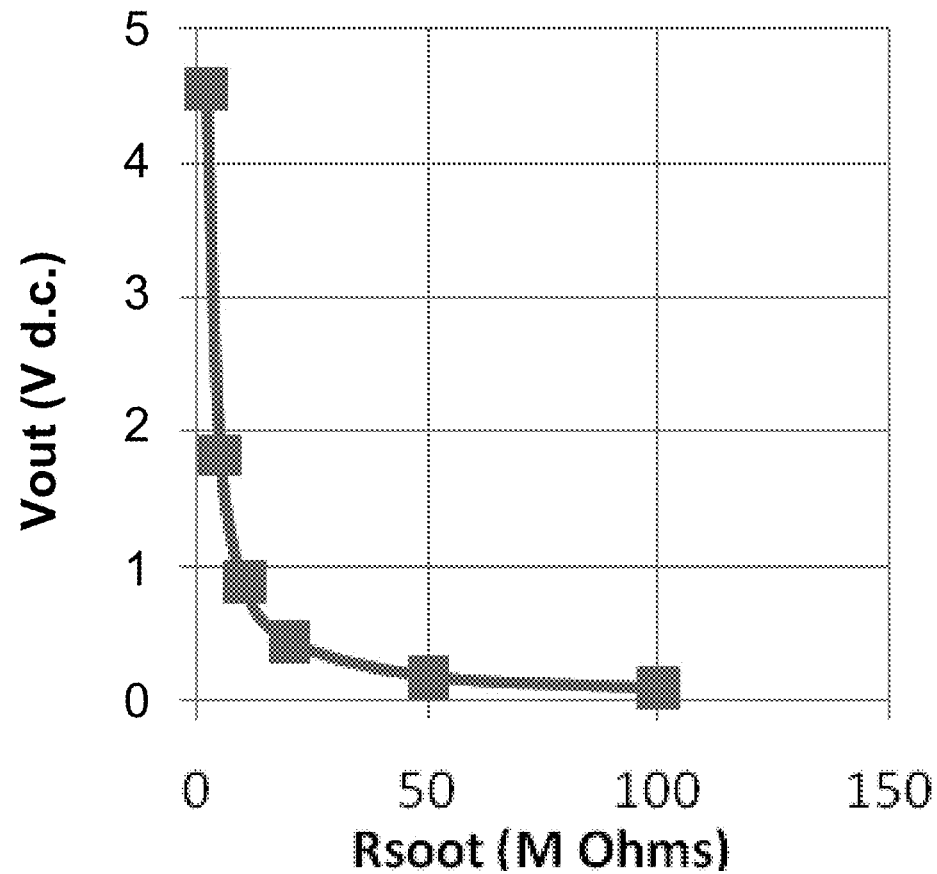
FIG. 28 is a plot of output voltage vs. resistance associated with an exemplary soot sensor consistent with the present disclosure.

FIG. 28 is a plot of output voltage vs. resistance associated with an exemplary soot sensor consistent with the present disclosure. The following table (shown immediately below) includes the measurements of the resistance Rsoot between the two heater elements during a soot measurement cycle and the corresponding output voltage Vout at 25° C. and 105° C.

TABLE 1

| Rsoot (M Ohms) | Vout (V) at 25° C. | Vout (V) at 105° C. |
| --- | --- | --- |
| 2 | 4.55 | 4.55 |
| 5 | 1.84 | 1.83 |
| 10 | 0.88 | 0.88 |
| 20 | 0.44 | 0.44 |
| 50 | 0.18 | 0.18 |
| 100 | 0.09 | 0.09 |

In the illustrated embodiment, because of the design of the circuitry of the AC coupled signal processing system 2600, the output voltage Vout is proportional to 1/Rsoot. This data exhibits a high degree of temperature stability. The 1/Rsoot method gives high resolution at the lower values of Rsoot, where it is desired.

Figure 29:
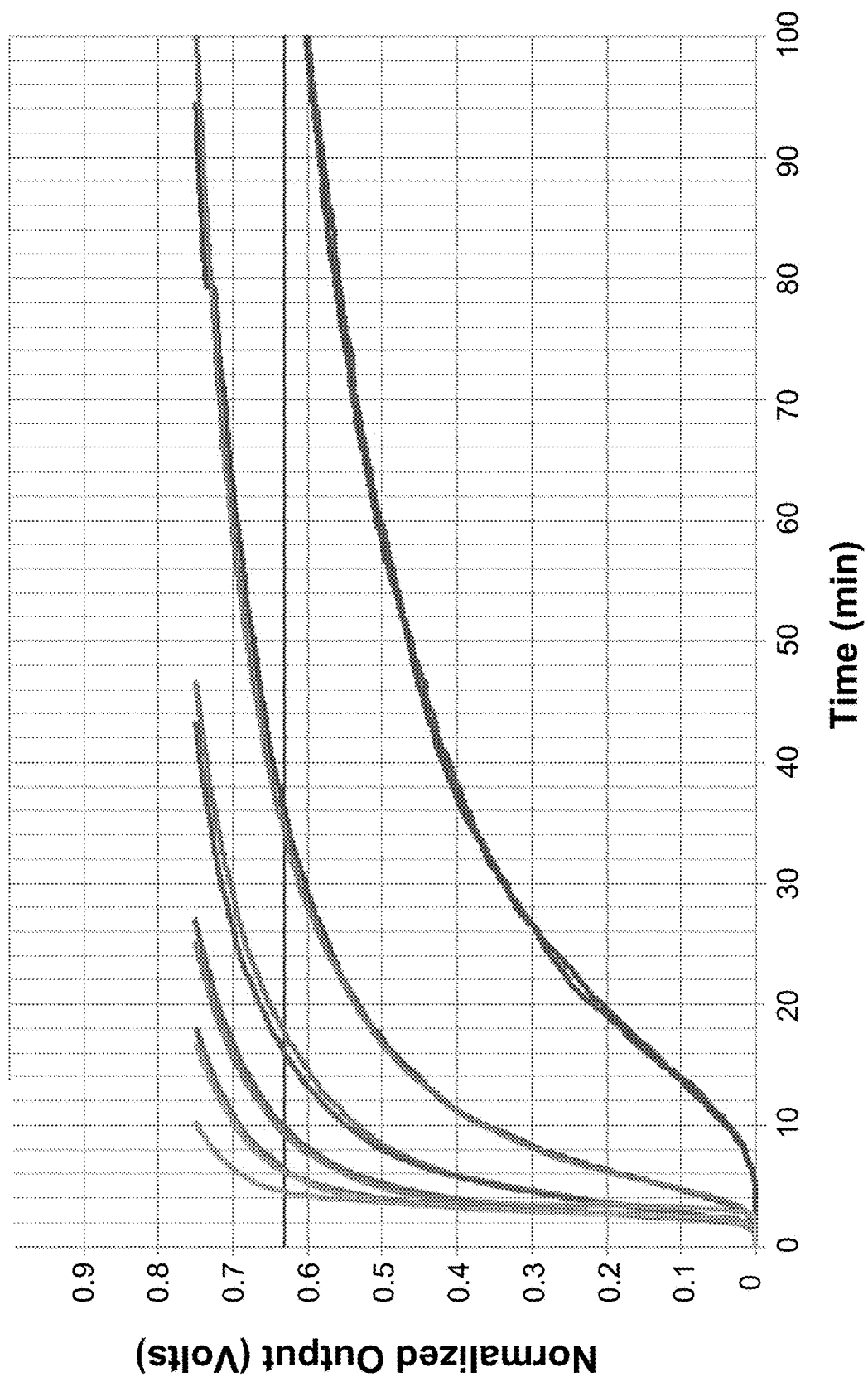
FIG. 29 includes plots of output voltage vs. time associated with an exemplary soot sensor consistent with the present disclosure.

FIG. 29 includes plots of output voltage vs. time associated with an exemplary soot sensor consistent with the present disclosure. The voltage (peak to peak) signal used to measure the resistance Rsoot may affect the sensor response time. As voltage is increased, response time is decreased. Since the circuit of the AC coupled signal processing system may be configured to operate on a 5 Vdc supply, a charge pump or other means may be implemented, thereby increasing sensor excitation voltage. This may result in the required current from the 5 Vdc supply to increase.

Figure 30A:
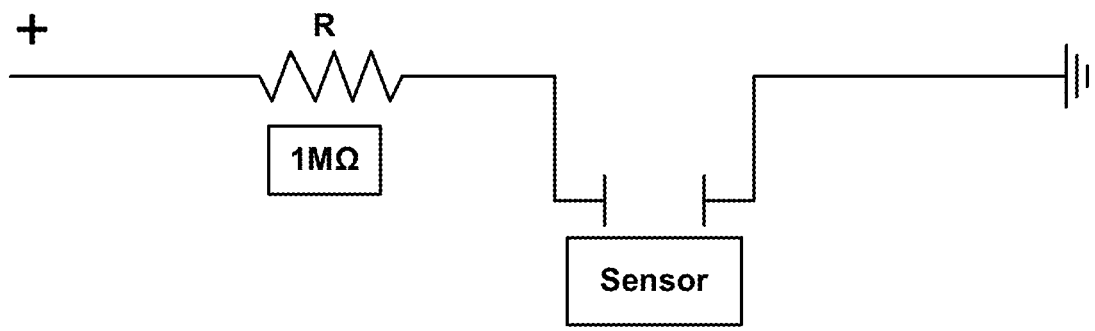
FIG. 30A is a schematic view of circuitry associated with an exemplary soot sensor consistent with the present disclosure.
Figure 30B:
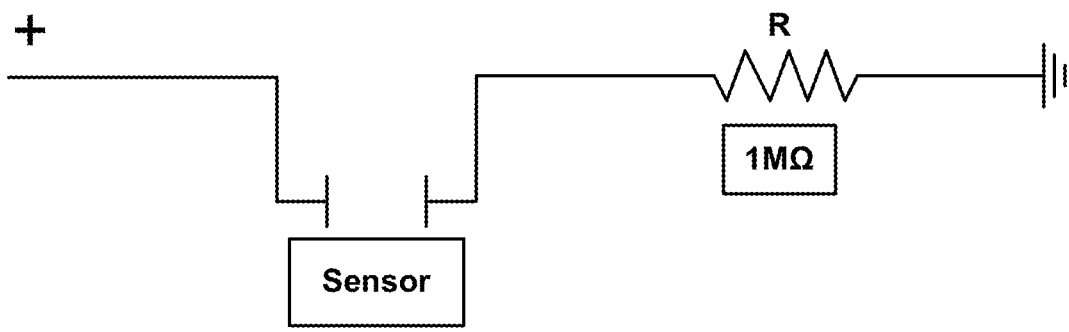
FIG. 30B is a schematic view of circuitry associated with an exemplary soot sensor consistent with the present disclosure.

FIGS. 30A and 30B are schematic views of circuitry associated with an exemplary soot sensor consistent with the present disclosure. FIG. 30A depicts a pull up resistor configuration and FIG. 30B depicts a pull down resistor configuration.

Figure 31:
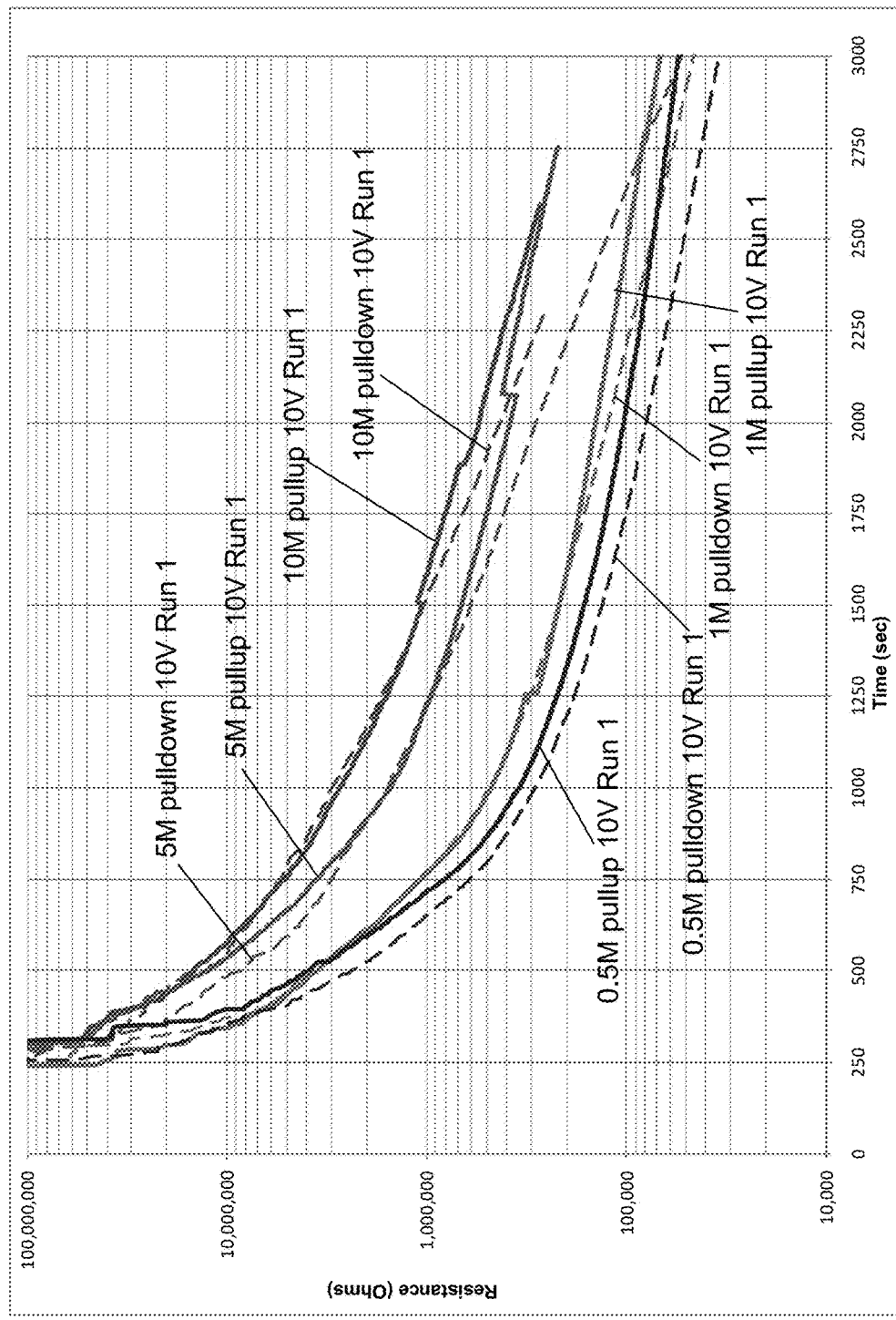
FIG. 31 is a plot of resistance vs. time associated with the circuitry of FIGS. 30A-30B.

FIG. 31 includes plots of resistance vs. time associated with the pull up and pull down resistor configurations of FIGS. 30A-30B. FIG. 31 illustrates the resistance of the pull up and pull down resistor configurations at two separate excitations voltages, including 10V and 5V. In the illustrated embodiment, the pull down resistor configuration created a slightly improved sensor response with smoother output signals.

Figure 32:
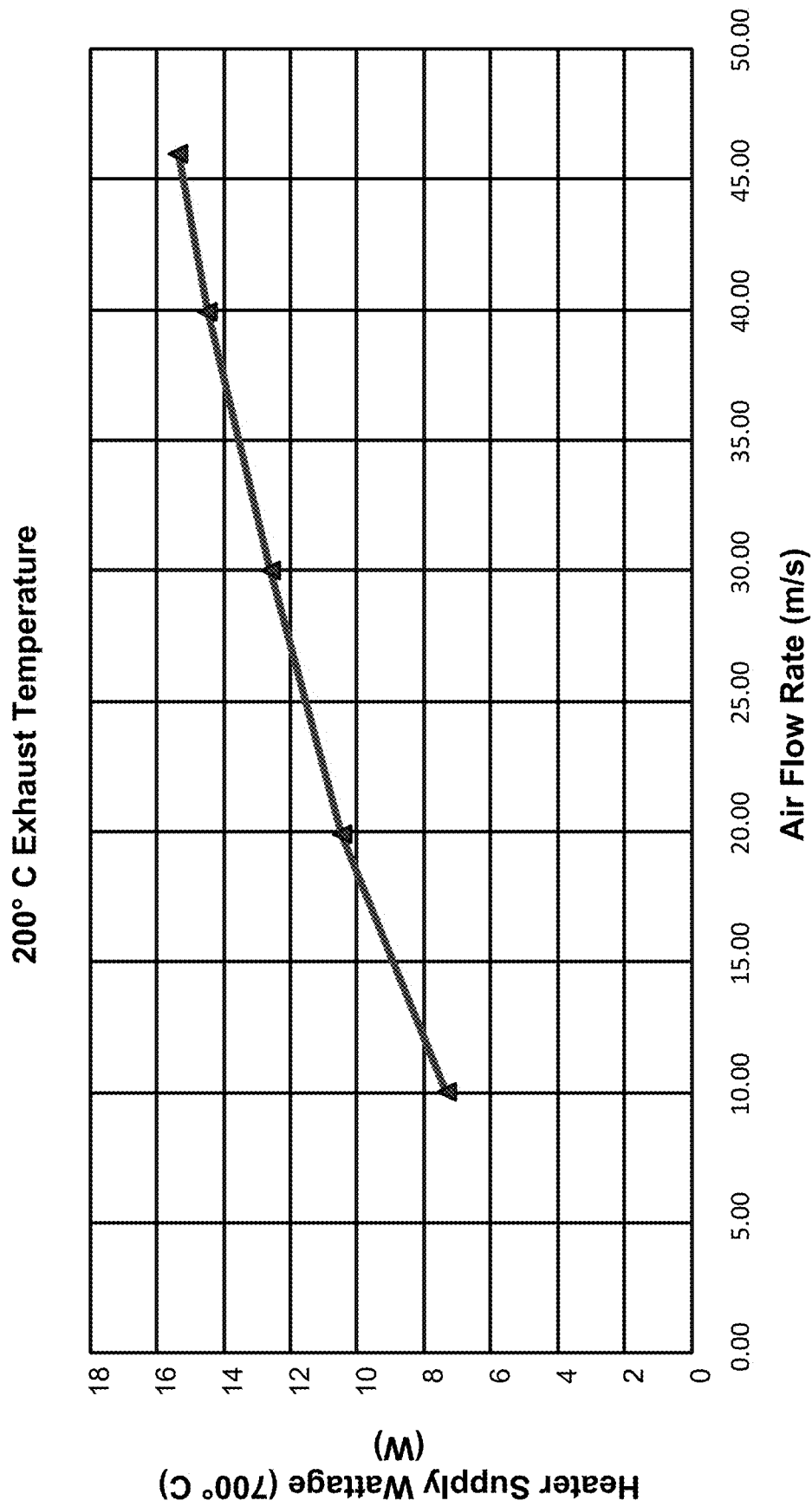
FIG. 32 is a plot of supply wattage vs. air flow rate associated with an exemplary soot sensor consistent with the present disclosure.
Figure 33A:
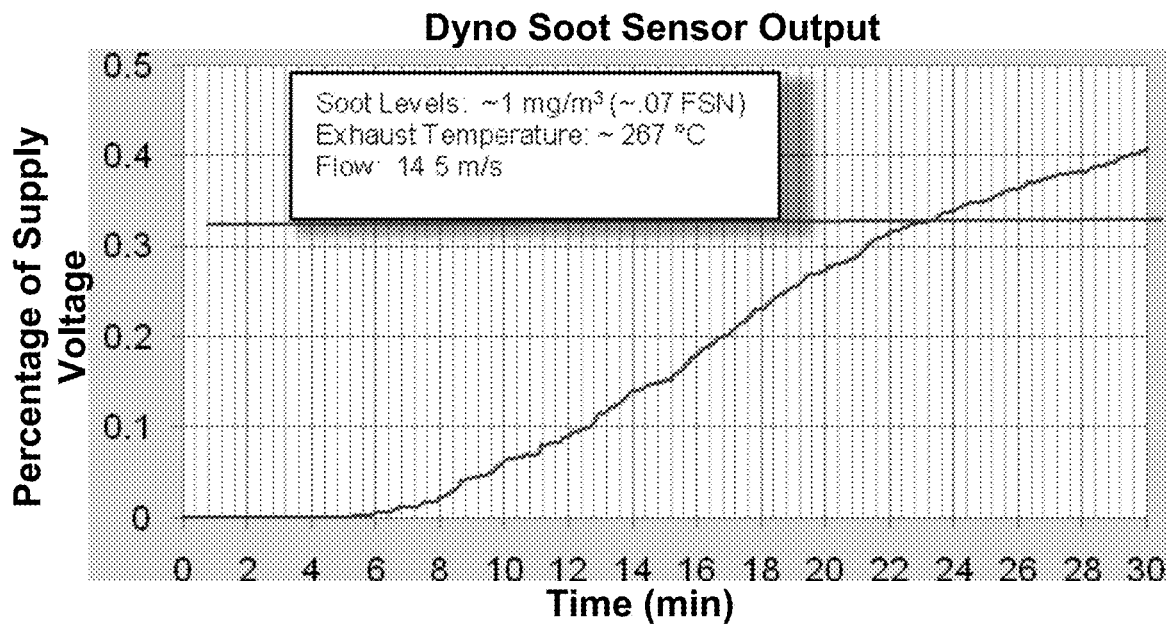
FIGS. 33A-33D are plots of supply voltage vs. time associated with an exemplary soot sensor consistent with the present disclosure.
Figure 33B:
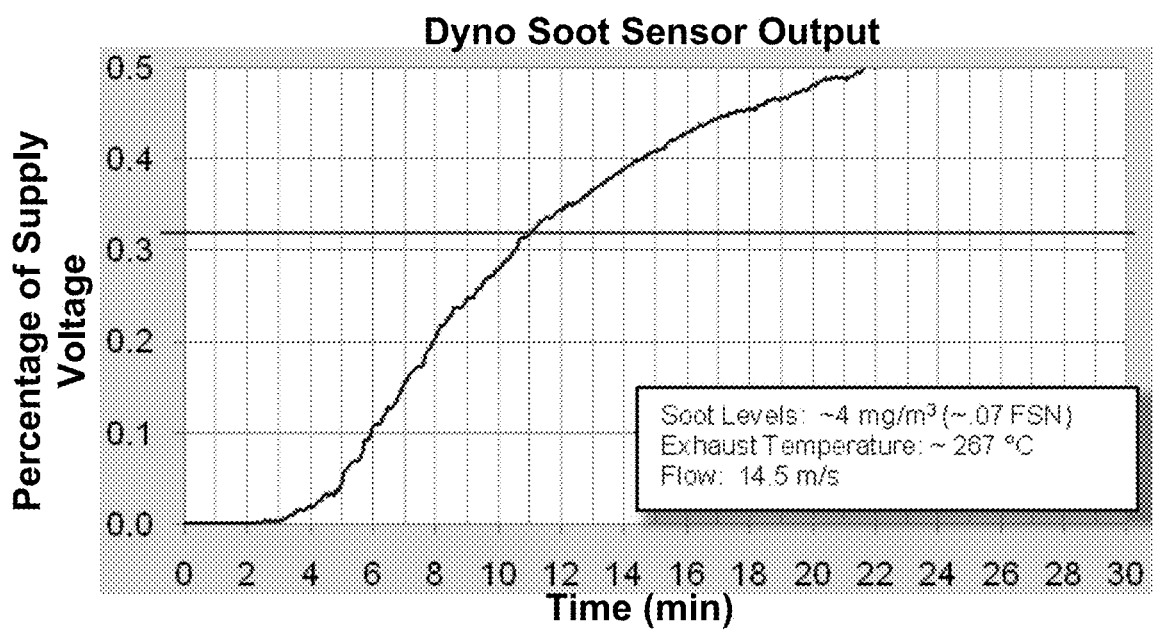
Figure 33C:
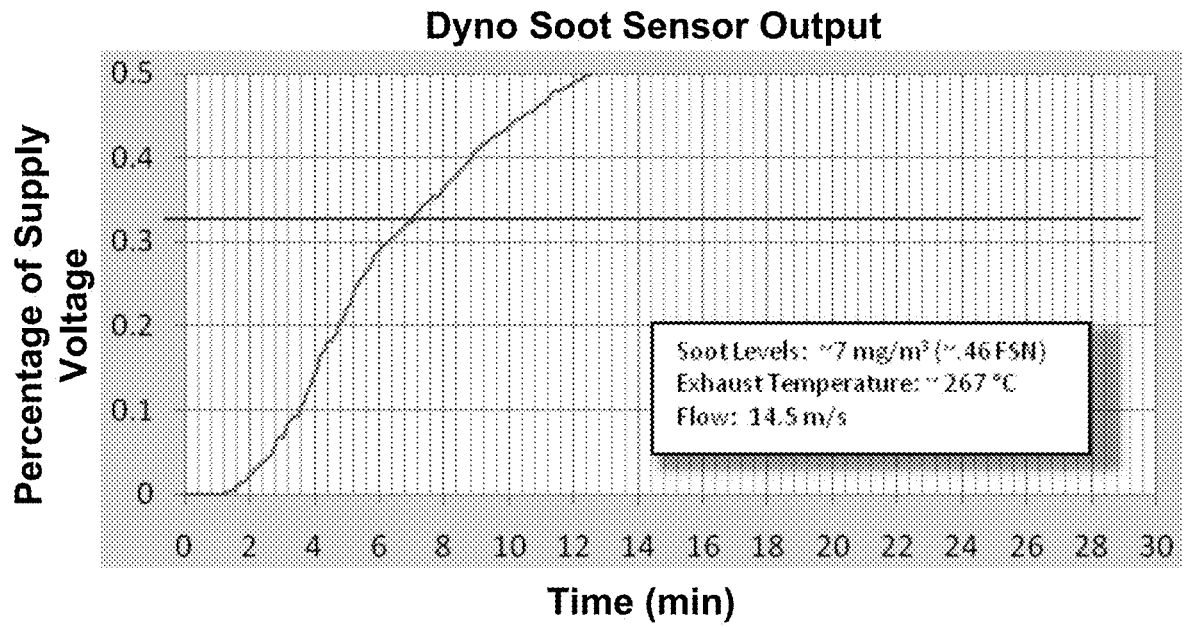
Figure 33D:
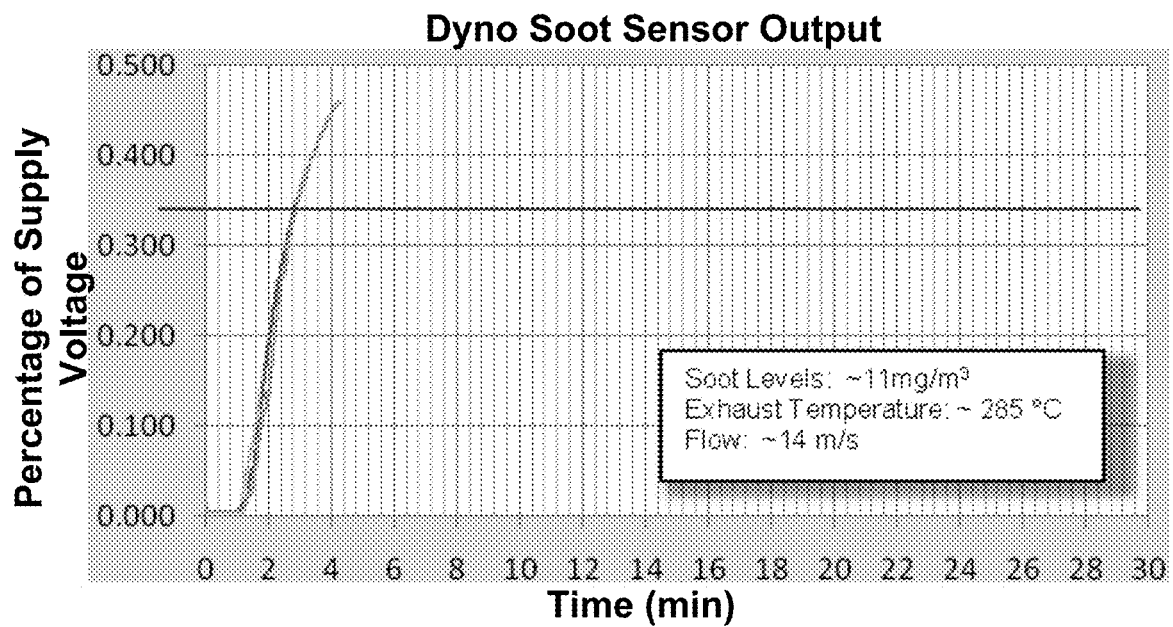

FIG. 32 is a plot of supply wattage vs. air flow rate associated with an exemplary soot sensor consistent with the present disclosure exposed to an exhaust gas having a temperature of 200° C. Embodiments of a soot sensor described herein may be configured to operate in a temperature range of 0° C. to 650° C., with excursions to 950° C. For example, a soot sensor consistent with the present disclosure may be configured to operate in an exhaust gas temperature ranging from 150° C. to 650° C. The wattage required to get the sensor to its regeneration temperature varies with exhaust temperature and flow velocity. The wattage is predictable and repeatable for these different conditions. In the illustrated embodiment, the x-axis illustrates different exhaust velocities and the y-axis illustrates the required wattage for the sensor to reach its regeneration temperature. The wattage is calculated by measuring voltage across the first and second heater elements, as well as any current passing the first and second heater elements. Knowing voltage and current also allows resistance of the heater to be calculated. The resistance vs. temperature curve of the heater is also known. By monitoring the resistance of the heater at regeneration temperature, it can be determined if the heater resistance has changed or drifted out of its acceptable tolerance range.

When the soot sensor is exposed to an exhaust gas stream, certain materials present in the exhaust gas may not be completely incinerated by the heater elements during sensor regeneration. These materials may include ash and/or iron oxide, for example. These materials may build up on the surface of the sensor over time and cause a shift in the response curve of the sensor (Response curve: the change in sensor resistance vs. mg of soot present on the sensor face). Schemes may be implemented to counteract the effect of these materials over time. For example, after dew point is reached, the sensor could be taken through a regeneration cycle and the sensor may store a current resistance in the soot free state. If this resistance is different than previously seen then the offset could be used to compensate for the expected sensor response curve.

In one aspect, the present disclosure may feature a method of predicting soot concentration on a soot sensor. The method may include measuring the time between sensor regenerations and determining the average soot concentration during that time frame. The time between regenerations can be less than a couple minutes to over 20 minutes with typical soot concentration levels. However, with very low soot concentration levels, the time between regeneration cycles can be much longer. The main disadvantage to this method is that it only provides the average soot concentration level over a fairly long time period making it slow, especially at low soot concentration levels.

In another aspect, the present disclosure may feature a method of predicting soot concentration on a soot sensor. This method may be faster in soot concentration determination than the previous method described above. The actual response of the sensor (change in sensor resistance vs. time) is used to calculate the mass of soot that is present on the sensor in smaller slices of time "real time". This method uses the change in resistance vs. time or as measured in change in voltage vs. time.

FIGS. 33A-33D are plots of supply voltage vs. time associated with an exemplary soot sensor consistent with the present disclosure. The curves illustrated in FIGS. 33A-33D are shown with exhaust flow at 15 m/s and exhaust temperature at 270° C. The x-axis is in minutes and the y-axis is percentage of supply voltage. The soot sensor used in each of the curves is coupled to a pull down resistor (shown in FIG. 30B) on the low side. The voltage measurement (output signal) is measured across the pull down resistor. As can most clearly be seen in FIGS. 33A-33D, as soot concentration increases, the slope of the sensors also increases. The horizontal blue line indicates the percentage of supply voltage at which the sensor gets regenerated. The blue line shown was picked to allow the sensor response to be measured primarily in the linear region of the sensor response slope. It is possible to further shorten the time span between sensor regenerations, such as 10% in static states. If the soot concentration is changing a lot (known by slope changes in the sensor curve) then other percentages could be used. This would result in less soot on the sensor allowing regeneration to occur more quickly.

Figure 34:
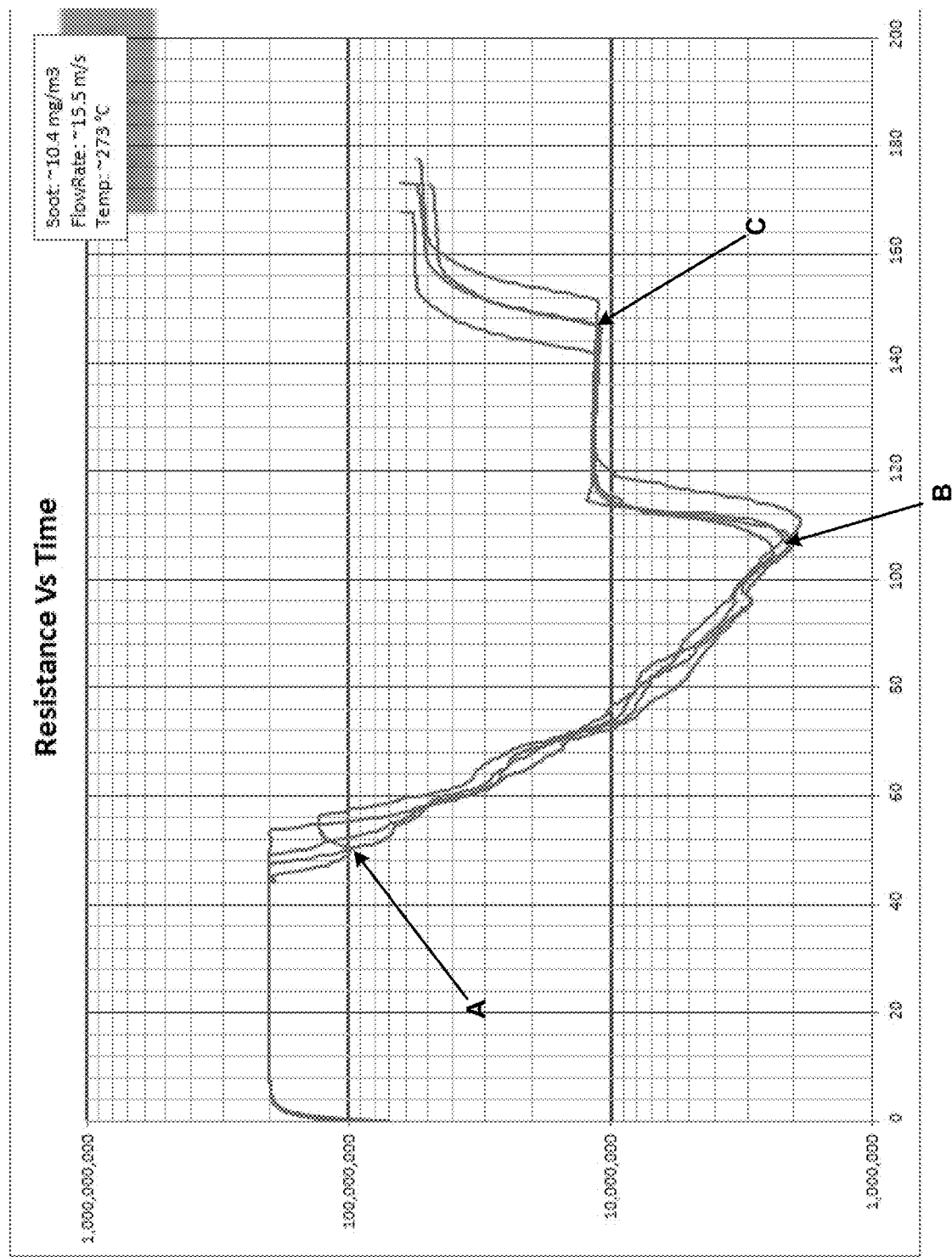
FIG. 34 is a plot of resistance vs. time associated with an exemplary soot sensor consistent with the present disclosure.

FIG. 34 is a plot of resistance vs. time associated with an exemplary soot sensor consistent with the present disclosure. The soot sensor was exposed to an exhaust gas having a known soot concentration of approximately 10.4 mg/m$^3$, a flow rate of approximately 15.5 m/s and a temperature of approximately 273° C. The resistance of the soot sensor was measured through a full cycle (e.g. sensing of soot accumulation through full regeneration of soot sensor). As indicated by arrow A, the sensor resistance begins to drop with soot accumulation. Once a predetermined threshold resistance is reached, as indicated by arrow B, the sensor switches from a soot sense mode to a regeneration mode. As the soot is cleaned from the soot sensor, the resistance begins to increase. As indicated by arrow C, the regeneration mode has ended.

Figure 35:
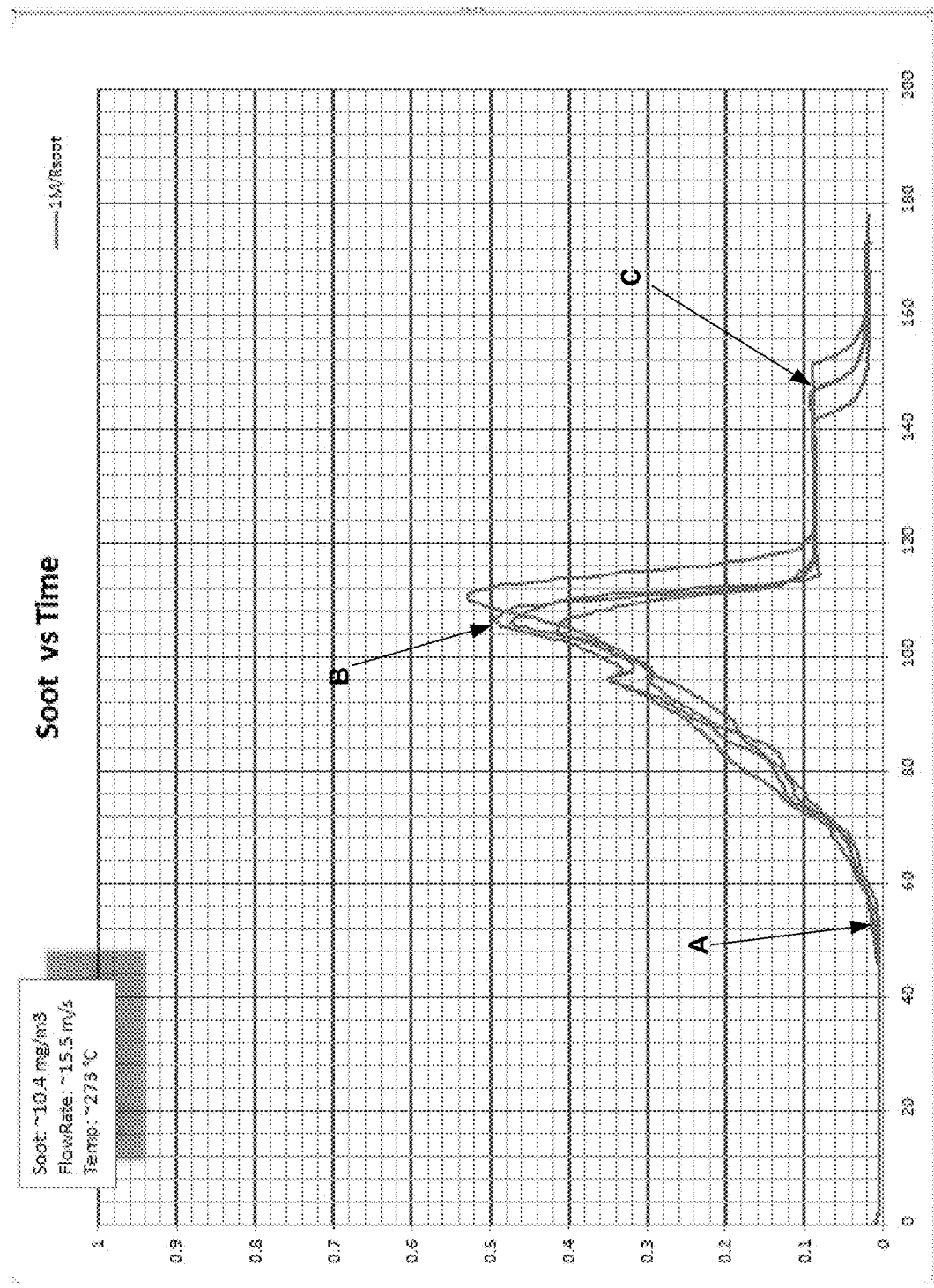
FIG. 35 is a plot of soot accumulation vs. time correlating to the plot of FIG. 34.

FIG. 35 is a plot of soot accumulation vs. time correlating to the plot of FIG. 34. Generally, FIG. 35 is a linearization of the measurement of resistance vs. time of FIG. 34. As shown, soot begins to accumulate at approximately the same time the resistance begins to drop (shown in FIG. 34). Similarly, the moment the soot accumulates and reaches a predetermined threshold, as indicated by arrow B, the regeneration mode begins and the soot accumulation level begins to drop (coinciding with the increase in resistance of FIG. 34). Linearization of the plot of resistance vs. time into soot accumulation vs. time was determined using the formula equation Sensor V out=9206/$\sqrt{R}$, where Sensor V out is the output voltage of the sensor and R is resistance. It should be noted that this is an exemplary formula equation and other equations may be used for the linearization of the plot of FIG. 34.

Figure 36:
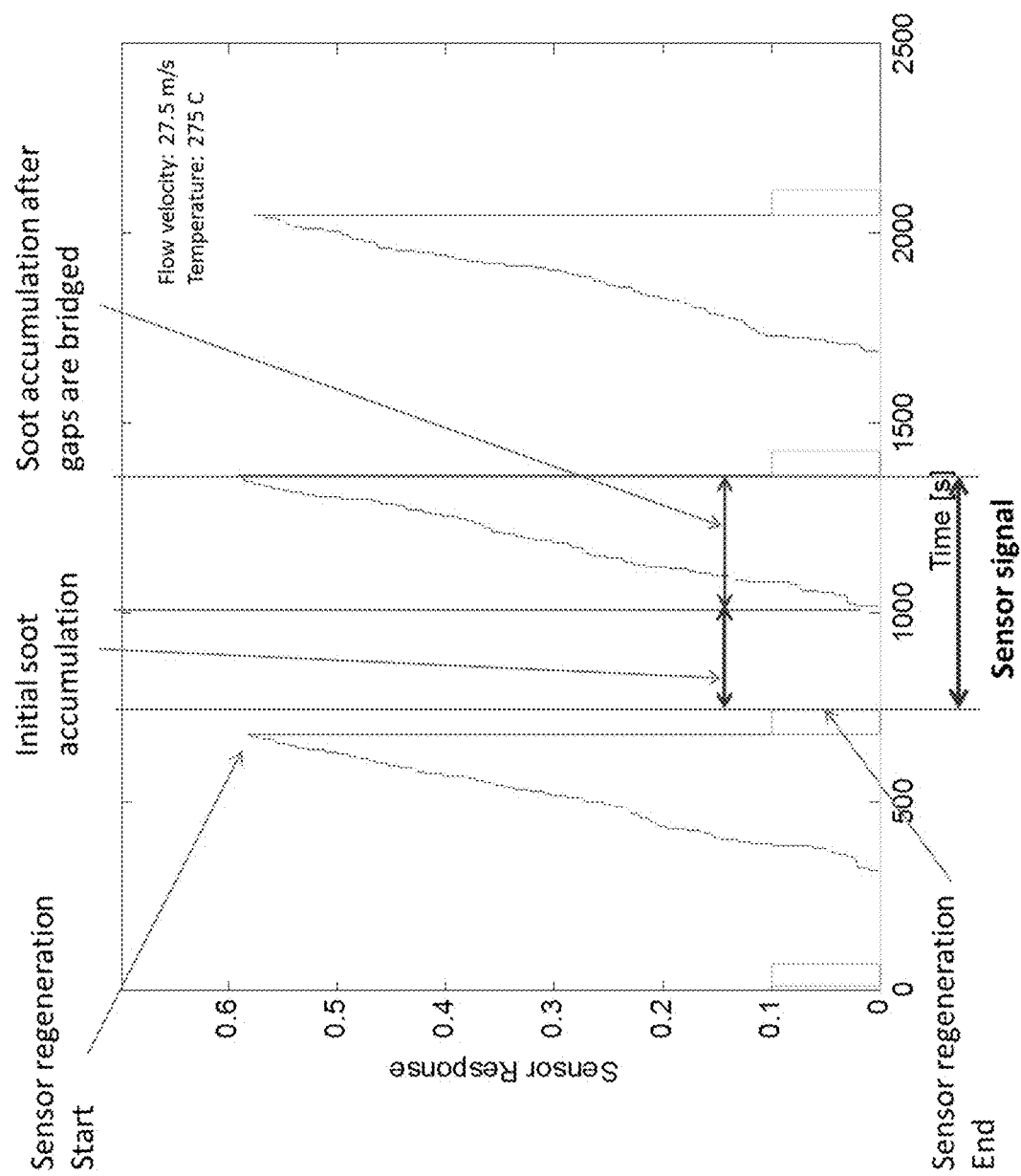
FIG. 36 is a plot of sensor response vs. time associated with an exemplary soot sensor consistent with the present disclosure.

FIG. 36 is a plot of sensor response vs. time associated with an exemplary soot sensor consistent with the present disclosure. The soot sensor was exposed to an exhaust gas having a flow rate of approximately 27.5 m/s and a temperature of approximately 275° C.

Figure 37:
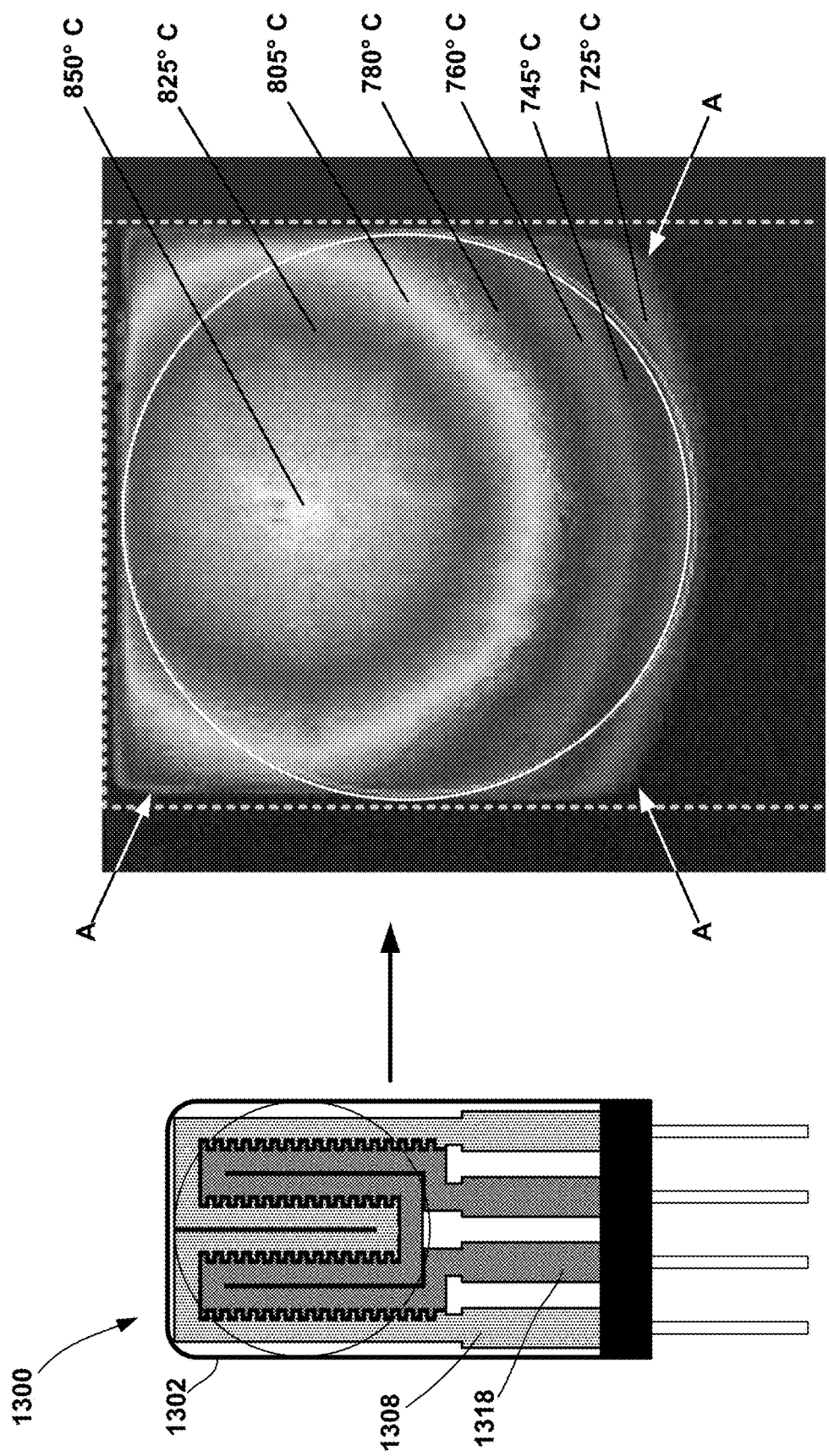
FIG. 37 is a rendering of a temperature gradient of a soot sensor operating in a regeneration mode consistent with the present disclosure.

FIG. 37 is a rendering of a temperature gradient of soot sensor 1300 operating in a regeneration mode consistent with the present disclosure. As previously described, the soot sensor 1300 is configured to operate in a soot sensing mode and a regeneration mode. When in the soot sensing mode, circuitry electrically coupled to soot sensor 1300 is configured to receive input from at least the first and/or second sensor/heater elements 1308, 1318 and further determine soot accumulation on the first and second elements 1308, 1318 and the first surface 1304 of the substrate 1302 based on the received input. The soot sensor 1300 may then transition to the regeneration mode depending, at least in part, on the determined amount of soot accumulation. In particular, the circuitry is configured to control heating of the first and/or second sensor/heater elements 1308, 1318 in response to soot accumulation, wherein the first and/or second sensor/heater elements 1308, 1318 are configured to heat up to a temperature sufficient to remove (e.g. incinerate) accumulated soot from the first surface 1304 of substrate 1302 and the first and/or second sensor/heater elements 1308, 1318, thereby cleaning/regenerating the sensor 1300.

As shown, the soot sensor 1300 exhibits a temperature gradient when operating in the regeneration mode. The first and/or second sensor/heater elements 1308, 1318 may be configured heat to a relatively high temperature, e.g. in the range of approximately 600° C. to 900° C., sufficient to cause accumulated soot particles to incinerate. As shown, the temperature varies across the surface of the substrate 1302, wherein the temperature is highest at or near the center of the substrate 1302 and is lowest at or near the perimeter of the substrate 1302. For example, the temperature at the center is approximately 850° C. near the center of the substrate 1302 and decreases in radial directions extending away from the center, wherein the temperature decreases to approximately 725° C. near one or more edges of the substrate 1302, as indicated by the arrows A.

Due to the temperature gradient and resulting varying temperature across the top surface 1304 of the substrate 1302, the soot sensor 1300 may have to operate in the regeneration mode for a longer period of time and/or heat the first and/or second elements 1308, 1318 to higher temperatures so as to cause soot accumulated in edge areas of the substrate 1302 to fully incinerate and burn off. Operating in the regeneration mode for a longer period of time and/or at higher temperatures may result in a decreased lifespan of the first and/or second elements 1308, 1318, subjecting the soot sensor 1300 to mechanical breakdown and/or requiring more frequent repair or replacement.

Figure 38:
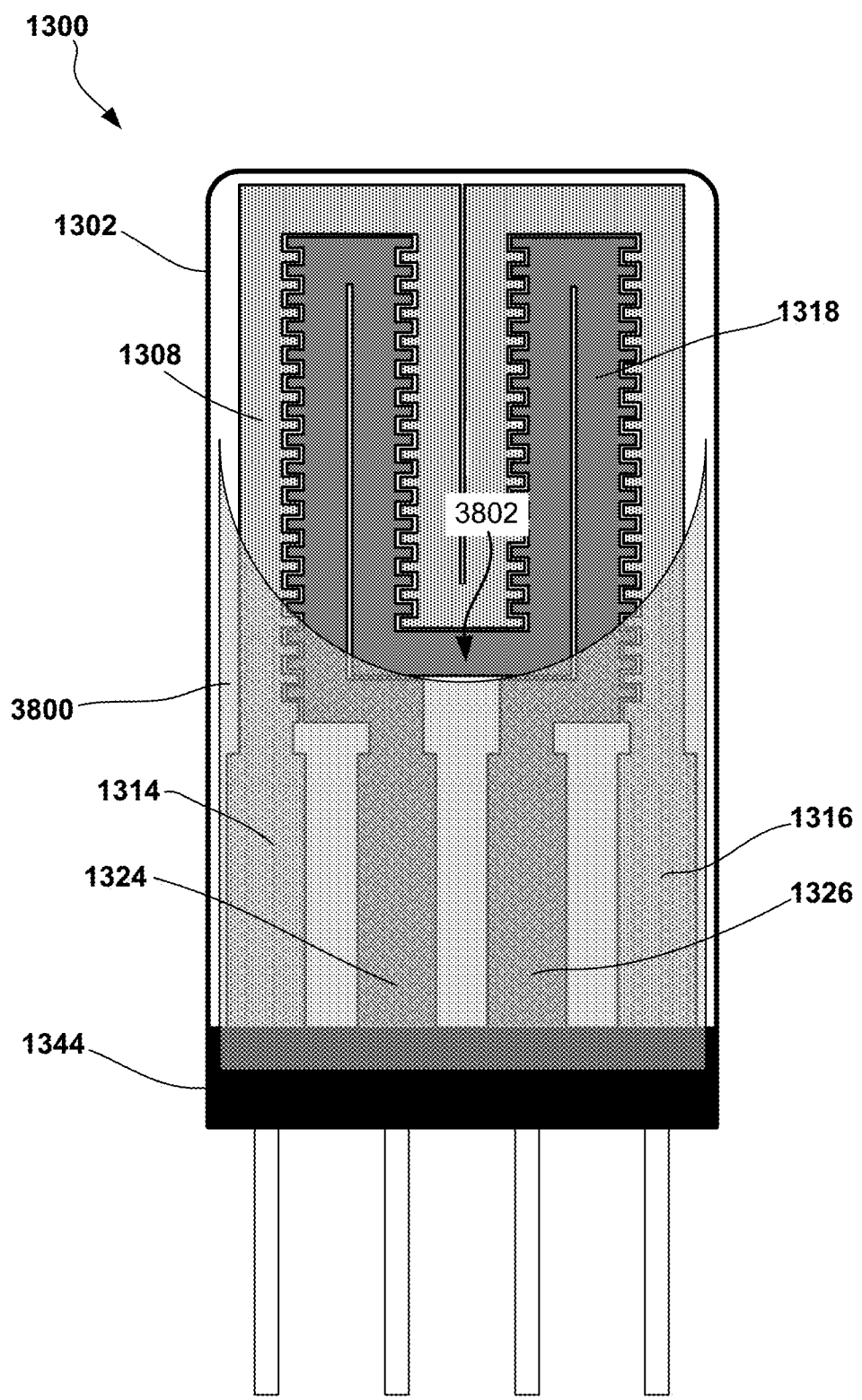
FIG. 38 is a schematic top view of the soot sensor of FIG. 13 including a passivation layer.

FIG. 38 is a schematic top view of the soot sensor of FIG. 13 including a passivation layer 3800. As shown, the soot sensor 1300 may include a pad portion 1344 defining a portion of the first 1314 and second 1316 electrical contacts of the first sensor/heater element 1308 and the first 1324 and second 1326 electrical contacts of the second sensor/heater element 1318. In the illustrated embodiment, the passivation layer 3800 is disposed over a portion of the first surface 1304 of the substrate 1302 and may cover portions of the pad portion 1344, including the first 1314, 1324 and second 1316, 1326 electrical contacts of the first and second elements 1308, 1318, respectively. Furthermore, the passivation layer 3800 may be shaped and/or sized to cover portions of the first and second elements 1308, 1318 in a desired pattern. For example, the passivation layer 3800 may include a portion 3802 shaped and/or sized to compliment the geometry of the temperature gradient pattern. As shown, portion 3802 has a generally concave geometry that is complimentary to the pattern of the temperature gradient shown in FIG. 37. It should be noted that the portion 3802 may include a variety of different shapes and/or dimensions that are specifically tailored to a temperature gradient exhibited.

The passivation layer 3800 is configured to shield the covered portions of the soot sensor 1300 (e.g. first and second elements 1308, 1318, surface of the substrate 1302, etc.) from exposure to and accumulation of soot particles thereon. The passivation layer 3800 may therefore shield some edge areas of the soot sensor 1300 from being exposed to soot particles, thus preventing accumulation of soot in these difficult to heat areas. By including a portion 3802 corresponding to the temperature gradient pattern, the passivation layer 3800 may allow soot to only accumulate on the exposed portions of the soot sensor 1300 where, during the regeneration mode, the temperature is at an acceptable level sufficient to incinerate soot in an acceptable time frame. Accordingly, the inclusion of the passivation layer 3800 may decrease the time required to operate in the regeneration mode as well as the overall temperature required so as to fully burn off soot from the substrate 1302.

The passivation layer 3800 may include non-conductive and/or electrically insulating materials. Materials may include oxides, including, but not limited to, alumina, zirconia, yttria, lanthanum oxide, silica, and/or combinations including at least one of the foregoing, or any like material capable of inhibiting electrical communication. Additionally, the passivation layer 3800 may include materials configured to provide thermal insulation. In the illustrated embodiment, the passivation layer 3800 may include a thick film glass.

Figure 39:
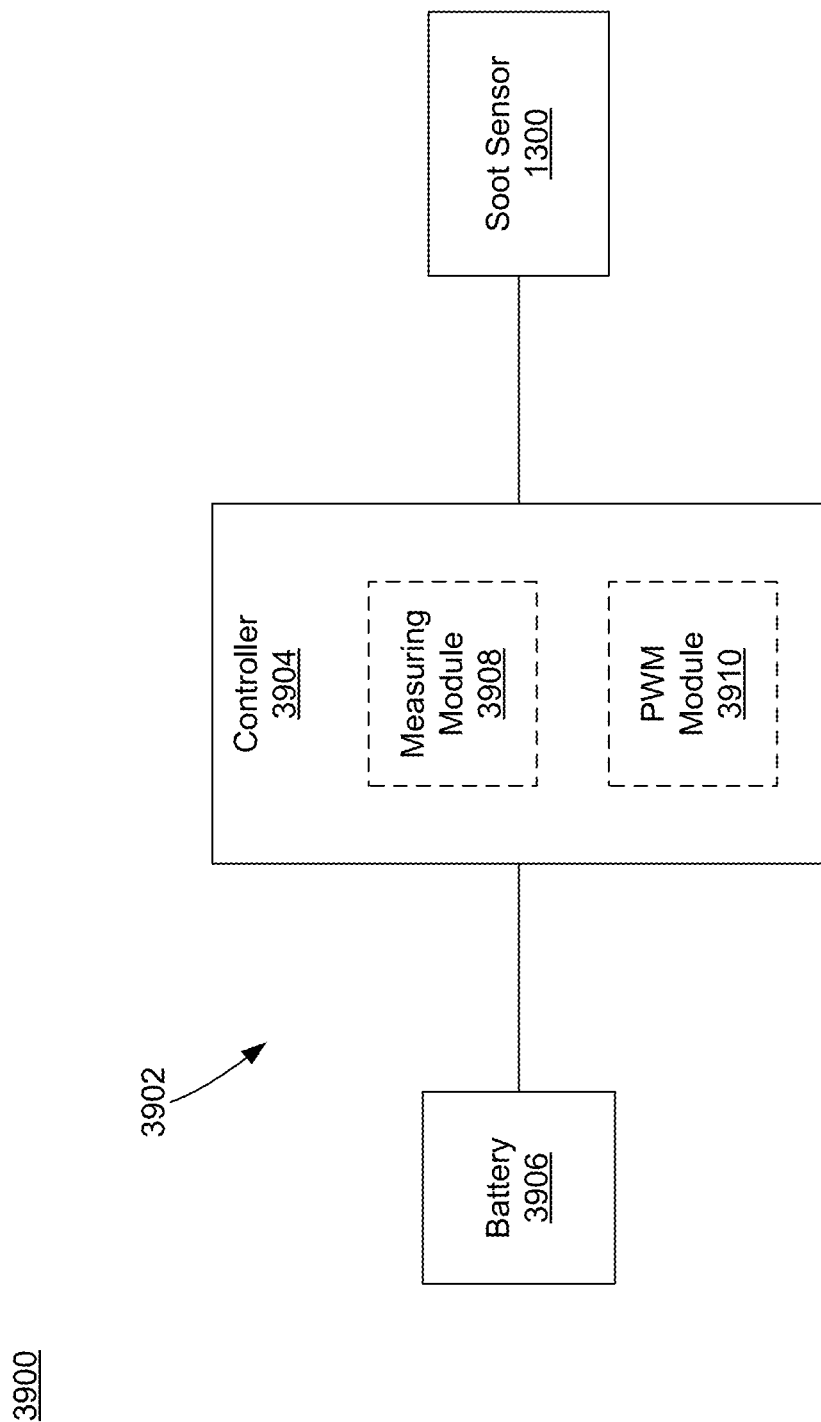
FIG. 39 is a block diagram of another exemplary embodiment of a soot sensor system consistent with the present disclosure.

FIG. 39 is a block diagram of another exemplary embodiment of a soot sensor system 3900 consistent with the present disclosure. As shown, the soot sensor system 3900 includes soot sensor 1300. It should be noted, however, that the soot sensor system 3900 may include other embodiments of a soot sensor consistent with the present disclosure. The soot sensor system 3900 further includes circuitry 3902 electrically coupled to the soot sensor 1300 and configured to provide power to and control operation of the soot sensor 1300. For example, the system 3900 may include a controller 3904 coupled to and configured to communicate with the first and second elements 1308, 1318 for providing currents $I_{sense}$, $I_{heater1}$ and/or $I_{heater2}$ thereto. The current may be supplied by a power source, such as, for example, a battery 3906.

The controller 3904 includes a measuring module 3908 and a pulse-width modulating (PWM) module 3910. During a soot sensing mode, a voltage may be applied the first and/or second elements 1308, 1318 and the measuring module 3908 may be configured to measure a resulting value of the current $I_{sense}$. The soot sensing mode generally occurs during an off-time of the PWM switch module 391. As previously described, the value of the current $I_{sense}$ through the first and/or second elements 1308, 1318 may be utilized to determine an amount of soot that has been deposited on the soot sensor 1300, which may be further indicative of an amount of soot in an exhaust stream communicating with the sensor 1300. When soot is deposited on the first and/or second elements 1308, 1318, the electrical resistance of the conductive path changes, which results in a corresponding change in $I_{sense}$. The value of $I_{sense}$ is representative of the amount of soot that has been deposited on the sensor 400. For example, as the soot particles build up on the soot sensor 1300 over time, the resistance between the first and/or second elements 1308, 1318 generally decreases from very high G Ohms to approximately 1 M Ohms. The time required for the soot to accumulate on the sensor 1300 relates to the measurement of the concentration of exhaust gas soot.

Generally, a method of sensing soot accumulation consistent with the present disclosure may include applying a variable voltage during the soot sensing mode. For example, a relatively high voltage, e.g. within the range of 5 to 60V, may be initially applied to the first and/or second elements 1308, 1318 at the initiation of the soot sensing mode. In one embodiment, the initial voltage may be 42V. The use of a high voltage, particularly during a cold start, is advantageous in that soot particles become charged at higher voltages and are therefore more attracted to the first and/or second elements 1308, 1318. In turn, the soot sensor may have increased sensitivity and may detect soot accumulation faster and result in faster response and regeneration. After a predetermined period of time, the controller 3904 may be configured to decrease the voltage applied to the elements 1308, 1318, thereby resulting in less noise. The controller 3904 is configured to determine the appropriate voltage based, at least in part, on the temperature of the exhaust, for example. For example, when the exhaust temperature is relatively low, the controller 3904 may be configured to apply a higher voltage, and vice versa.

When a threshold amount of soot accumulates on the first and/or second elements 1308, 1318, e.g. as determined by reaching a threshold value of $I_{sense}$, the controller 3904 is configured to initiate a regeneration mode. In order to heat up the first and/or second elements 1308, 1318, a relatively high current is passed through at least one of the first and second elements 1308, 1318. In the illustrated embodiment, the PWM switch module 3910 is configured to control the current applied to the first and/or second elements 1308, 1318 during an on-time of the PWM switch. In particular, the first and/or second elements 1308, 1318 are excited (e.g. heated) based on a PWM signal provided by the PWM switch module 3910.

The PWM switch module 3910 is configured to provide current $I_{heater1}$ and/or current $I_{heater2}$ to the first and/or second element 1308, 1318, respectively to initiate the regeneration mode. During the regeneration mode, the first and/or second elements 1308, 1318 are configured to heat to a desired temperature at which accumulated soot particles may incinerate, thereby clearing soot particles from the soot sensor 1300. Because the first and/or second elements 1308, 1318 are excited based on PWM signals from the PWM switch module 3910, soot accumulation may be determined during the regeneration mode. Accordingly, as described in greater detail herein, the controller 3904 may be configured to provide staged heating of the soot sensor 1300, wherein operation of the first and/or second elements 1308, 1318 in the regeneration mode may be controlled (e.g. start, stop, pause, change between modes, etc.) in real-time or near real-time and soot accumulation sensing may occur intermittently during the regeneration process so as to determine the effectiveness of the regeneration process in burning off soot from the soot sensor 1300.

Generally, a method of sensing soot accumulation consistent with the present disclosure may further a rationality test initiated during, or shortly after, active regeneration of a diesel particulate filter (DPF). A DPF is a device designed to remove diesel particulate matter or soot from the exhaust gas of a diesel engine. Some filters are single-use and intended for disposal and replacement once they are full of accumulated ash, while some filters are designed remove accumulated soot from the filter via regeneration. Regeneration of the filter is performed either passively (e.g., from the engine's exhaust heat in normal operation or by adding a catalyst to the filter) or actively by introducing very high heat into the exhaust system. For example, a system may include engine programming to run when the filter is full in a manner that elevates exhaust temperature or produces high amounts of $NO_x$ to oxidize the accumulated ash.

As previously described, a soot sensor consistent with the present disclosure may be positioned upstream or downstream from a DPF. The soot sensor may be configured to perform a rationality test during, or shortly after, active regeneration of the DPF so as to determine whether the soot sensor is operating correctly. In particular, during, or shortly after, active regeneration of the DPF, soot imparted upon the sensor may generally be at a low level. Similar to the variable voltage method described earlier, a relatively high voltage may be initially applied to the first and/or second elements 1308, 1318 at the initiation of the soot sensing mode. The use of a high voltage, particularly during a cold start, is advantageous in that soot particles become charged at higher voltages and are therefore more attracted to the first and/or second elements 1308, 1318. In turn, the soot sensor may have increased sensitivity, particularly accounting for the low level of soot accumulation due in part to the active regeneration of the DPF.

Generally, effective regeneration of the soot sensor is a function of temperature and time. Although time is a variable that may be controlled (e.g. by way of the controller 3904) temperature is a variable that may only be inferred based on the voltage of the power source (e.g. battery 3906) and/or the duty cycle of the PWM module 3910. The inability the accurately measure temperature may ultimately result in incomplete regeneration of the soot sensor due to ineffective temperature (e.g. failure to burn all soot from the sensor due to too low of a temperature) and/or thermal overstressing of the soot sensor due to the use of high temperature for extended periods of time to achieve complete regeneration.

Figure 40:
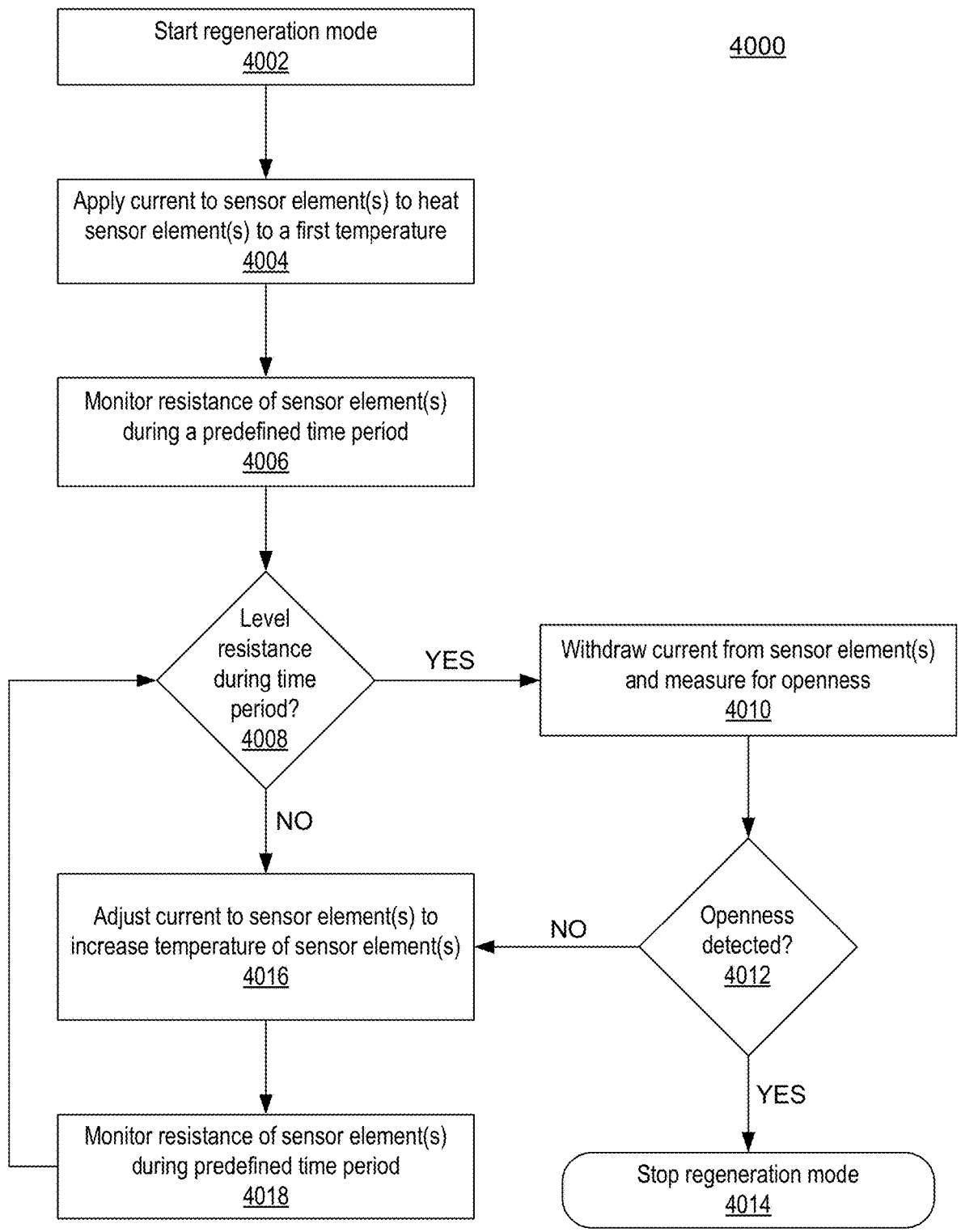
FIG. 40 is a flow diagram illustrating one embodiment of operating a soot sensor in a regeneration mode and determining regeneration effectiveness consistent with the present disclosure.

FIG. 40 is a flow diagram illustrating one embodiment of a method 4000 of operating a soot sensor in a regeneration mode and determining effectiveness of the regeneration consistent with the present disclosure. As previously described, the controller 3904 is configured to sense soot accumulation during regeneration of the soot sensor 1300. Accordingly, the controller 3904 may be configured to provide gradual heating of the first and/or second elements 1308, 1318 of the soot sensor 1300 and further sense soot accumulation at different temperature levels so as to determine regeneration effectiveness for different temperature levels.

The method 4000 includes starting a regeneration mode (operation 4002) and applying a current to the first and/or second elements 1308, 1318 to heat the elements to a first temperature (operation 4004). In one embodiment, the first temperature may be approximately 775° C. The temperature may be measured by any known method or technique for determining temperature of the elements. Upon reaching the first temperature, the resistance of the elements 1308, 1318 is monitored for a predefined time period (operation 4006). For example, the measuring module 3908 may monitor the resistance levels between at least one of the first and second elements 1308, 1318 during an off-time of the PWM module 3910. During the monitoring of the resistance of the elements, a determination may then be made in operation 4008 as to whether the resistance leveled out during the predefined time period (e.g., whether the slope of the resistance has remained substantially constant during the predefined time period). The resistance may be monitored for a predefined time period of at least 20 second and the resistance is deemed to be leveled out if the slope of the resistance remains relatively constant for a predetermined portion of the 20 second time period, such as for 10 seconds. For example, the resistance may be monitored for a predefined time period of 70 seconds and the resistance is deemed to be leveled out if the slope of the resistance remains relatively constant for 40 seconds of the 70 second time period. Of course, it should be appreciated that the length of the monitoring period and/or the length during which the resistance is deemed to be substantially constant may vary depending on the application.

If it is determined in operation 4008 that the resistance leveled out during the time period, then current is withdrawn from the elements and the elements are then measured for openness (operations 4010). During the measuring of the elements, a determination is then made in operation 4012 as to whether openness was detected. If it is determined that openness is detected, then the regeneration mode will be stopped (operation 4014).

If it is determined in operation 4008 that the resistance failed to level out during the time period, then the current applied to the elements is adjusted so as to increase the temperature of the elements (operation 4016). Similarly, if it is determined in operation 4012 that openness was not detected, then the current applied to the elements is adjusted so as to increase the temperature of the elements (operation 4016). Generally, temperature is increased in a stepwise fashion, such that temperature increases in predefined increments, such as 25° C. increments. As such, the elements would increase in temperature from 775° C. to 800° C. Upon increasing the temperature of the elements to the next increment, the resistance of the elements is monitored for the predefined time period (operation 4018). As shown, upon completing operation 4018, determination 4008 may then repeat to determine whether the resistance leveled out during the time period. If it is determined that the resistance leveled out, operation 4010 and determination 4012 may then repeat and if it is determined that the resistance failed to level out, operations 4016 and 4016 may then repeat. In this method, there may be a limited number of predefined temperature increments based on a maximum temperature that the elements may be heated to. For example, the maximum temperature may be 825° C. As such, the temperature will never be increased past the 825° C. temperature and, once adjusted to the 825° C., the current may be immediately withdrawn and the openness of the elements may be checked, regardless of whether the resistance leveled out or not.

The method 4000 of applying gradual heating of the sensor described above provides numerous advantages. For example, the method may solve the tradeoff between over-stressing the sensor/heater elements due to high temperature and no fully burning off soot from the substrate. Furthermore, the method may help drive cycle requirements, including requirements are that the soot sensor be able to sense and regenerate in a standard drive cycle defined by FTP (US), NEDC (EU), WHTC (Trucks), etc.

While FIG. 40 illustrates method operations according various embodiments, it is to be understood that in any embodiment not all of these operations are necessary. Indeed, it is fully contemplated herein that in other embodiments of the present disclosure, the operations depicted in FIG. 40 may be combined in a manner not specifically shown in any of the drawings, but still fully consistent with the present disclosure. Thus, claims directed to features and/or operations that are not exactly shown in one drawing are deemed within the scope and content of the present disclosure.

As previously described, accurate temperature measurement may play a key role in achieving effective regeneration of the soot sensor. The following describes a method of accurately determining the temperature during the regeneration process based on the electrical characteristics of the substrate of the soot sensor. In particular, in order to increase the accuracy of temperature measurement during regeneration (i.e. determining the temperature at which regeneration is occurring) the electrical characteristics of the substrate of a soot sensor consistent with the present disclosure is measured based on solid state conduction principles.

As generally understood, in order for current to flow, electrons must necessarily be present in the conduction band of an atom. Insulators generally include a filled valence band and an empty conduction band, wherein there exists a large band energy gap between the valence and conduction band. At room temperatures, very few electrons achieve enough random thermal energy to "jump" the gap to the conduction band. This results in low conduction or high resistance for the material (i.e. the definition of an insulator).

As the temperature of the material increases, more electrons achieve enough thermal energy bridge the gap and reach the conduction band. With little or no external field applied across the insulator, an equilibrium may results (e.g. the higher the temperature, the greater the number of electrons in the conduction band). This relationship was first postulated by Svante Arrhenius in a classical empirical relationship showing the temperature dependence of chemical reactions (as well as the number of conduction electrons).

If an electric field is suddenly applied across a sample of the insulation material, there will be an inrush of electrons flowing, followed by a gradual decrease, as a new equilibrium is reached. The decay in this current is exponential and, as such, the amplitude of this exponential waveform, at a given applied electric field, is dependent of the absolute temperature of the insulator. Because of this effect, the initial dynamic resistance of a substrate of a soot sensor consistent with the present disclosure is generally low, particularly at high substrate temperatures (e.g. above 600° C.). This type of effect is illustrated in *Temperature Dependent Dielectric Properties of Polycrystalline 96% Al2O32*, NASA Glenn Research Center at Lewis Field, Cleveland, Ohio 44135.

During a regeneration cycle, the temperature of the substrate can be approximated by periodically sampling the substrate conduction as the substrate is being heated. As previously described, the substrate may be heated when a voltage (e.g. 40 Hz PWM voltage) is applied to the sensor/heater elements. The temperature of the substrate may be measured during the PWM signal "off" time, by measuring the resistance of the heater element itself. The resistance of the heater element is proportional to the temperature of the substrate. At higher temperatures the resistance of the heater element becomes higher.

In the event that the regeneration cycle has not completely removed accumulated soot particles from the soot sensor (i.e. the sensor remains contaminated or poisoned), the conduction of the soot coating may result in a heater element resistance measurement indicating that the temperature of the substrate is higher than it really is. By taking advantage of the initial inrush current, which is relatively independent of the soot coating on the substrate, the conduction of the substrate may be initially low enough to negate the shunting effect of the soot coating. This was found to be true at temperatures above 600° C. and contamination resistances greater than 10 M Ohms.

Figure 41:
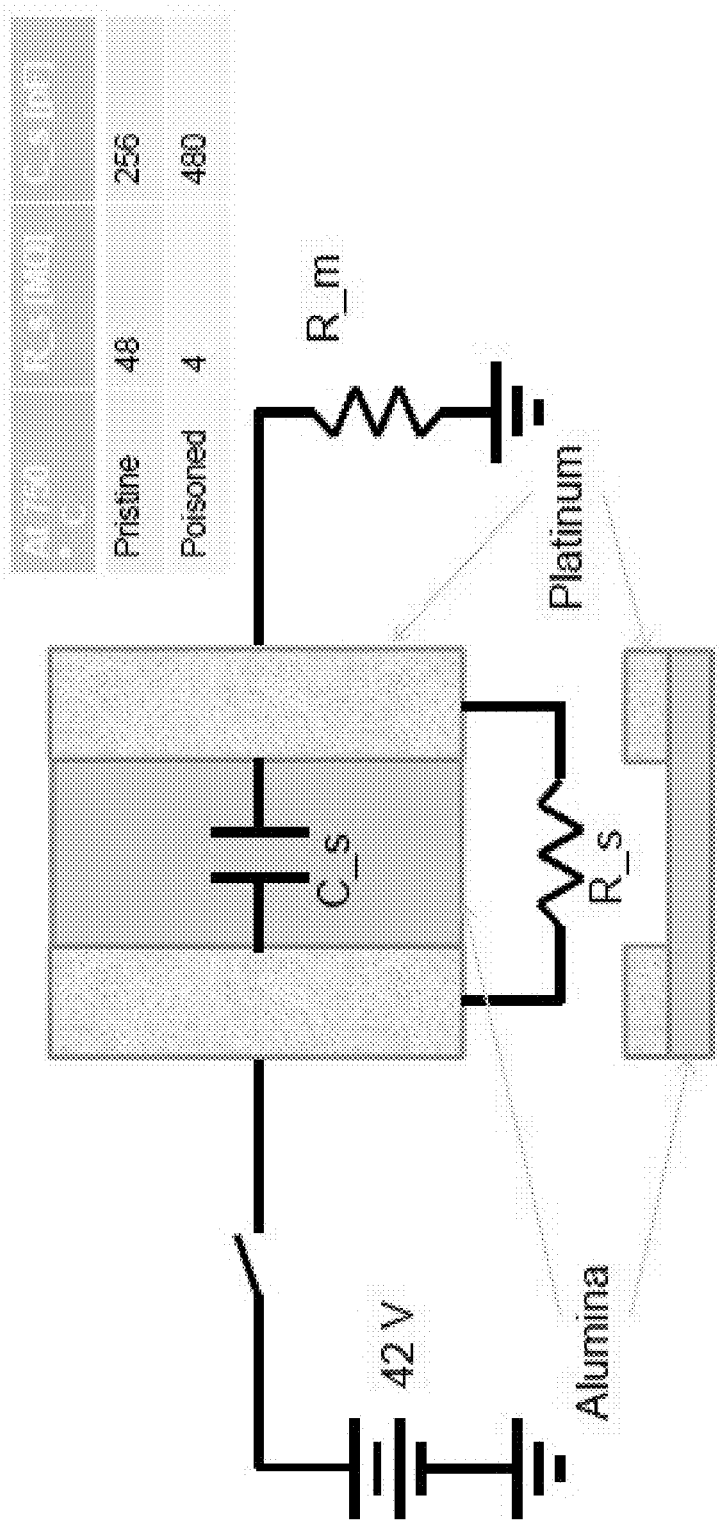
FIG. 41 is a model of a substrate consistent with the present disclosure illustrating the substrate resistance, the sensor capacitance and the measurement resistance.

To detect contamination of the substrate, e.g. following regeneration, a system consistent with the present disclosure may utilize an impedance check. FIG. 41, for example, shows a model of an Alumina substrate consistent with the present disclosure wherein $R\_s$ is the resistance of the substrate, $R\_m$ is the measurement resistance, and $C\_s$ is the sensor capacitance. As shown, for example, a pulse, e.g. a 42 V pulse, may be applied to the substrate while substrate is heated to measure any leakage resistance or any capacitance due to any poisons from exhaust system or any loss of gain or offset in the circuit. It has been shown that certain ceramics like Alumina develop lower resistance and higher dielectric constant with increase in temperature (see paper: *Temperature Dependent Dielectric Properties of Polycrystalline 96% Al2O32* NASA Glenn Research Center at Lewis Field, Cleveland, Ohio 44135). A system consistent with the present disclosure may take advantage of both DC resistance change and also dielectric change (capacitive effect) at higher temperatures to sense any loss of gain or offset. In other words, the impedance of ceramic changes with temperature (both resistive and capacitive properties) and a circuit measures this impedance at higher temperatures. Any loss of gain or offset resulting from poisons that may cover the sensor surface will show up in impedance measurement.

Examples of measurements for R_s and C_s for both a clean/pristine sensor and contaminated/poisoned sensor are provided in FIG. 41. As shown, the contaminated/poisoned sensor exhibits lower substrate resistance but higher sensor capacitance compared to a pristine sensor at the same substrate temperature.

Figures 42A, 42B:
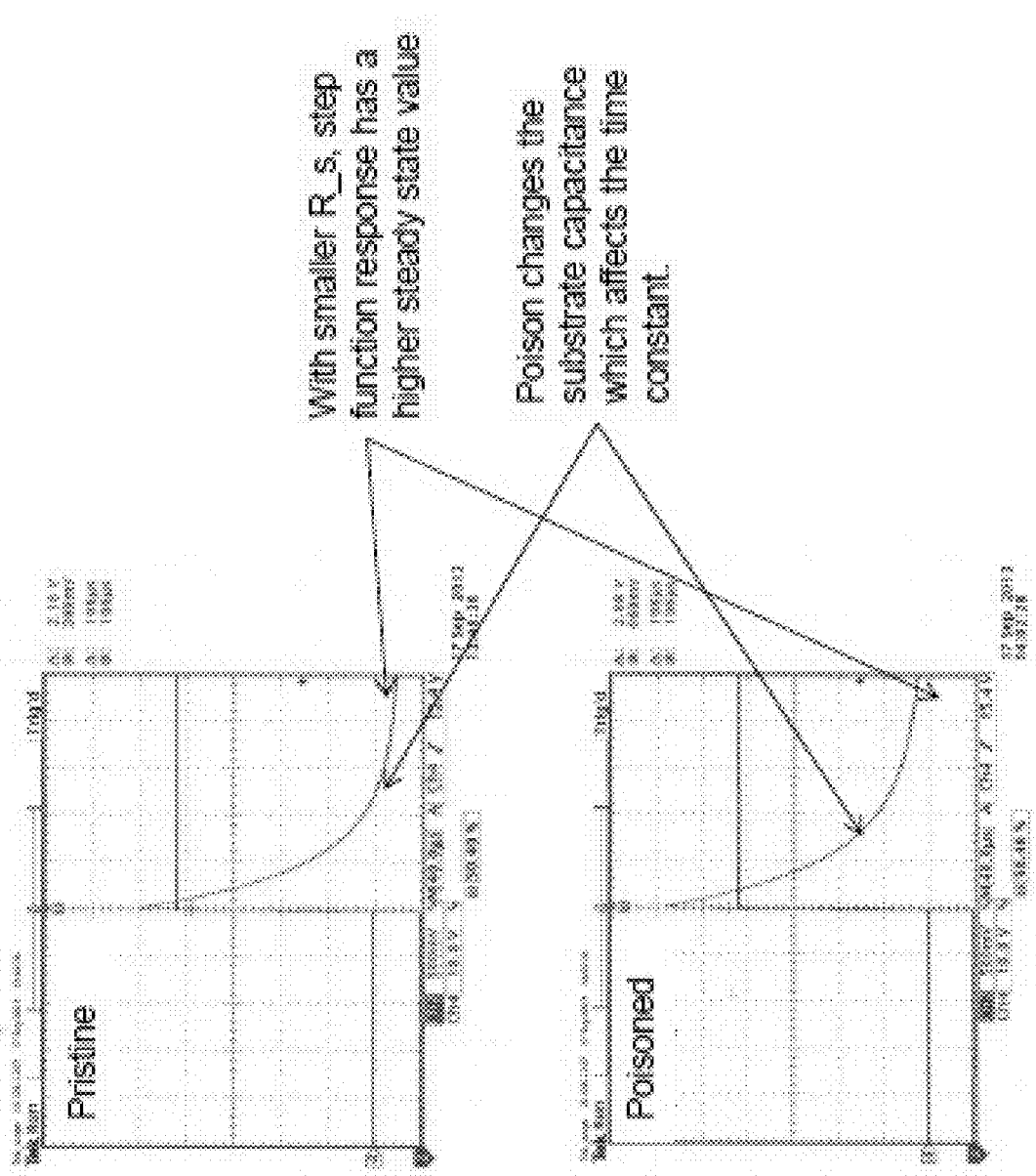
FIGS. 42A and 42B include plots of voltage vs. time for pristine/clean and contaminated/poisoned sensors, respectively.

FIGS. 42A and 42B includes plots of voltage vs. time across the measurement resistance R_m shown in FIG. 41 for pristine/clean and contaminated/poisoned sensors, respectively, when a 42 V step is applied across the first and/or second elements (e.g. first and second sensor/heater elements 1308, 1318) on an alumina substrate 1302 of the soot sensor 1300 at a temperature of approximately 750 C. As shown, both the decay shape/time constant and final steady state values are different for clean versus poisoned part. A system consistent with the present disclosure may use this information to detect contamination of a sensor.

Figure 43:
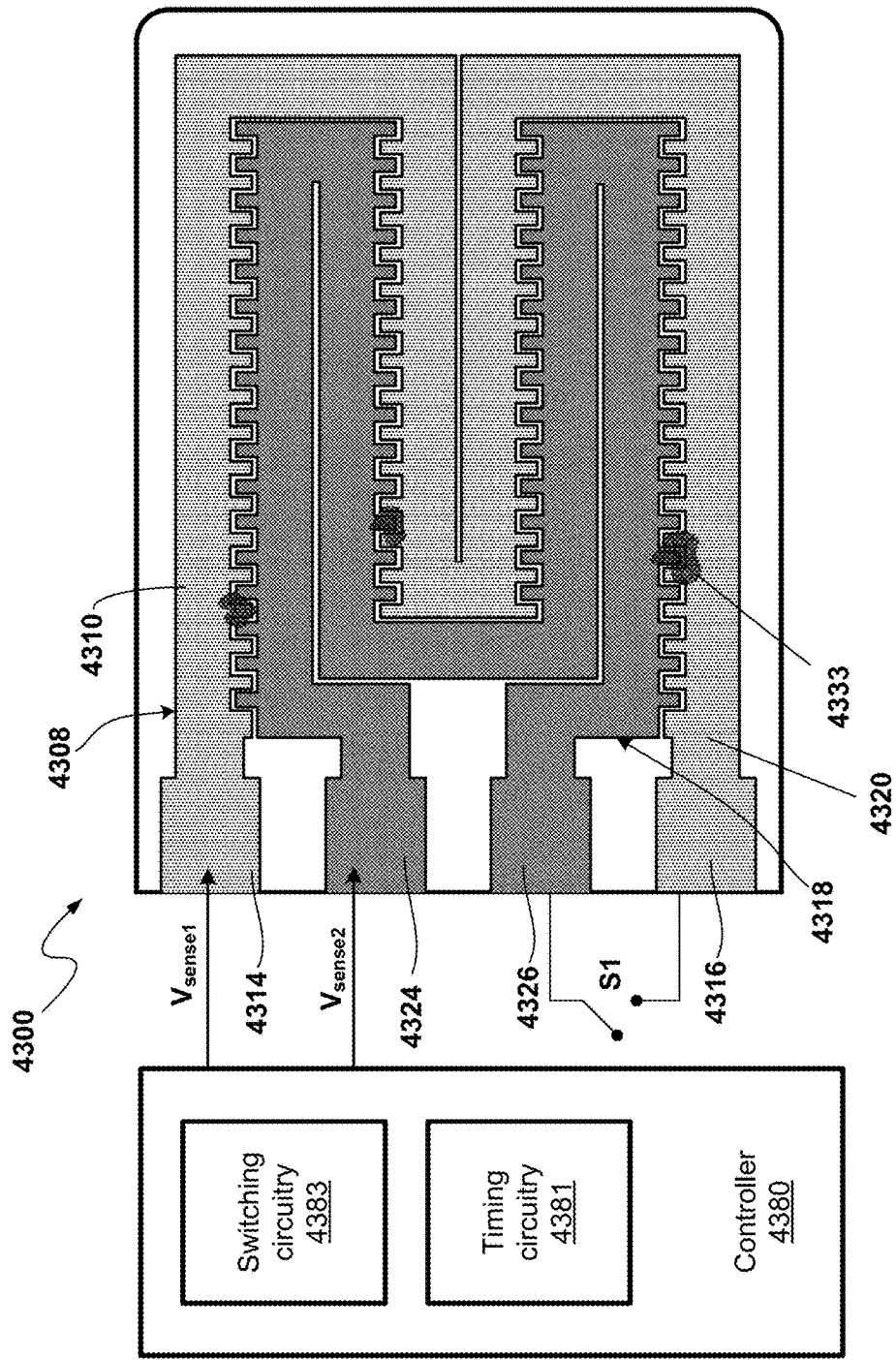
FIG. 43 is a schematic view of another embodiment of a soot sensor and circuitry consistent with the present disclosure.

With reference to FIG. 43, one embodiment of a soot sensor 4300 having adjustable and/or variable sensing voltages is generally illustrated. As discussed herein, soot sensors according to at least one embodiment of the present disclosure may be more sensitive at higher voltage (e.g., but not limited to, 40 V). This is due, at least in part, to a larger electric field created at higher sensing voltages and the resulting attraction of soot particles. Testing shows that soot particles are attracted to the higher voltage electrode and slowly migrate to the electrode at lower potential (e.g., but not limited to, ground). The soot migration usually takes time, and in some instances, many seconds. As described in greater detail herein, the soot sensor 4300 is configured to apply adjustable and/or variable sensing voltages to the first and second sensor/heater elements 4308, 4318 that are different and vary over time.

The soot sensor 4300 includes a substrate 4302 defining a first surface 4304 (e.g. a top surface, similar to first surface 404 of soot sensor 400) and a second surface (not shown) (e.g. a bottom surface, similar to second surface 406 of soot sensor 400) opposing the first surface 4304. A first sensor/heater element 4308 and a second sensor/heater element 4318 are formed on the first surface 4304. As described herein, the soot sensor 4300 may be configured to operate in a first mode (hereinafter referred to as "soot sensing mode"), wherein the first and second sensor/heater elements 4308, 4318 are configured to sense soot accumulation on at least the first surface 4304 of the soot sensor 4300. The soot sensor 4300 may be further configured to operate in a second mode (hereinafter referred to as "regeneration mode"), wherein the first and second sensor/heater elements 4308, 4318 are configured to heat and remove (e.g. incinerate) at least a portion of accumulated soot on the first surface 4304, thereby cleaning/regenerating the sensor 4300.

The first and second sensor/heater elements 4308, 4318 each include at least one continuous loop of conductive material 4310, 4320, respectively, disposed on the substrate 4302. Similar to the embodiment of FIG. 4, the loops 4310, 4320 may be arranged in a serpentine configuration including first and second sets of undulations 4312, 4322, respectively. As shown, the first sensor/heater element 4308 includes first 4314 and second 4316 electrical contacts at opposite ends of the loop 4310 configured for coupling to circuitry for providing current through the loop 4310. Similarly, the second sensor/heater element 4318 includes first 4324 and second 4326 electrical contacts at opposite ends of the loop 4320 configured for coupling to circuitry for providing current through the loop 4320.

The first and second sensor/heater elements 4308, 4318 may be configured to operate separately and independently from one another, as described in regards to the embodiment of FIG. 4. Additionally, the soot sensor 4300 may further include a switch S1 coupled to the second electrical contacts 4316, 4326 of the first and second sensor/heater elements 4308, 4318, respectively, for selectively coupling and decoupling the contacts 4316, 4326. For example, when the switch S1 is open, the first and second sensor/heater elements 4308, 4318 may operate separately from one another. When the switch S1 is closed, the first and second sensor/heater elements 4308, 4318 may be electrically coupled to one another, establishing a continuous loop of conductive material between contacts 4314 and 4324.

The first and second sensor/heater elements 4308, 4318 may include electrically conductive materials or metals, such as, alumina, gold, platinum, osmium, rhodium, iridium, ruthenium, aluminum, titanium, zirconium, and the like, as well as, oxides, alloys, and combinations including at least one of the foregoing metals. In one embodiment, the elements 4308, 4318 may include alumina having a film platinum trace deposited on a portion thereof.

The substrate 4302 may include non-conductive and/or electrically insulating materials. Materials may include oxides, including, but not limited to, alumina, zirconia, yttria, lanthanum oxide, silica, and/or combinations including at least one of the foregoing, or any like material capable of inhibiting electrical communication and providing structural integrity and/or physical protection. Additionally, the soot sensor 4300 may include thick film and/or thin film constructions.

The soot sensor 4300 may also include adjustable and/or variable sensing voltage controller 4380. The controller 4380 may include timing circuitry 4381 and/or switching circuitry 4383 configured to cause adjustable and/or variable sensing voltages that vary over time to be applied to the first and second sensor/heater elements 4308, 4318. For example, the controller 4380 is configured to cause a higher voltage to be applied to the first sensor/heater element 4308 compared to the second sensor/heater element 4318 for a first time period, and then cause a higher voltage to be applied to the second sensor/heater element 4308, 4318 compared to the first sensor/heater element 4308 for a second time period. The switching interval(s) between the higher voltage(s) and lower voltage(s) may be selected to occur at certain frequency(s) to allow soot particles to be attracted to both the first and second sensor/heater elements 4308, 4318 (instead of one) and thus reduce the migration time from one sensor/heater element to the other, thereby allowing the soot sensor 4300 to have a faster response time as well as increased sensitivity.

The timing circuitry 4381 may be configured to generate switching interval(s) that occur at one or more fixed (i.e., selected) time periods (e.g., but not limited to, 0.1 Hz) and/or may generate switching interval(s) that dynamically change (e.g., be selected and/or adjusted) based one or more operating parameters such as, but not limited to, soot accumulation levels, high voltage(s), low voltage(s), temperature, air flow rates, desired sensitivity, desired power consumption, and/or response time. It should be appreciated that the switching interval(s) may be discrete (e.g., the high voltages and low voltages applied to first and second sensor/heater elements 4308, 4318 are not the same during the switching interval(s)) and/or may partially overlap (e.g., one or more of the high voltages and/or low voltages applied to first and second sensor/heater elements 4308, 4318 are substantially the same during some portion of the switching interval(s)).

As discussed above, the controller 4380 is configured to alternately supply one or more high voltage(s) and low voltage(s) to each of the first and second sensor/heater elements 4308, 4318. The voltage selection for the high and/or low voltage(s) may be dependent upon the intended application as discussed herein. For example, the high voltage(s) may include any voltage(s) which is larger than the low voltage(s) applied to the other sensor/heater element during at least some period of time (e.g., but is not limited to, 40 V and/or 42 V). Similarly, the low voltage(s) may include any voltage(s) which is smaller than the high voltage(s) applied to the other sensor/heater element during at least some period of time and may include, but is not limited to, ground or a negative voltage (such as, but not limited to, −40 V or −42 V).

The controller 4380 may be configured to cause high and/or low voltages to be applied to the first and second sensor/heater elements 4308, 4318 that are different and/or that vary over time. The selection of the high and/or low voltages may be based one or more operating parameters (e.g., but not limited to, soot accumulation levels, temperature, air flow rates, desired sensitivity, desired power consumption, switching intervals, and/or response time). The controller 4380 may also cause the high voltage applies to one or more of the first and second sensor/heater elements 4308, 4318 to increase and/or decrease over time. For example, the controller 4380 may cause the high voltage(s) to ramp up and/or down progressively and/or in stages over a period of time. Similarly, the controller 4380 may cause the low voltage(s) to ramp up and/or down progressively and/or in stages over a period of time.

Figure 44:
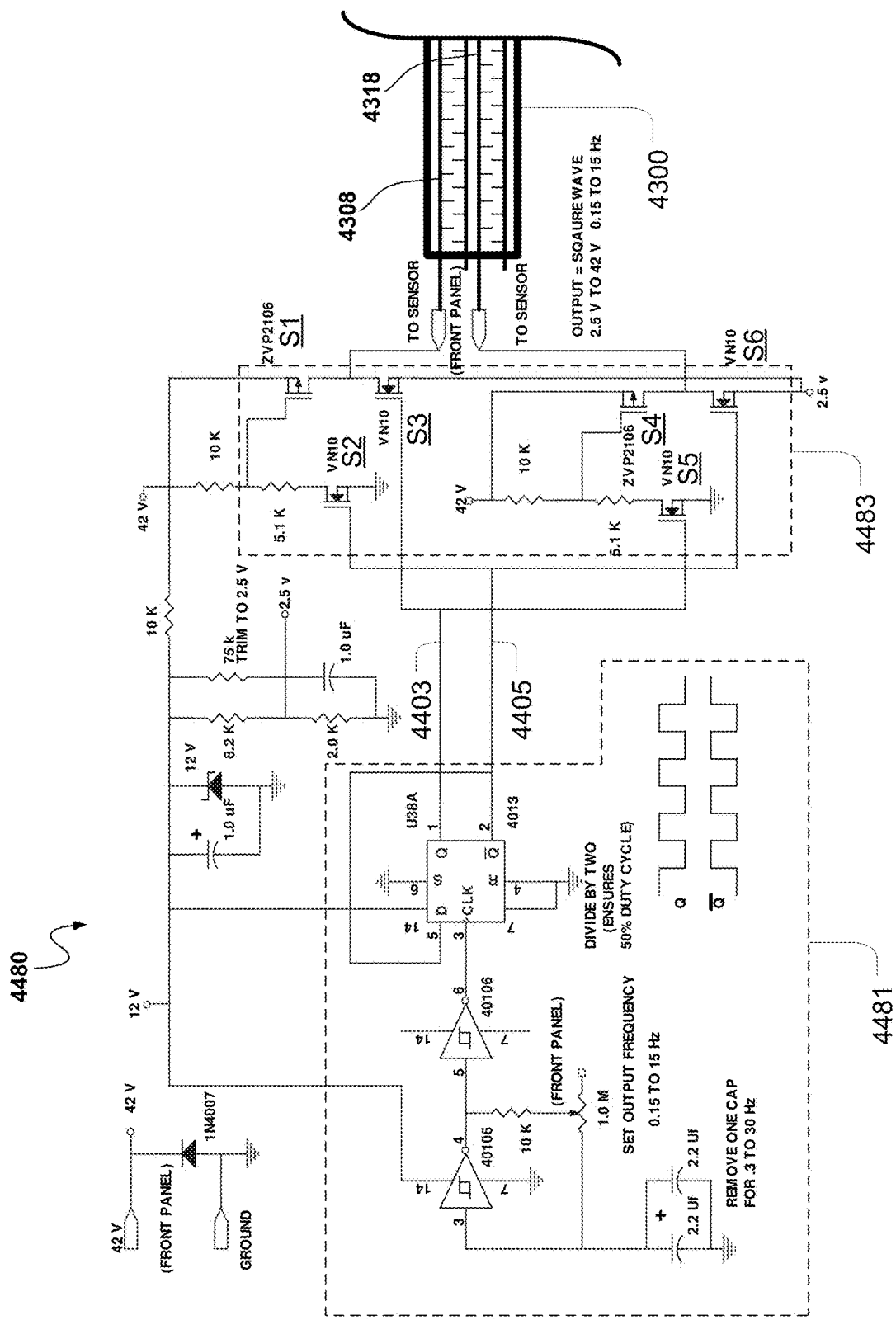
FIG. 44 is a schematic view of one embodiment of the circuitry consistent with the circuitry of FIG. 43.
Figure 50:
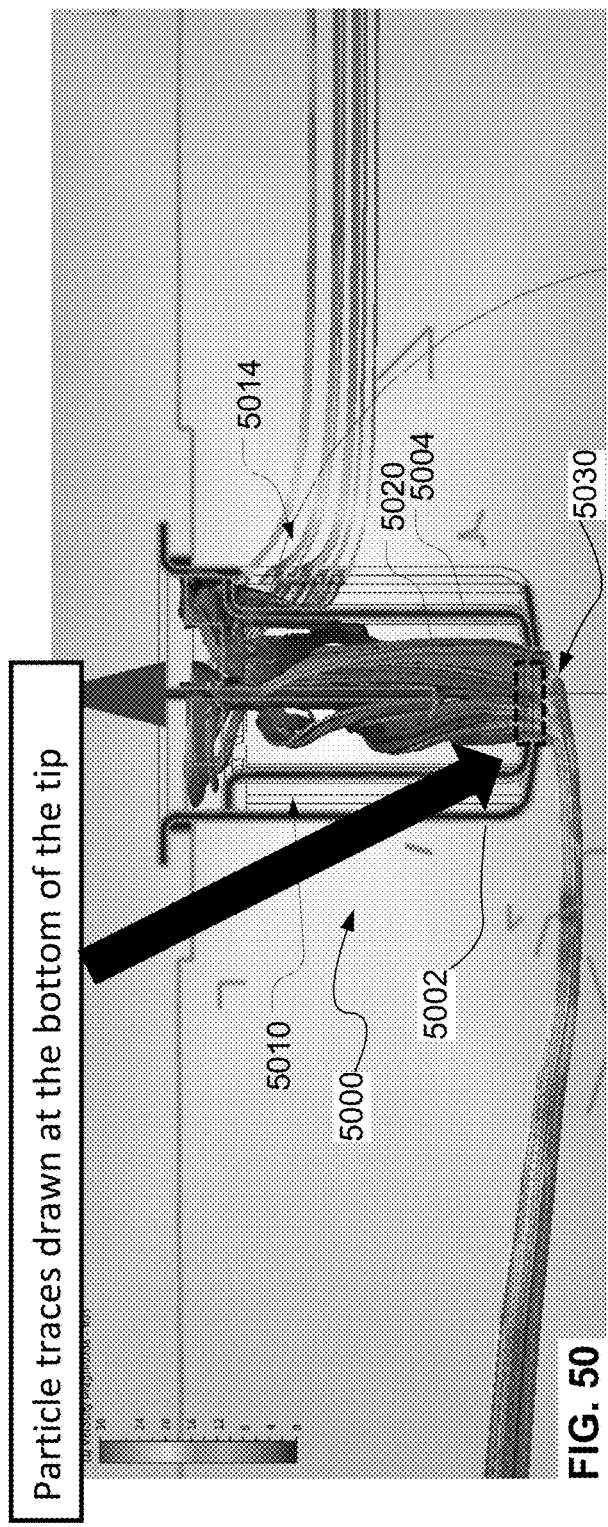
Figure 51:
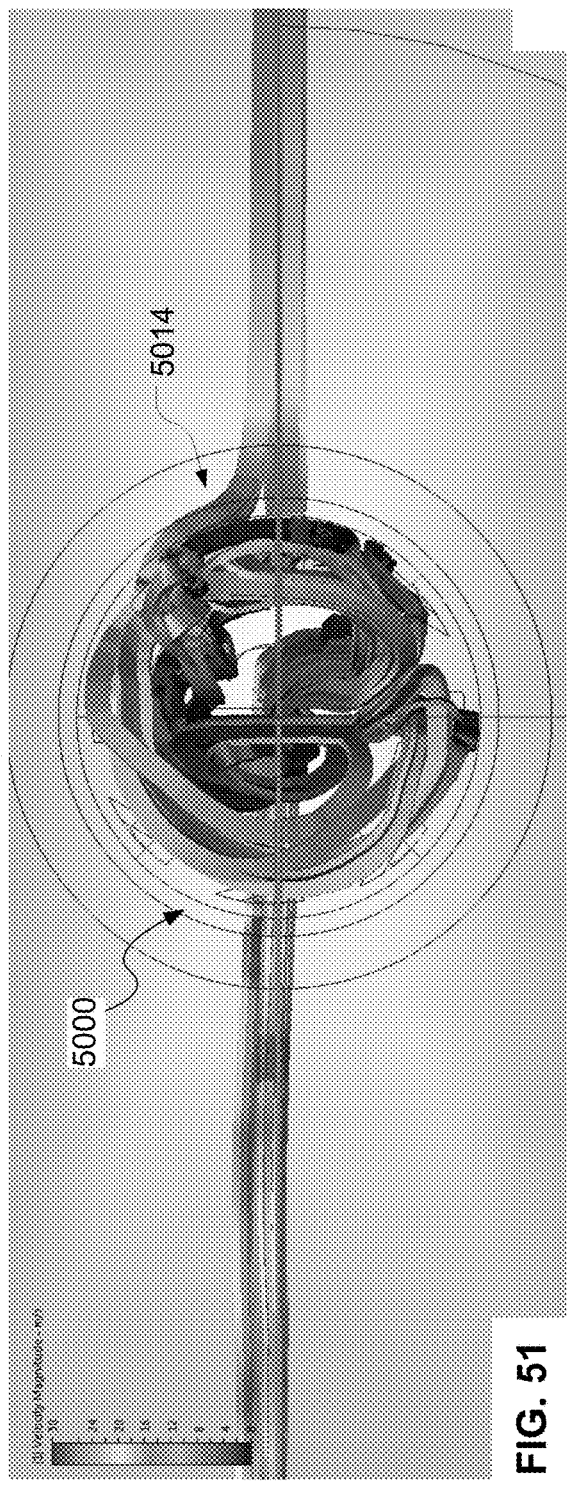

Alternatively, the controller 4380 may be configured to cause a substantially fixed high voltage and low voltage to be applied to the first and second sensor/heater elements 4308, 4318 (e.g., the same high voltage and low voltage is alternately switched to each of the first and second sensor/heater elements 4308, 4318). FIG. 44 generally illustrates one embodiment of a controller 4480 having timing circuitry 4481 and switching circuitry 4483 configured to cause a fixed high voltage and a fixed low voltage to be alternately supplied to the first and second sensor/heater elements 4308, 4318 at a fixed timing interval. In the illustrated embodiment, the controller 4480 is configured to alternately cause a high voltage of 42 V to be applied to each of the first and second sensor/heater elements 4308, 4318 and a low voltage of 2.5 V to be applied to each of the first and second sensor/heater elements 4308, 4318. It should be appreciated, however, that the high and low voltages in FIG. 44 are exemplary values and that the selection of the high and low voltage values may be dependent upon the intended application as discussed herein.

The timing circuitry 4481 is configured to generate switching signals 4403, 4405 that cause the switches S1, S2, S3, S4, S5, and S6 in the switching circuitry 4483 to alternately supply the high voltage (e.g., 42 V) and low voltage (e.g., 2.5 V) to the first and second sensor/heater elements 4308, 4318 of the soot sensor 4300 at a fixed switching interval. The switching signals 4403, 4405 may include a square wave signal and an inverted square wave signal, both of which alternate between a high and a low value. The switching interval (e.g., switching frequency or timing interval) is determined by clock signal CLK, which may be selected/adjusted (e.g., by adding, removing, and/or changing cap values and/or resistor values). For exemplary purposes only, the timing circuitry 4481 is configured to generate a switching interval having a square wave voltage output of 2.5 C to 42 V at 0.15 to 15 Hz. Again, it should be noted that the present disclosure is not limited to the controller 4380 illustrated in FIG. 44 and that any controller may be used to selectively cause high and low voltages to be alternately applied to the soot sensor.

Turning now to FIGS. 45-47, several cross-sectional views of one embodiment of a soot sensor tip assembly 4500 consistent with the present disclosure are illustrated. In particular, FIG. 45 illustrates a cross-sectional view of the soot sensor tip assembly 4500 taken along lines B-B of FIG. 46, FIG. 46 illustrates a cross-sectional view of the soot sensor tip assembly 4500 taken along lines A-A of FIG. 45, and FIG. 47 illustrates a cross-sectional view of the soot sensor tip assembly 4500 taken along lines C-C of FIG. 46. It should be appreciated the soot sensor tip assembly 4500 may be combined with any soot sensor assembly described herein.

Generally, the soot sensor tip assembly 4500 includes an outer tip housing 4502 and an inner tip housing 4504, each having a first end region 4506, 4507 and a second end region 4508, 4509, respectively. At least a portion of the soot sensor tip assembly 4500 is shaped and/or sized to be at least partially disposed within the soot flow (e.g., exhaust system). The inner and/or outer tip housings 4502, 4504 may include metal (such as, but not limited to, steel, stainless steel or the like) and/or non-metal material (e.g., but not limited to, ceramic, composites, and the like). As shown, the second end regions 4508, 4509 of the outer and/or inner tip housings 4502, 4504 may optionally shaped and/or sized to receive a portion of a slug insert (not shown for clarity) as generally described herein.

The outer tip housing 4502 includes an intermediate cavity 4510 which is defined, at least in part, by at least a portion of the sidewall 4512 of the outer tip housing 4502 and at least a portion of the inner tip housing 4504. The intermediate cavity 4510 may have a generally annular configuration as shown; however, the intermediate cavity 4510 is not limited to this configuration. The outer tip housing 4502 includes a plurality of apertures, openings, slits, or the like (hereinafter collectively referred to as fluid flow passageways 4514) disposed along at least a portion of the sidewall 4512. The fluid flow passageways 4514 are sized and shaped to allow soot entrapped in the fluid flow (e.g., exhaust gas) to enter into the intermediate cavity 4510. The fluid flow passageways 4514 may optionally include one or more fluid flow directors 4516 (best seen in FIG. 46). The fluid flow directors 4516 may be configured to cause the fluid entering into the intermediate cavity 4510 to flow in generally radially within the intermediate cavity 4510. Additionally (or alternatively), the fluid flow directors 4516 may be configured to direct some of the fluid flowing past the soot sensor tip assembly 4500 to flow through the fluid flow passageways 4514 and into the intermediate cavity 4510. In the illustrated embodiment, the second end region 4508 of the outer tip housing 4502 may define a flange portion 4518 configured to engagingly mate with a flange portion (not shown for clarity) of the rest of soot sensor assembly as generally described herein. It should be appreciated, however, that the soot sensor tip assembly 4500 may be coupled to the rest of the soot sensor assembly in any manner known to those skilled in the art.

The inner tip housing 4504 includes a sensor cavity 4520 which is defined, at least in part, by the sidewall 4522 of the inner tip housing 4504. The sensor cavity 4520 may have a generally annular configuration as shown; however, the sensor cavity 4520 is not limited to this configuration. The soot sensor tip assembly 4500 further includes a soot sensor 4300 configured to be at least partially disposed within and/or enclosed by the sensor cavity 4520. The soot sensor 4300 may optionally be coupled to a slug insert (not shown for clarity) as generally described herein. For purposes of clarity and description, references will be made to the soot sensor 4300 of FIG. 43. It should be noted, however, that the soot sensor tip assembly 4500 may include other embodiments of a soot sensor consistent with the present disclosure.

The inner tip housing 4504 includes at least one aperture, opening, slit, or the like (hereinafter collectively referred to as sensor passageway 4524, best seen in FIG. 47) disposed along at least a portion of the sidewall 4522. The sensor passageway 4524 is sized, shaped, and/or located to allow soot entrapped in the fluid flow within the intermediate cavity 4510 (e.g., exhaust gas) to enter into the sensor cavity 4520, and ultimately onto the soot sensor 4300. According to one embodiment, the sensor passageway 4524 is disposed within the sidewall 4522 such that the fluid flow flows substantially directly across the active surface of the soot sensor 4300 upon entering the sensor cavity 4520. The sensor passageway 4524 may optionally include one or more fluid flow directors 4526 (best seen in FIG. 45). The fluid flow directors 4526 may be configured to cause the fluid entering into the sensor cavity 4520 to flow generally towards the soot sensor 4300 within the sensor cavity 4520. Additionally (or alternatively), the fluid flow directors 4526 may be configured to direct some of the fluid flowing within the intermediate cavity 4510 to flow through the sensor passageway 4524 and into the sensor cavity 4520. In the illustrated embodiment, the second end region 4509 of the inner tip housing 4504 may define a flange portion 4528 configured to be coupled to engagingly mate with a flange portion (not shown for clarity) of the rest of soot sensor assembly as generally described herein. It should be appreciated, however, that the soot sensor tip assembly 4500 may be coupled to the rest of the soot sensor assembly in any manner known to those skilled in the art.

The inner tip housing 4504 also includes one or more exhaust outlets 4530. The exhaust outlet 4530 is configured to allow exhaust gas within the sensor cavity 4520 to exit the sensor cavity 4520, and therefore the soot sensor tip assembly 4500. Optionally, the outer and/or inner tip housings 4502, 4504 may be configured to create a venture effect to facilitate exhaust gas flow from the intermediate cavity 4510, to the sensor cavity 4520, and exiting the exhaust outlet 4530. Before exiting the sensor cavity 4520, at least some of the soot within the exhaust gas flow contacts the active surface of the soot sensor 4300, thereby allowing the soot sensor 4300 to generate a signal representative of the approximate amount of soot in the exhaust gas.

Turning now to FIGS. 48-49, several cross-sectional views of another embodiment of a soot sensor tip assembly 4800 consistent with the present disclosure are illustrated. In particular, FIG. 48 is a cross-sectional view of the soot sensor tip assembly 4800 taken along lines B-B of FIG. 49 and FIG. 49 is a cross-sectional view of the soot sensor tip assembly 4800 taken along lines A-A of FIG. 48. The soot sensor tip assembly 4800 of FIGS. 48-49 is similar to the soot sensor tip assembly 4500 of FIGS. 45-47 and, only the differences will be described for the sake of brevity. Whereas the soot sensor tip assembly 4500 of FIGS. 45-47 includes a plurality of fluid flow passageways 4514 extending through the outer tip housing 4502, the soot sensor tip assembly 4800 of FIGS. 48-49 includes only a single fluid flow passageways 4814 extending through the outer tip housing 4802. As a result, substantially all of the fluid flow (e.g., exhaust gas) which enters the intermediate cavity 4810 has to flow through the sensor passage 4824 and into the sensor cavity 4820, across the soot sensor 4300, and exit through the exhaust outlet(s) 4830.

It should be appreciated that the sensitivity of the soot sensor within the soot sensor tip assemblies 4500, 4800 may be increased by increasing the length of one or more (e.g., both) of the inner and/or outer tip housings, thereby allowing more soot to come into contact with the soot sensor.

Turning now to FIGS. 50-53, computational fluid dynamic (CFD) simulations results for a soot sensor tip assembly 5000 are generally illustrated. The soot sensor tip assembly 5000 is consistent with the embodiments of FIGS. 45-49. The simulation results show the velocity magnitude of the exhaust gas (m/s) and were performed using boundary conditions including an inlet velocity of 30 m/s at 270° C., outlet pressure of 0 Pa, and laminar flow analysis. As can be seen, the exhaust gas flows generally radially through the soot sensor tip assembly 5000 and enters the outer tip housing 5002, flows though the fluid flow passageways 5014 and into the intermediate cavity 5010, through the sensor passageway 5024, into the sensor cavity 5020, across the soot sensor 4300, and through the exhaust outlet 5030.

A soot sensor consistent with the present disclosure may provide numerous advantages. The single-layer design of the first and second sensor/heater elements 4308, 4318 of the soot sensor 4300 of FIG. 43, for example, provides numerous unique and advantageous features. For example, the effectiveness of regeneration of the soot sensor is improved due to the fact that elements may have the ability to both sense soot accumulation and to heat up to regenerate (i.e. clean) the substrate surface. As such, the elements may serve both roles and there is no need to heat a separate surface, such as the second opposing surface (e.g. back) of the substrate. Additionally, regeneration in high flow conditions is improved. The second surface (e.g. back) of the substrate may be available for additional components, such as another sensor (e.g. high precision exhaust gas temp sensor, etc.) which further adds value and versatility to a system and may reduce costs.

The single layer design also uses less material, including, but not limited to, platinum, when compared to some currently known resistive PM sensors. The price of precious metals, such as platinum, is relatively high and may continue to escalate as it is a finite supply. A soot sensor circuitry consistent with the present disclosure also provides immediate sensor diagnostics self check upon key and on during cold start without operating in regeneration mode. The circuitry is relatively simple and reliable and a diagnostics check may be performed using low current loop.

According to another embodiment, the present disclosure features apparatuses, systems, and methods for reducing and/or eliminating soot (e.g., ash) contamination of a soot sensor. As discussed herein, engine exhaust systems may include at least one diesel particulate filter (DPF). One of the main purposes of a DPF is to remove diesel particulate matter (e.g., soot and ash) from the exhaust gas of a diesel engine. A soot sensor may be provided down stream of the DPF to verify that the DPF is operating properly.

While DPFs are generally effective at capturing diesel particulate particles, there are at least three situations during which soot and/or ash particles may escape the DPF, even though the DPF is not malfunctioning. For example, soot and/or ash particles may escape the DPF during a cold start of the engine system. During a cold start where the engine and/or exhaust system has cooled down (e.g., over night), water condensation may form in the exhaust system. The water may form from water vapor within the exhaust gas and/or atmospheric water that condenses within the exhaust system as the exhaust system cools. Upon start up of the diesel engine, soot and/or ash particles in the exhaust (e.g., ultra-fine ash particles) can mix with the water within the exhaust. The mixture of water and soot and/or ash particles may then escape past the DPF and ultimately contaminate the soot sensor down stream of the DPF.

During cold starts, a dew point signal may be provided to an engine controller to allow the engine controller to determine when all the water is gone from the exhaust system (for example, due to higher exhaust system temperatures). In known prior designs, the engine controller will not allow the soot sensor to go into the heating and/or measurement mode until all of the water is removed from the exhaust system (e.g., based, at least in part, of the dew point signal) in order to prevent damage to the soot sensor (e.g., breaking the ceramic) due to the water from coming into contact with a hot soot sensor.

The second situation in which soot and/or ash particles may escape the DPF is during DPF regeneration. As may be appreciated, the captured soot and/or ash accumulates within the DPF. Regeneration is the process of removing the accumulated diesel particulate matter from the DPF, for example, by burning the accumulated diesel particulate matter. During the burning process, some of the soot and/or ash may escape the DPF and contaminate the soot sensor down stream of the DPF.

The third situation in which soot and/or ash may escape the DPF is during and/or immediately after frequent restarts. This situation is most problematic on diesel engines with automatic start/stop systems (e.g., vehicles that automatically stop and restart when the vehicle comes to a stop and moves again). Testing has shown that even if the engine and/or exhaust system are hot, and no condensation is within the exhaust system, soot and/or ash particles may still escape through the DPF.

As discussed above, the present disclosure features apparatuses, systems, and methods for reducing and/or eliminating soot and/or ash contamination of a soot sensor. While not a limitation of the present disclosure unless specifically claimed as such, the apparatuses, systems, and methods for reducing and/or eliminating soot and/or ash contamination of a soot sensor may be used during one or more of the situations discussed herein during which soot particles may escape from the DPF. The apparatuses, systems, and methods for reducing and/or eliminating soot and/or ash contamination of a soot sensor may also be used in combination or conjunction with any embodiment described herein for sensing soot and/or regenerating the soot sensor.

Figure 54:
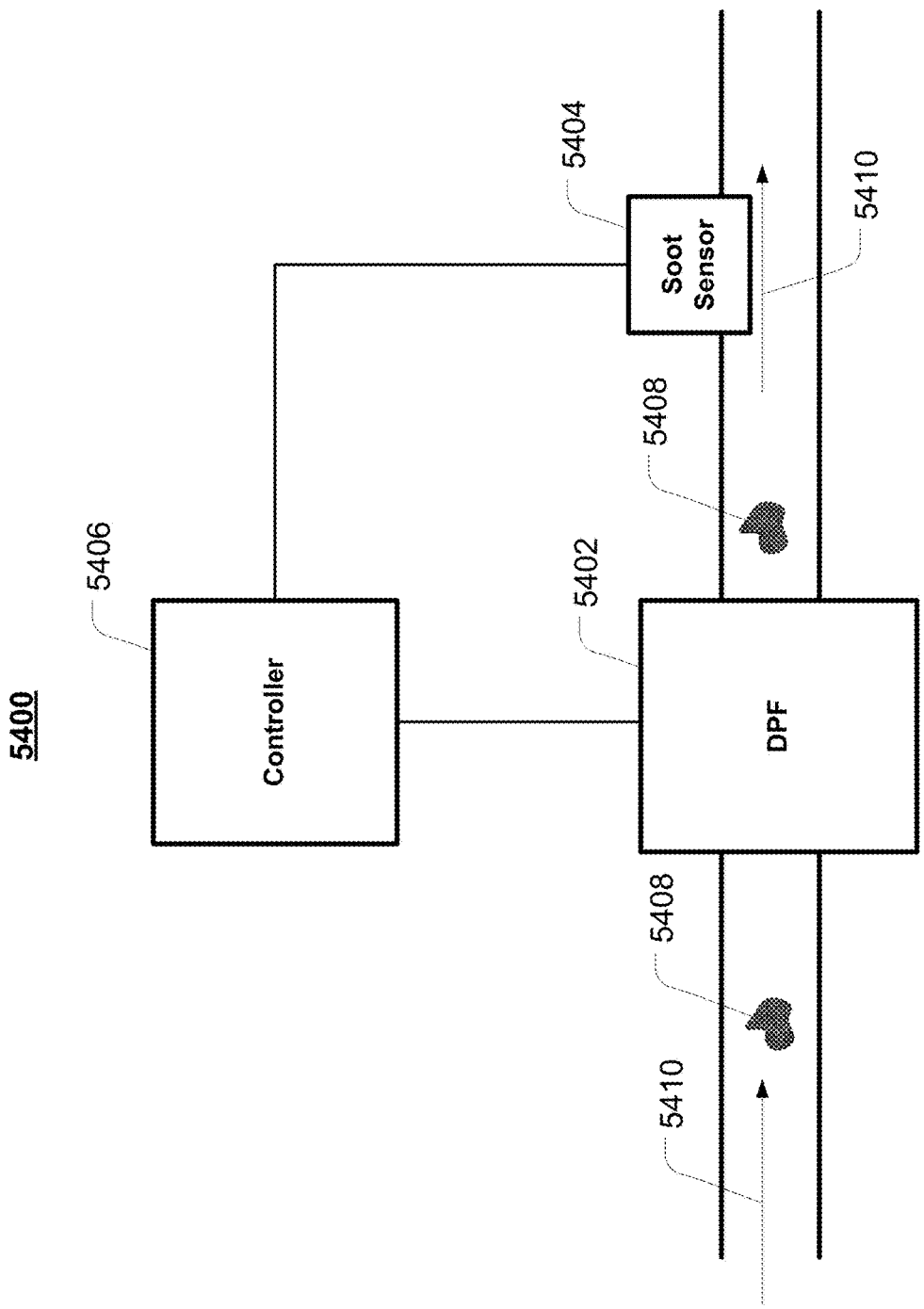
FIG. 54 illustrates one embodiment of a engine exhaust system including a soot sensor system consistent with another embodiment of the present disclosure.

With reference to FIG. 54, an engine exhaust system 5400 for reducing and/or eliminating soot and/or ash contamination of a soot sensor consistent with one embodiment of the present disclosure is generally illustrated. The engine exhaust system 5400 may include at least one DPF 5402, at least one soot sensor 5404, and at least one soot sensor controller 5406. As may be appreciated, the DPF 5402 is configured to generally remove diesel particulate matter 5408 (e.g., soot and/or ash, enlarged for clarity) from the exhaust gas 5410 of a diesel engine (not shown for clarity). However, some soot and/or ash particles 5408 may escape the DPF 5402 during certain situations, for example, but not limited to, the three situations described above.

One or more soot sensors 5404 may be provided down stream of the DPF 5402, for example, to verify that the DPF 5402 is operating properly. Optionally, one or more soot sensors 5404 may be provided either within and/or upstream of the DPF 5402. The soot sensors 5404 may include any soot sensor known to those skilled in the art, and may also include any soot sensor described herein.

Operation of the soot sensors 5408 may be controlled, at least in part, by the soot sensor controller 5406. As described herein, the soot sensor controller 5406 may determine when, how, and how much voltage is to be applied to the soot sensor 5404. The soot sensor controller 5406 may determine the operation of the soot sensor 5404 based, at least in part, on one or more parameters such as, but not limited to, when the DPF 5402 is operating in the regeneration mode, frequency of engine starting and stopping, the dew point within the exhaust system 5400, the temperature of the exhaust gas 5410 and/or diesel engine, the temperature of the soot sensor 5404, the exhaust gas flow rates, the diesel engine rpms, the load on the diesel engine, or the like.

Figure 55:
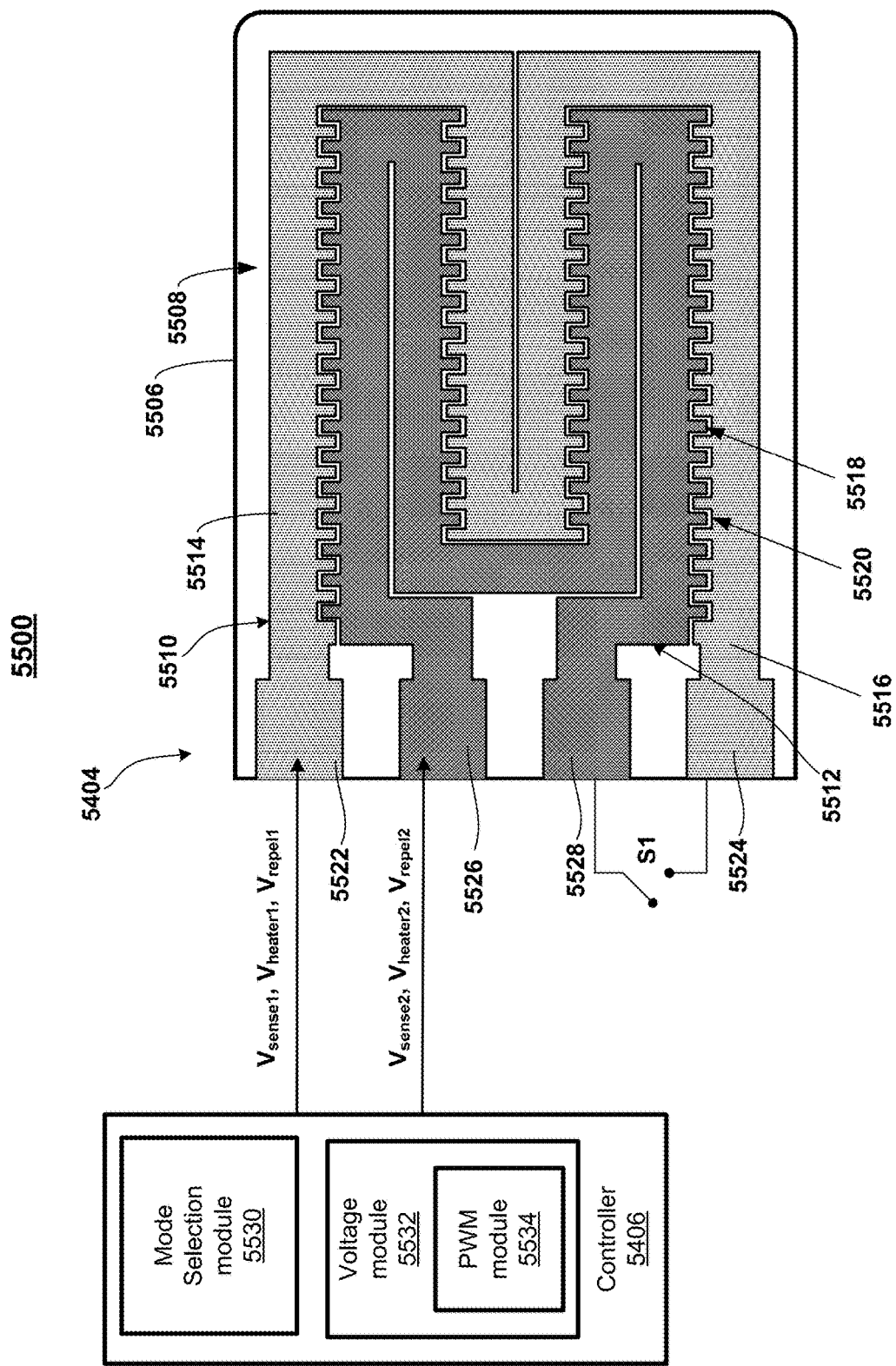
FIG. 55 illustrates one embodiment of the soot sensor system shown in FIG. 54.

Turning now to FIG. 55, a soot sensor 5404 and a soot sensor controller 5406 consistent with at least one embodiment of present disclosure are generally illustrated in more detail. The soot sensor 5404 and the soot sensor controller 5406 may form a soot sensor system 5500.

As discussed herein, the soot sensor 5404 may include any soot sensor known to those skilled in the art, and may also include any soot sensor described herein. In the illustrated embodiment, the soot sensor 5404 includes a substrate 5506 defining a first surface 5508 (e.g. a top surface, similar to first surface 404 of soot sensor 400) and a second surface (not shown) (e.g. a bottom surface, similar to second surface 406 of soot sensor 400) opposing the first surface 5508. At least a first sensor/heater element 5510 (and optionally a second or more sensor/heater element 5512) are formed on the first surface 5508. As described herein, the soot sensor 5404 may be configured to operate in a first mode (hereinafter referred to as "soot sensing mode"), wherein at least one of the first and second sensor/heater elements 5510, 5512 are configured to sense soot accumulation on at least the first surface 5508 of the soot sensor 5404. The soot sensor 5404 may be further configured to operate in a second mode (hereinafter referred to as "regeneration mode"), wherein at least one of the first and second sensor/heater elements 5510, 5512 are configured to heat and remove (e.g. incinerate) at least a portion of accumulated soot on the first surface 5508, thereby cleaning/regenerating the sensor 5502. The soot sensor 5404 may further be configured to operation in a third mode (hereinafter referred to as "contamination prevention mode"), wherein at least one of the first and second sensor/heater elements 5510, 5512 are configured to reduce and/or eliminate soot (ash) contamination of the soot sensor 5002.

The first and second sensor/heater elements 5510, 5512 each include at least one continuous loop of conductive material 5514, 5516, respectively, disposed on the substrate 5506. Similar to the embodiment of FIG. 4, the loops 5514, 5516 may be arranged in a serpentine configuration including first and second sets of undulations 5518, 5520, respectively. As shown, the first sensor/heater element 5510 includes first 5522 and second 5524 electrical contacts at opposite ends of the loop 5514 configured for coupling to circuitry for providing current through the loop 5514. Similarly, the second sensor/heater element 5512 includes first 5526 and second 5528 electrical contacts at opposite ends of the loop 5516 configured for coupling to circuitry for providing current through the loop 5516.

The first and second sensor/heater elements 5510, 5512 may be configured to operate separately and independently from one another, as described in regards to the embodiment of FIG. 4. Additionally, the soot sensor 5404 may further include a switch S1 coupled to the second electrical contacts 5524, 5528 of the first and second sensor/heater elements 5510, 5512, respectively, for selectively coupling and decoupling the contacts 5524, 5528. For example, when the switch S1 is open, the first and second sensor/heater elements 5510, 5512 may operate separately from one another. When the switch S1 is closed, the first and second sensor/heater elements 5510, 5512 may be electrically coupled to one another, establishing a continuous loop of conductive material between contacts 5522 and 5526.

The first and second sensor/heater elements 5510, 5512 may include electrically conductive materials or metals, such as, alumina, gold, platinum, osmium, rhodium, iridium, ruthenium, aluminum, titanium, zirconium, and the like, as well as, oxides, alloys, and combinations including at least one of the foregoing metals. In one embodiment, the elements 5510, 5512 may include alumina having a film platinum trace deposited on a portion thereof.

The substrate 5506 may include non-conductive and/or electrically insulating materials. Materials may include oxides, including, but not limited to, alumina, zirconia, yttria, lanthanum oxide, silica, and/or combinations including at least one of the foregoing, or any like material capable of inhibiting electrical communication and providing structural integrity and/or physical protection. Additionally, the soot sensor 5404 may include thick film and/or thin film constructions.

As discussed herein, the soot sensor system 5500 may also include a soot sensor controller 5406. While the soot sensor controller 5406 is shown having various modules, one or more of the modules may be distributed across one or more components within the engine control system. The soot sensor controller 5406 includes mode selection module 5530 and voltage module 5532 configured to determine when, how, and how much voltage is to be applied to at least one of the first and/or second sensor/heater elements 5510, 5512.

Mode selection module 5530 may be configured to determine which of the three operation modes that the soot sensor 5404 will operate. For example, the mode selection module 5530 may be configured to determine that the soot sensor 5404 will operate in the soot sensing mode whenever it is necessary and/or advantageous to sense soot accumulation on the soot sensor 5404. By way of non-limiting examples, the mode selection module 5530 may cause the soot sensor 5404 to operate in the soot sensing mode based on, at least in part, one or more of the following conditions, a predetermined amount of time after starting, a dew point signal representative of the amount of water within the exhaust system, a temperature signal representative of the temperature of the exhaust and/or engine, or the like. Once the mode selection module 5530 determines that the soot sensor 5404 will operate in the soot sensing mode, the voltage module 5532 may be configured to cause one or more sensing voltage(s) $V_{sense1}$, $V_{sense2}$ to be applied to one or more of the first and second sensor/heater elements 5510, 5512 to sense soot accumulation on the soot sensor 5404 according to any embodiment described herein.

The mode selection module 5530 may also be configured to determine that the soot sensor 5404 will operate in the regeneration mode whenever it is necessary and/or advantageous to clean/regenerate the sensor 5502. By way of non-limiting examples, the mode selection module 5530 may cause the soot sensor 5404 to operate in the regeneration mode when the amount of soot detected on the soot sensor 5404 exceeds a threshold value or range, and/or after a predetermined amount of time has expired since the last regeneration. Once the mode selection module 5530 determines that the soot sensor 5404 will operate in the regeneration mode, the voltage module 5532 may be configured to cause one or more heating voltage(s) $V_{heater1}$, $V_{heater2}$ to be applied to one or more of the first and second sensor/heater elements 5510, 5512 to heat and remove (e.g. incinerate) at least a portion of accumulated soot on the soot sensor 5404 according to any embodiment described herein.

The mode selection module 5530 may also be configured to determine that the soot sensor 5404 will operate in the contamination prevention mode whenever it is necessary and/or advantageous to reduce and/or eliminate soot and/or ash contamination of the soot sensor 5002. By way of non-limiting examples, the mode selection module 5530 may cause the soot sensor 5404 to operate in the contamination prevention mode in any one or more of the following situations, during at least a portion of the duration of a cold start, during at least a portion of the duration of DPF regeneration, and/or for some period of time after frequent restarts. The length of time in which the mode selection module 5530 will cause the soot sensor 5404 to operate in the contamination prevention mode may depend on one or more of a plurality of factors such as, but not limited to, how long it takes for a dew point signal representative of the amount of water within the exhaust system to reach a threshold value, how long it takes for a temperature signal representative of the temperature of the exhaust and/or engine to reach a threshold value, one or more predetermined amounts of time, how long the DPF is operating in the regeneration mode, how long soot and/or ash escape the DPF, or the like.

According to one embodiment, once the mode selection module 5530 determines that the soot sensor 5404 will operate in the contamination prevention mode due to one or more of a cold start, DPF regeneration, and/or frequent restart, the voltage module 5532 may be configured to cause one or more electrostatic repelling voltage(s) $V_{repel1}$, $V_{repel2}$ to be applied to one or more of the first and second sensor/heater elements 5510, 5512 to repel soot and/or ash away from the soot sensor 5404 and reduce and/or eliminate soot and/or ash contamination of the soot sensor 5404.

As discussed herein, soot and/or ash particles have an electrical charge as they travel through the exhaust system. The electrostatic repelling voltage $V_{repel1}$, $V_{repel2}$ applied to the first and/or second sensor/heater elements 5510, 5512 should be selected to be sufficient to create a repelling electrostatic force with the electrically charged soot and/or ash particles at the operating conditions to repel soot and/or ash away from the soot sensor 5404 and generally reduce and/or prevent the soot and/or ash particles from contaminating the soot sensor 5404. The electrostatic repelling voltage $V_{repel1}$, $V_{repel2}$ will depend, for example, on one or more of the following parameters, the charge of the soot and/or ash particles, the velocity of the soot and/or ash particles, the size/weight of the soot and/or ash particles, the amount of soot and/or ash flowing, exhaust pressure, size/configuration of the sensor/heater elements 5510, 5512, etc. By way of non-limiting examples, the electrostatic repelling voltage $V_{repel1}$, $V_{repel2}$ applied to the first and/or second sensor/heater elements 5510, 5512 may be selected from the range of 2-20 volts, for example, 5-15 volts such as 12 volts. The charge of the voltage (i.e., positive or negative) may be chosen depending on the charge of the soot and/or ash particles such that a repelling electrostatic force is generated.

The electrostatic repelling voltage $V_{repel1}$, $V_{repel2}$ may be applied to less than all of the sensor/heater elements 5510, 5512. For example, in a sensor 5502 with two or more sensor/heater elements 5510, 5512, an electrostatic repelling voltage $V_{repel1}$, $V_{repel2}$ may be applied to only one of the sensor/heater elements 5510, 5512. Optionally, the electrostatic repelling voltage $V_{repel1}$, $V_{repel2}$ may be alternately applied to the plurality of sensor/heater elements 5510, 5512. For example, an electrostatic repelling voltage $V_{repel1}$, $V_{repel2}$ may be applied to a first sensor/heater element 5510 during a first time period, then to a second sensor/heater elements 5512 during a second time period (and so on). Two or more of the time periods may overlap. Alternatively (or in addition), the time periods may not overlap.

The electrostatic repelling voltage $V_{repel1}$, $V_{repel2}$ applied to the plurality of sensor/heater elements 5510, 5512 may be the same. Alternatively, different electrostatic repelling voltage $V_{repel1}$, $V_{repel2}$ may be applied to two or more of the plurality of sensor/heater elements 5510, 5512. For example, it may not be necessary to apply the same amount of electrostatic repelling voltage $V_{repel1}$, $V_{repel2}$ to a sensor/heater element 5510 that is arranged/located primarily about a perimeter of the soot sensor 5404 compared to a sensor/heater element 5512 that is arranged/located primarily in the center of the soot sensor 5404.

Optionally, the electrostatic repelling voltage $V_{repel1}$, $V_{repel2}$ may change based on one or more operating parameters of the DPF, diesel engine, or the like. For example, as the efficiency of the DPF increases and less soot and/or ash particles escape the DPF, the electrostatic repelling voltage $V_{repel1}$, $V_{repel2}$ may be decreased. The electrostatic repelling voltage $V_{repel1}$, $V_{repel2}$ may also change based on the engine rpm and/or load. For example, the electrostatic repelling voltage $V_{repel1}$, $V_{repel2}$ may be reduced while the engine is idling under no load (i.e., conditions during which the engine is generating a relatively low amount of soot and/or ash particles and the soot and/or ash particles are flowing at relatively low speed) compared to while the engine is operating at a higher rpm and load (i.e., conditions during which the engine is generating a relatively high amount soot and/or ash particles and the soot and/or ash particles are flowing at relatively high speed). The electrostatic repelling voltage $V_{repel1}$, $V_{repel2}$ may therefore change over time.

According to another embodiment, once the mode selection module 5530 determines that the soot sensor 5404 will operate in the contamination prevention mode due to one or more of a cold start, DPF regeneration, and/or frequent restart, the voltage module 5532 may be configured to cause one or more pulsed heating voltage(s) $V_{heater1}$, $V_{heater2}$ to be applied to the first and/or second sensor/heater elements 5510, 5512, and may be further configured to cause one or more pulsed electrostatic repelling voltage(s) $V_{repel1}$, $V_{repel2}$ to be applied to the first and/or second sensor/heater elements 5510, 5512 during the "off" period of the pulsed heating voltage(s) $V_{heater1}$, $V_{heater2}$ (i.e., during the periods between when the pulsed heating voltage(s) $V_{heater1}$, $V_{heater2}$ is applied). For example, the voltage module 5532 may optionally include a pulse-width modulating (PWM) module 5534 configured to generate the pulsed heating voltage(s) $V_{heater1}$, $V_{heater2}$. The duty cycle of the pulsed heating voltage(s) $V_{heater1}$, $V_{heater2}$ and the pulsed electrostatic repelling voltage(s) $V_{repel1}$, $V_{repel2}$ may be adjustable such that one or more of the pulse widths and/or voltages change over time.

As described herein, the pulsed heating voltage(s) $V_{heater1}$, $V_{heater2}$ may be configured to heat and/or remove (e.g. incinerate) at least a portion of accumulated soot and/or ash particles on the soot sensor 5404 according to any embodiment described herein. By way of non-limiting examples, the pulsed heating voltage(s) $V_{heater1}$, $V_{heater2}$ may be selected to have a polarity (e.g., positive or negative) configured to create a repelling electrostatic force with the charged particulate particles (e.g., soot and/or ash) while heating the first and/or second sensor/heater elements 5510, 5512.

The pulsed electrostatic repelling voltage(s) $V_{repel1}$, $V_{repel2}$ may be configured to repel diesel particulate matter (e.g., soot and/or ash particles) away from the soot sensor and reduce and/or eliminate contamination of the soot sensor 5002 according to any embodiment described herein. By way of non-limiting examples, the pulsed electrostatic repelling voltage $V_{repel1}$, $V_{repel2}$ may be selected from the range of 2-20 volts, for example, 5-15 volts such as 12 volts. The charge of the voltage (i.e., positive or negative) may be chosen depending on the charge of the soot and/or ash particles such that a repelling electrostatic force is generated. The pulsed electrostatic repelling voltage(s) $V_{repel1}$, $V_{repel2}$ may be applied during the entire off period, some portion of the off period, and/or for some predetermined amount of time. The magnitude of one or more of the pulsed electrostatic repelling voltage(s) $V_{repel1}$, $V_{repel2}$ may be smaller than the magnitude of one or more of the pulsed heating voltage(s) $V_{heater1}$, $V_{heater2}$.

According to yet another embodiment, once the mode selection module 5530 determines that the soot sensor 5404 will operate in the contamination prevention mode due to one or more of a cold start, DPF regeneration, and/or frequent restart, the voltage module 5532 may be configured to turn off all voltage and/or cause no voltage to be applied to the first and second sensor/heater elements 5510, 5512. For example, the voltage module 5532 may be configured to connect one or more of the first and second sensor/heater elements 5510, 5512 to ground, and/or float so that the particulate particles (e.g., soot and/or ash) are not attracted to the first and second sensor/heater elements 5510, 5512.

According to yet a further embodiment, once the mode selection module 5530 determines that the soot sensor 5404 will operate in the contamination prevention mode due to one or more of a cold start, DPF regeneration, and/or frequent restart, the PWM module 5534 of the voltage module 5532 may be configured to cause one or more pulsed heating voltage(s) $V_{heater1}$, $V_{heater2}$ to be applied to the first and/or second sensor/heater elements 5510, 5512, and may be further configured to turn off all voltage and/or cause no voltage to be applied to the first and second sensor/heater elements 5510, 5512 during the "off" period of the pulsed heating voltage(s) $V_{heater1}$, $V_{heater2}$. For example, the voltage module 5532 may be configured to connect one or more of the first and second sensor/heater elements 5510, 5512 to ground, and/or float so that the particulate particles (e.g., soot and/or ash) are not attracted to the first and second sensor/heater elements 5510, 5512. As described above, the PWM module 5534 may be configured to change the duty cycle (e.g., pulse widths and/or voltages) change over time.

As noted herein, a dew point signal may be provided to an engine controller during cold starts to allow the engine controller to determine when all the water is gone from the exhaust system (for example, due to higher exhaust system temperatures). In known prior designs, the soot sensor is not allowed to go into the heating and/or measurement mode until all of the water is removed from the exhaust system.

In contrast to the known prior designs, another embodiment of the soot sensor system 5500 is configured to reduce and/or prevent contamination of the soot sensor 5404 by causing one or more heating voltage(s) $V_{heater1}$, $V_{heater2}$ to be applied to the first and/or second sensor/heater elements 5510, 5512 once the mode selection module 5530 determines that the soot sensor 5404 will operate in the contamination prevention mode due to a cold start. The voltage module 5532 may therefore be configured to cause the heating voltage(s) $V_{heater1}$, $V_{heater2}$ to be applied to the first and/or second sensor/heater elements 5510, 5512 to heat and/or remove (e.g. incinerate) at least a portion of the soot and/or ash as it accumulates on the soot sensor 5404. The heating voltage(s) $V_{heater1}$, $V_{heater2}$ may be applied during the entire cold start period, some portion of the cold start period, and/or for some predetermined amount of time. Optionally, one or more of the heating voltage(s) $V_{heater1}$, $V_{heater2}$ may be applied in a PWM format as described herein.

Thus, the present disclosure features apparatuses, systems, and methods for reducing and/or eliminating soot and/or ash contamination of a soot sensor. Any of the apparatuses, systems, and methods for reducing and/or eliminating soot and/or ash contamination of a soot sensor may be used in combination or conjunction with any of the apparatuses, systems, and methods for sensing soot and/or regenerating the soot sensor as described herein. In addition, any of the apparatuses, systems, and methods for reducing and/or eliminating soot and/or ash contamination of a soot sensor may be used with any soot sensor described herein or known to those of ordinary skill in the art. For example, while the embodiment of the sensor shown in FIG. 55 includes a first and a second sensor/heater element, the sensor may include only one heater element and/or only one sensor element. Additionally, one or more of the heater elements and sensor elements may be independent (i.e., they may function to only heat or only sense).

Consistent with one embodiment of the present disclosure, there is provided a soot sensor system including a soot sensor and a controller configured to cause a regeneration pulse-width modulating (PWM) signal to be applied to the soot sensor during a regeneration mode to heat at least a portion of the soot sensor to a regeneration temperature. The controller, during the regeneration mode, is further configured to cause a sensing signal to be applied to the soot sensor during an off-time of the regeneration PWM signal to sense accumulation of soot on the soot sensor. Optionally, the controller is configured to cause a sense current $I_{sense}$ to be applied to the soot sensor during the off-time of the regeneration PWM signal, wherein the sense current $I_{sense}$ is used to determine an amount of soot accumulated on the soot sensor.

Consistent with another embodiment of the present disclosure, there is provided a soot sensor system including a soot sensor and a controller configured to cause the soot sensor to be heated to an initial regeneration temperature. The controller thereafter is configured to 1) determine if a slope of the resistance of said soot sensor has remained substantially constant for a predetermined amount of time. If the slope of the resistance has not remained substantially constant, the controller is further configured to cause an increase in temperature of the soot sensor and repeat the determining step 1. If the slop of the resistance has remained substantially constant, the controller is further configured to cause a decrease in the temperature of the soot sensor and measure the soot sensor for openness at the decreased temperature. If the openness is detected at the decreased temperature, the controller is configured to stop the regeneration mode and if the openness is not detected at the decreased temperature, the controller is configured to cause an increase in temperature of the soot sensor and repeat the determining step 1.

The controller is optionally configured to cause a 25° C. increase in temperature of the soot sensor. The controller may also be configured to determine if the slope of the resistance of the soot sensor has remained substantially constant for at least a portion of the predetermined amount of time. The predetermined amount of time may be at least 20 seconds and the slope of the resistance may be deemed to have remained substantially constant if the slope of the resistance remains relatively constant for a period of at least 10 seconds during the predetermined amount of time.

Consistent with yet another embodiment of the present disclosure, there is provided a soot sensor system including a soot sensor and a controller configured to cause a variable sensing signal to be applied to the soot sensor during a sensing mode to sense accumulation of soot on the soot sensor. The variable sensing signal has a first voltage upon initiation of the sensing mode, and the variable sensing signal has a second voltage a period of time after initiation of the sensing mode. The first voltage being greater than the second voltage.

The first voltage may be selected from a range of 5 to 60 V. The controller may be further configured to determine the second voltage based, at least in part, on a temperature of an exhaust to be measured. Optionally, the controller may be configured to cause the second voltage to decrease as the exhaust temperature increases and/or may be configured to cause the second voltage to increase as the exhaust temperature decreases. The controller may be further configured to cause the soot sensor system to enter into the sensing mode during or shortly after active regeneration of a diesel particulate filter.

Consistent with one embodiment of the present disclosure, there is provided a soot sensor including a substrate defining a first surface and a second surface opposing the first surface, a first element having at least one continuous loop of conductive material disposed on the first surface of the substrate, and a passivation layer disposed over a portion of the first surface to shield portions of the first surface from accumulation of soot thereon. The first element being configured to operate in a sensing mode to sense accumulation of soot on at least the first surface of the substrate and to operate in a regeneration mode to remove accumulated soot on at least the first surface of the substrate.

The passivation layer may include glass. The passivation layer may be further disposed over a portion of the first element to shield portions of the first element from accumulation of soot thereon. Optionally, the passivation layer is configured to shield at least a portion of an edge region of the first surface of the substrate from accumulation of soot thereon. The passivation layer is disposed over the portion of the first surface based in a pattern based on temperature gradient of the soot sensor during the regeneration mode such that the passivation layer allows soot to substantially only accumulate on exposed portions of the soot sensor where, during the regeneration mode, a temperature of the exposed portions of the soot sensor is sufficient to at least partially incinerate soot.

Consistent with yet a further embodiment of the present disclosure, there is provided a method of measuring an amount of soot deposited on a soot sensor. The method includes providing a soot sensor having a substrate defining a first surface and a second surface opposing the first surface and a first element having at least one continuous loop of conductive material disposed on the first surface of the substrate, the first element being configured to operate in a first mode to sense accumulation of soot on at least the first surface of the substrate and to operate in a second mode to remove accumulated soot on at least the first surface of the substrate. The method further includes applying a high voltage to the first element and monitoring a sense current through the first element, the current being representative of an amount of soot accumulated on the first element; and applying a low voltage a predetermined amount of time after applying the high voltage and monitoring a sense current through the first element, the current being representative of an amount of soot accumulated on the first element.

Consistent with one an additional embodiment of the present disclosure, there is provided a soot sensor system including a soot sensor and a controller. The soot sensor includes a substrate defining a first surface and a second surface opposing the first surface and a first element having at least one continuous loop of conductive material disposed on the first surface of the substrate. The controller is configured to cause a regeneration pulse-width modulating (PWM) signal to be applied to the first element of the soot sensor during a regeneration mode to heat at least a portion of the soot sensor to a regeneration temperature. The controller, during the regeneration mode, is further configured to determine a temperature of the substrate of the soot sensor during an off-time of the regeneration PWM signal. Optionally, the controller is configured to determine the temperature of the substrate of the soot sensor during the off-time of the regeneration PWM signal based on a resistance of the first element of the soot sensor during the off-time of the regeneration PWM.

Consistent with another embodiment of the present disclosure, there is provided a soot sensor system including a soot sensor and a controller. The soot sensor includes a substrate defining a first surface and a second surface opposing the first surface and a first and a second element each having at least one continuous loop of conductive material disposed on the first surface of the substrate. The first and the second elements are each being configured to operate in a sense mode to sense accumulation of soot on at least the first surface of the substrate. During a first time period of the sensing mode, the controller is configured to cause a first voltage to be applied to the first element that is greater than a second voltage applied to the second element. During a second time period of the sensing mode, the controller is further configured to cause a third voltage to be applied to the second element that is greater than a fourth voltage applied to the first element.

The second time period may begin when the first time period ends. Alternatively, the first and the second time periods partially overlap. Optionally, the first voltage may be substantially the same as the third voltage. The first and the third voltages may be selected from the range of 5 to 60 V, for example, from the range of 40 to 42 V. The second voltage may be substantially the same as the fourth voltage. Optionally, the second and fourth voltages are each substantially equal to the negative voltages of the first and the third voltages, respectively. The second and the fourth voltages may be selected from the range of −60 to 2.5 V, for example, from the range of −40 to −42 V. The first and third voltage potentials may be each greater than 5 V and the second and fourth voltage potentials may each at ground.

Consistent with yet another embodiment of the present disclosure, there is provided a soot sensor assembly including a housing, a sensor tip, a soot sensor, a plurality of lead wires, and a fixing material. The housing includes a first end region, a second end region generally opposite the first end region, and at least one passageway disposed within the housing. The sensor tip extends from the first end region of the housing and at least partially defines a sensor cavity. The soot sensor is at least partially disposed within the sensor cavity. The plurality of lead wires are at least partially disposed within the at least one passageway and extend from the soot sensor towards the second end region. The fixing material is disposed within a portion of the at least one passageway and over a portion of the plurality of lead wires. The fixing material seals the plurality of lead wires to the housing.

Optionally, the fixing material includes a liquid material that cures into a solid material to seal the plurality of lead wires to the housing. The fixing material may include an electrically insulating material when cured. The fixing material may include a glass material and/or a thermosetting plastic.

Consistent with one embodiment of the present disclosure, there is provided a soot sensor. The soot sensor includes a substrate defining a first surface and a second surface opposing the first surface. The soot sensor further includes a first element having at least one continuous loop of conductive material disposed on the first surface of the substrate. The at least one element is configured to operate in a first mode to sense accumulation of soot on at least the first surface of the substrate and to operate in a second mode to remove accumulated soot on at least the first surface of the substrate.

Consistent with another embodiment of the present disclosure, there is provided a soot sensor system. The soot sensor system includes a soot sensor. The soot sensor includes a substrate defining a first surface and a second surface opposing the first surface. The soot sensor further includes a first element having at least one continuous loop of conductive material disposed on the first surface of the substrate. The at least one element is configured to operate in a first mode to sense accumulation of soot on at least the first surface of the substrate and to operate in a second mode to remove accumulated soot on at least the first surface of the substrate.

The soot sensor system further includes circuitry electrically coupled to the first element. The circuitry is configured to provide electrical current to the first element and to determine an amount of soot accumulated on the first surface of the substrate and the first element and to control heating of first element in response to the soot accumulated on the first surface of the substrate and the first element.

Consistent with yet another embodiment of the present disclosure, there is provided a method of measuring an amount of soot deposited on a soot sensor. The method includes providing a soot sensor. The soot sensor includes a substrate defining a first surface and a second surface opposing the first surface. The soot sensor further includes a first element having at least one continuous loop of conductive material disposed on the first surface of the substrate. The at least one element is configured to operate in a first mode to sense accumulation of soot on at least the first surface of the substrate and to operate in a second mode to remove accumulated soot on at least the first surface of the substrate.

The method further includes monitoring a sense current through the first element, the current being representative of an amount of soot accumulated on the first element. The method further includes providing heater current through the first element in response to the monitoring step when the sense current reaches a predetermined threshold to thereby remove at least a portion of the soot accumulated on the first element.

In yet a further embodiment of the present disclosure, there is provided a soot sensor top assembly including an inner tip housing, an outer tip housing, and a soot sensor. The inner tip housing includes a sensor cavity defined, at least in part, by at least a portion of a sidewall of the inner tip housing. The outer tip housing includes an intermediate cavity defined, at least in part, by at least a portion of a sidewall of the outer tip housing and at least a portion of the inner tip housing. The soot sensor is at least partially disposed within the sensor cavity. The outer tip housing further includes a first fluid flow passageway extending through the outer tip housing configured to allow soot to enter into the intermediate cavity and the inner tip housing further includes a second fluid flow passageway extending through the inner tip housing configured to allow soot to enter into the sensor cavity and accumulate on the soot sensor.

The soot sensor top assembly optionally includes at least one exhaust outlet configured to allow soot to exit the sensor cavity. The outer tip housing may include a plurality of fluid flow passageways configured to allow soot to enter into the intermediate cavity. Alternatively, the outer tip housing includes only the first fluid flow passageway configured to allow soot to enter into the intermediate cavity. The second fluid flow passageway may be configured to direct soot towards an active surface of the soot sensor.

Another aspect of the present disclosure may feature a soot sensor system including a soot sensor and a controller configured to cause an electrostatic repelling voltage to be applied to the soot sensor during a contamination prevention mode to at least partially repel ash away from the sensor.

Yet another aspect of the present disclosure may feature a soot sensor system including a soot sensor and a controller configured to cause, during a contamination prevention mode, a pulsed heating voltage to be applied to the soot sensor and further configured to cause a pulsed electrostatic repelling voltage to be applied to the soot sensor during an off period of the pulsed heating voltage, the pulsed electrostatic repelling voltage configured to at least partially ash soot away from the sensor.

A further aspect of the present disclosure may feature a soot sensor system including a soot sensor and a controller configured to cause no voltage to be applied to the soot sensor during a contamination prevention mode to reduce the attraction of ash to the soot sensor.

An additional aspect of the present disclosure may feature a soot sensor system including a soot sensor and a controller configured to cause, during a contamination prevention mode, a pulsed heating voltage to be applied to the soot sensor and further configured to cause no voltage to be applied to the soot sensor during an off period of the pulsed heating voltage.

Yet an additional aspect of the present disclosure may feature a soot sensor system including a soot sensor and a controller configured to cause a heating voltage to be applied to the soot sensor during a contamination prevention mode to at least partially incinerate soot from the sensor.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

As used in any embodiment herein, the term "module" may refer to software, firmware and/or circuitry configured to perform any of the aforementioned operations. Software may be embodied as a software package, code, instructions, instruction sets and/or data recorded on non-transitory computer readable storage mediums. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. The modules may, collectively or individually, be embodied as circuitry that forms part of a larger system, for example, an integrated circuit (IC), system on-chip (SoC), engine control unit (ECU), electronic engine controller (EEC), or the like.

What is claimed is:

1. A soot sensor system comprising:
   a soot sensor, said soot sensor comprising:
      a substrate defining a first surface and a second surface opposing said first surface; and
      a first and a second element each having at least one continuous loop of conductive material disposed on said first surface of said substrate; and
   circuitry to cause a regeneration pulse-width modulating (PWM) signal to be applied to said soot sensor during a regeneration mode to heat at least a portion of said soot sensor to a regeneration temperature, and wherein said circuitry, during said regeneration mode, is further configured to cause a sensing signal to be applied to said soot sensor during an off-time of said regeneration PWM signal to sense accumulation of soot on said soot sensor.

2. The soot sensor system of claim 1, wherein said circuitry is configured to cause a sense current $I_{sense}$ to be applied to said soot sensor during said off-time of said regeneration PWM signal, wherein said sense current $I_{sense}$ is used to determine an amount of soot accumulated on said soot sensor.

3. The soot sensor system of claim 1, wherein said circuitry is configured to cause said regeneration PWM signal to be applied to said first element and is further configured to cause said sensing signal to be applied to said first element during an off-time of said regeneration PWM sign.

4. The soot sensor system of claim 1, wherein said circuitry is configured to cause said regeneration PWM signal to be applied to said first and said second elements and is further configured to cause said sensing signal to be applied to said first and said second elements during an off-time of said regeneration PWM signal.

5. The soot sensor system of claim 1, wherein said sensing signal occurs intermittently during said regeneration mode to determine an effectiveness of said regeneration mode.

6. The soot sensor system of claim 1, wherein said regeneration temperature is sufficient to incinerate at least some of soot accumulated on said soot sensor.

7. The soot sensor system of claim 1, wherein said circuitry is further configured to perform a rationality test in response to active regeneration of a diesel particulate filter (DPF).

8. The soot sensor system of claim 7, wherein said circuitry is configured to perform said rationality test during active regeneration of said DPF.

9. The soot sensor system of claim 7, wherein said circuitry is configured to perform said rationality test after active regeneration of said DPF.

10. The soot sensor system of claim 7, wherein said circuitry is further configured to cause a soot sensing mode sensing signal to be applied to said soot sensor during a soot sensing mode to sense accumulation of soot on said soot sensor.

11. The soot sensor system of claim 10, wherein a voltage of said soot sensing mode sensing signal is larger during said rationality test than a voltage of said soot sensing mode sensing signal after termination of said rationality test.

12. The soot sensor system of claim 1, wherein during said regeneration mode, said circuitry is configured to provide gradual heating of at least one of said first or said second elements and further configured to sense soot accumulation at different temperature levels during said off-time of said regeneration PWM signal.

13. The soot sensor system of claim 12, wherein during said regeneration mode, said circuitry is configured to determine regeneration effectiveness based on said detected sense soot accumulation at said different temperature levels.

14. The soot sensor system of claim 13, wherein said circuitry is configured to determine if a resistance of at least one of said first or said second elements is leveled out during a predetermined time period.

15. The soot sensor system of claim 14, wherein if said resistance has leveled out during said predetermined time period, then said circuitry is configured to terminate said regeneration mode.

16. The soot sensor system of claim 14, wherein if said resistance has not leveled out during said predetermined time period, then said circuitry is configured to increase said regeneration temperature.

* * * * *